United States Patent [19]
Janda

[11] Patent Number: 5,571,681
[45] Date of Patent: Nov. 5, 1996

[54] CHEMICAL EVENT SELECTION BY SUICIDE SUBSTRATE CONJUGATES

[75] Inventor: Kim D. Janda, San Diego, Calif.

[73] Assignee: The Scripps Research Institute, La Jolla, Calif.

[21] Appl. No.: 209,525

[22] Filed: Mar. 10, 1994

[51] Int. Cl.$^6$ .............................. C12Q 1/25; C12N 9/00
[52] U.S. Cl. ......................... 435/7.6; 435/188.5; 435/41
[58] Field of Search ................................ 435/188.5, 7.6, 435/7.71, 7.72, 41

[56] References Cited

U.S. PATENT DOCUMENTS 5,030,717  7/1991  Tramontano et al. .................. 530/387

OTHER PUBLICATIONS

Lerner, et. al. "Antibodies Without Immunization", *Science*, 258: 1313–1314 (1992).
Lerner, et. al. "At The Crossroads Of Chemistry And Immunology: Catalytic Antibodies" *Science*, 252: 659–667 (1991).
Lerner, et. al. "Semisynthestic Combinatorial Antibody Libraries: A Chemical Solution To The Diversity Problem", *Proc. Natl. Acad. Sci.*, 89: 4457–4461 (1992).
Barbas, C. F., et. al. (1993) Gene 137, 52–62.
Burton, P. R. (1993) Acc. Chem. Res 26, 405–411.
Barbas, C. F., et. al. (1992) Proc. Natl. Acad. Sci, USA 89, 4457–4461.
Barbas, C. F. et. al. (1993) Proc. Natl. Acad. Sci, USA 90, 6385–6389.

*Primary Examiner*—Charles L. Patterson, Jr.
*Attorney, Agent, or Firm*—Donald G. Lewis

[57] ABSTRACT

Molecules having covalent catalytic activity are identified by panning synthetic and semisynthetic combinatorial libraries on solid phase suicide substrates. In an alternative mode, mechanism-based inhibitors or affinity labels may substituted for the suicide substrate. Covalent catalysts within the combinatorial library form covalent conjugates with the suicide substrate, mechanism-based inhibitor, or affinity label. Covalent conjugates are immobilized by attachment to the suicide substrate to solid phase and are easily separated from unconjugated elements of the combinatorial library by stringent washing. Combinatorial libraries employing phagemid-display are particularly preferred since such phagemids include genetic material for identifying and amplifying conjugated catalysts. Covalent catalysts obtainable by this method include, inter alia, molecules having esterolytic activity, aldol condensation activity, β-lactamase activity, glycosidase activity, RNase activity, and proteolytic activity.

5 Claims, 13 Drawing Sheets

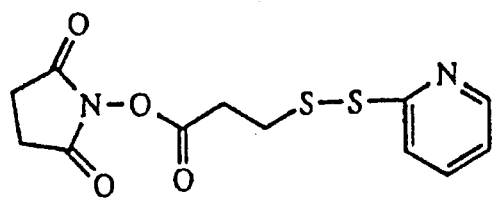
SPDP
16
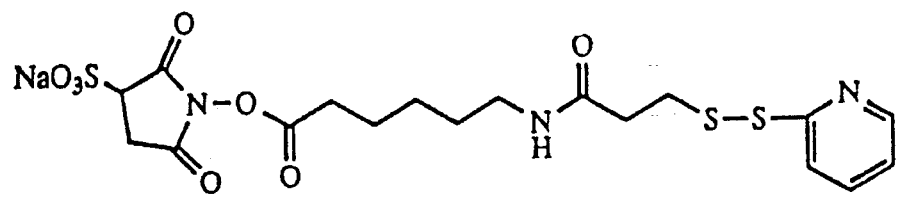
Sulfo-LC-SPDP
17
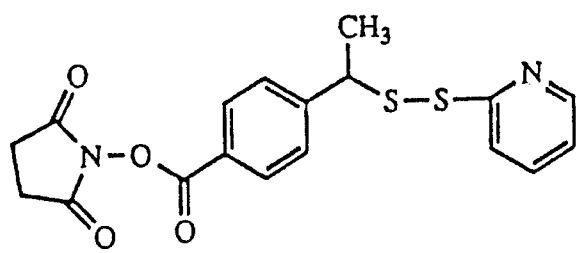
SMPT
1
FIG. 1

| CLONE DESIGNATION | $V_H$ CDR3 | SEQ ID NO | $V_L$ CDR3 | SEQ ID NO | COMPOUND |
|---|---|---|---|---|---|
| 12-2 | YYCARGRDSFSGLVGAQLQDDWGQG | 42 | QQYGGSPWFGQ | 26 | 16 |
| 12-3 | YYCARGSGLLTFWASMLPDDRWGQG | 43 | QQYGGSPWFGQ | 26 | |
| 12-8 | YYCARGGSQMWCQDK------WGQG | 44 | QQYGGSPWFGQ | 26 | |
| 12-10 | YYCARGLYSTYWFTQSGDGWGQG | 45 | QQYGGSPWFGQ | 26 | |
| 22-3 | YYCARGVNVTFGFSRRSQLDWGQG | 46 | QQYGGSPWFGQ | 26 | 17 |
| 22-4 | YYCARGVGMNFVRWGWNGRDVWGQG | 47 | QQYTTTMEVTFGG | 50 | |
| 22-6 | YYCARGSPFTRPCDK------WGQG | 48 | QQYGGSPWFGQ | 26 | |
| 22-7 | YYCARCHLDD----------WGQG | 49 | QQYGQASATFGG | 51 | |
| 32-1 | YYCARGLMRILITDV------WGQG | 29 | QQYGGSPWFGQ | 26 | 1 |
| 32-3 | YYCARGVALSVVWVPMGSSDFWGQG | 30 | QQYGGSPWFGQ | 26 | |
| 32-5 | YYCARGSRSQVMLRGSIVWDFWGQG | 31 | QQYGGSPWFGQ | 26 | |
| 32-6 | YYCARGVYPVPVGTGPQLIHDAWGQG | 32 | QQYGGSPWFGQ | 26 | |
| 32-7 | YYCARGGRDEFGCDY------WGQG | 33 | QQYKRGLLSTFGG | 38 | |
| 32-9 | YYCARGVGVRRQGDP------WGQG | 34 | QQYGGSPWFGQ | 26 | |
| 32-10 | YYCARGRRITARLDG------WGQG | 35 | QQSRMGGAGTEGG | 39 | |
| 32-11 | YYCARGIYQCTKADP------WGQG | 36 | QQYQRMSWLTPGG | 40 | |
| 32-12 | YYCARGMVLKSGKDF------WGQG | 37 | QQYRAAKWNTPGG | 41 | |

FIG. 2

FIG. 3
Protein Conjugated Suicide Substrate Reagent
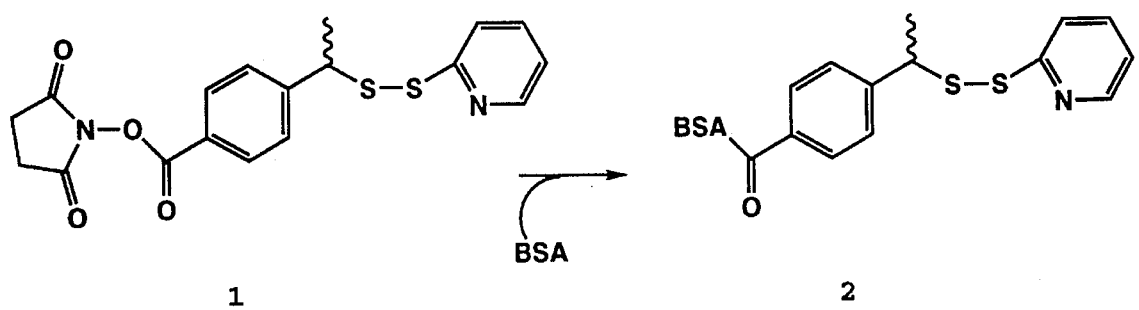
Immobilized BSA/Suicide Substrate Conjugate
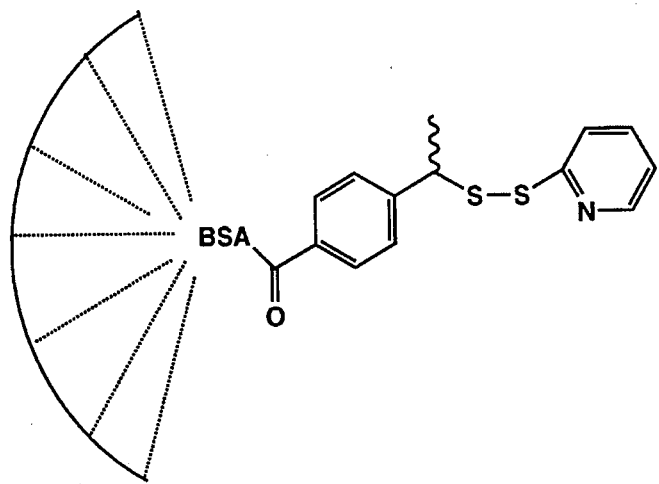
FIG. 4

FIG. 5
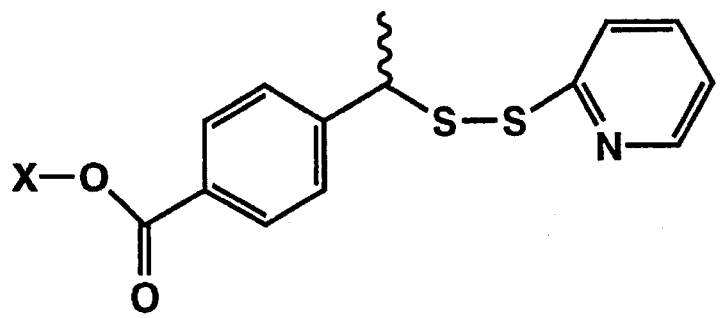
A  X = 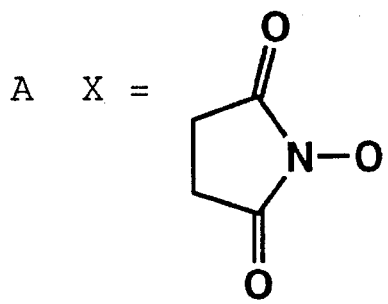
B  X =   BSA
C  X =   CH₃NH
D  X =   [¹⁴CH₃]NH
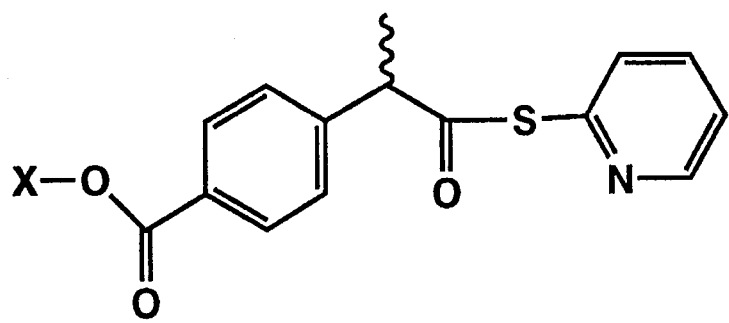
E  X =   HCONH
F  X =   H

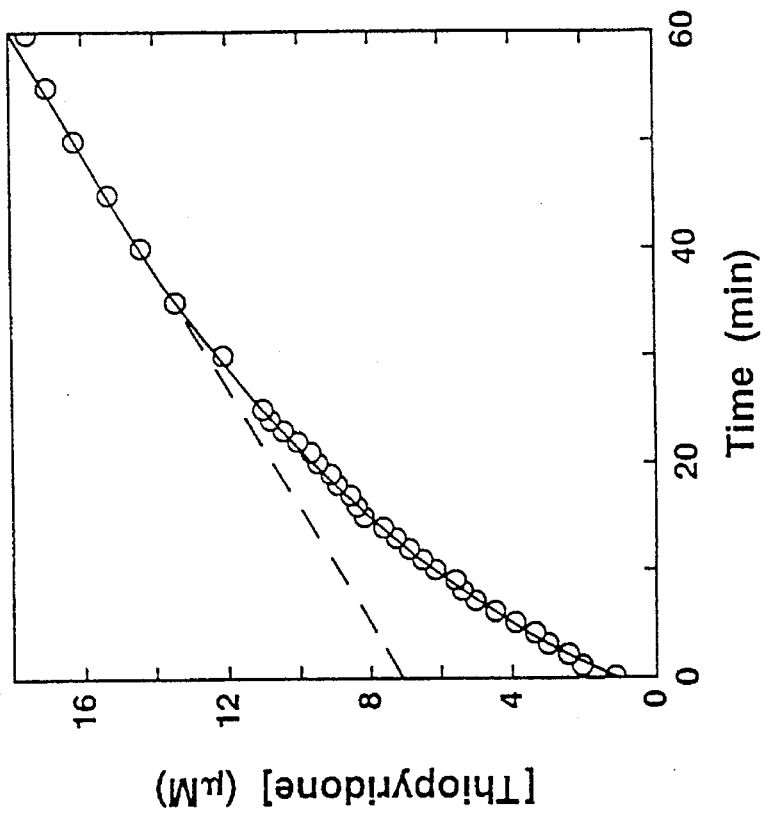
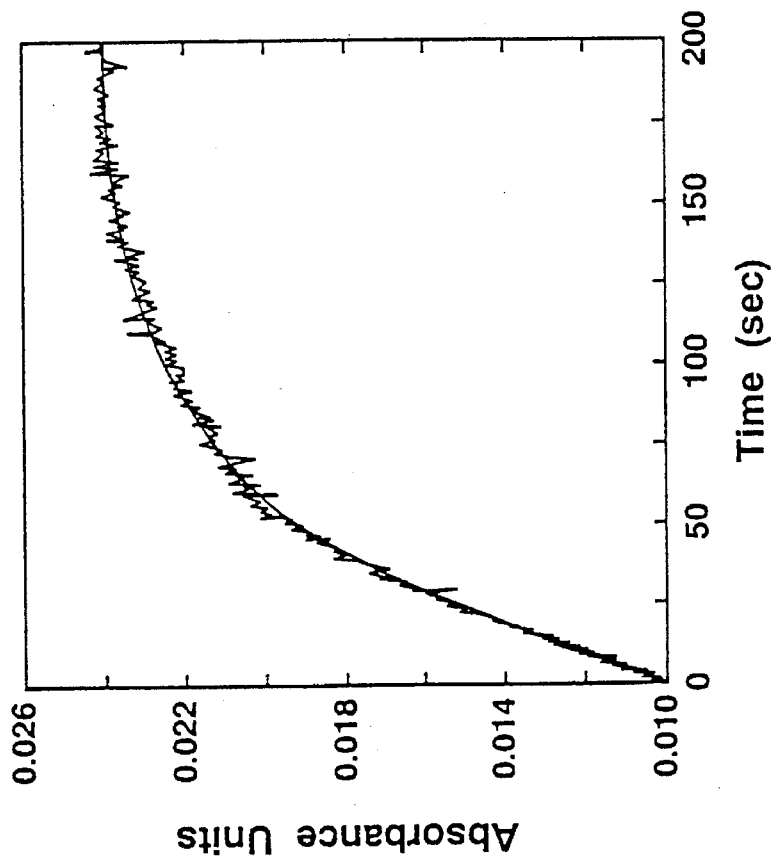

Immobilized Suicide Substrate
For Selection of Cysteine or Serine Nucleophiles

FIG. 9    X = Nucleophile

Selection for Aldol Condensation Reactions

Immobilized Suicide Substrate
For Selection of β-Lactamase
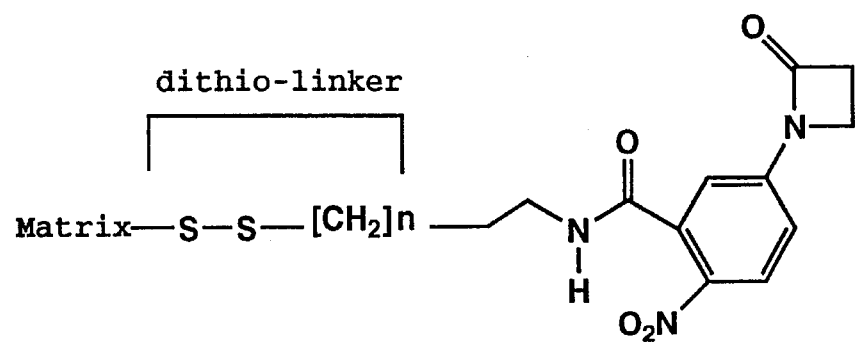
8
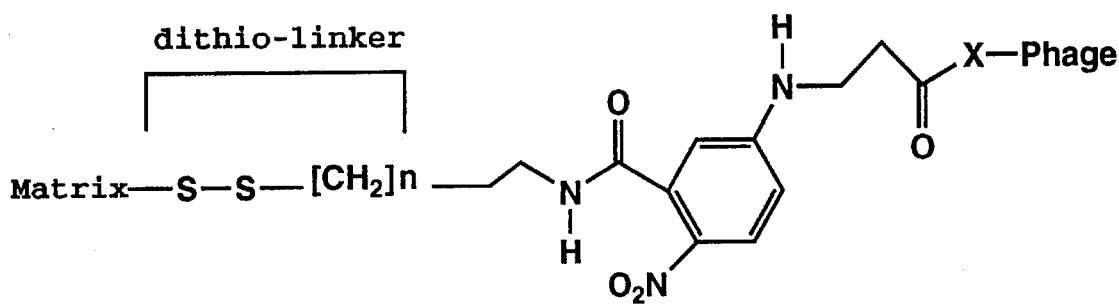
9
FIG. 11

Selection for Glycosidase Activity

Immobilized Suicide Substrate for Selection of RNase
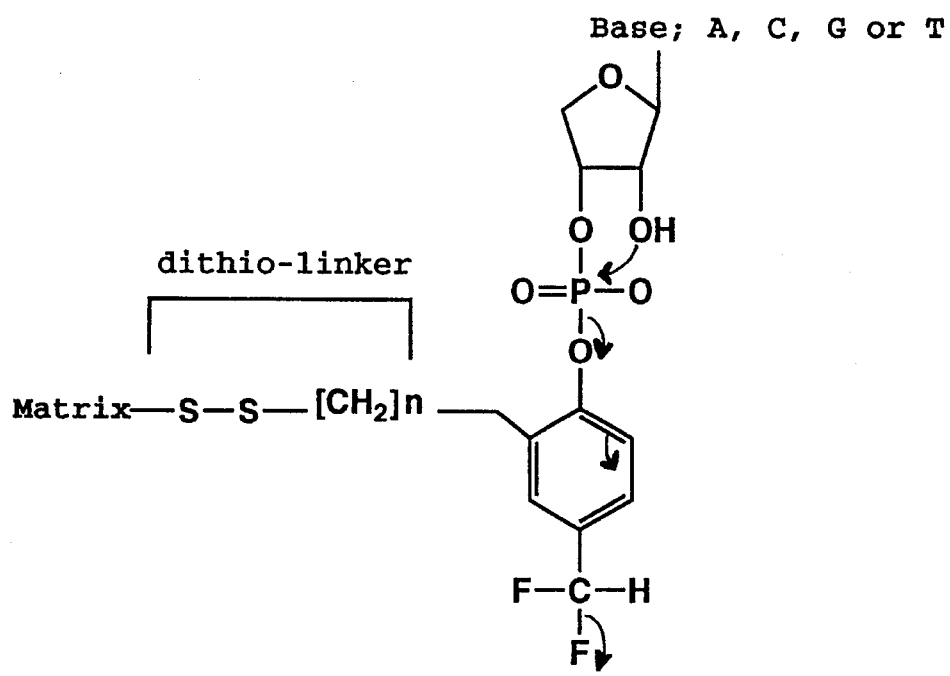
12
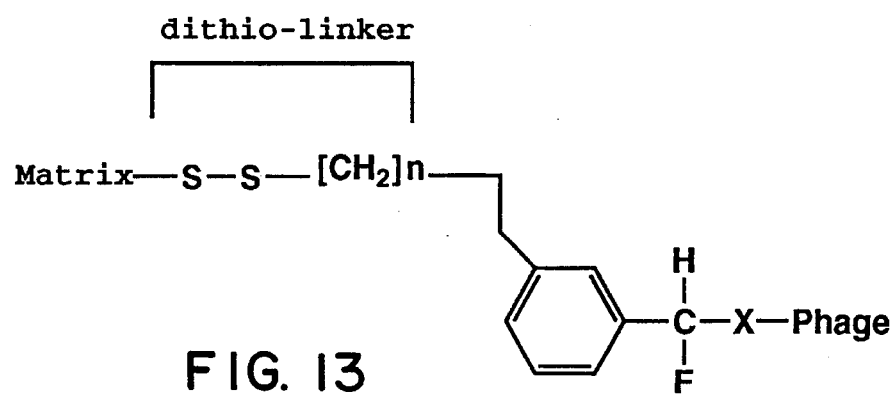
13
FIG. 13

Immobilized Suicide Substrate
For Selection of Proteolytic Activity

SEQUENCE LISTING ( 1 ) GENERAL INFORMATION:

( i i i ) NUMBER OF SEQUENCES: 51

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

GAATTCTAAA CTAGCTAGTC G        2 1

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:2:

ATACTGCTGA CAGTAATACA C 21

( 2 ) INFORMATION FOR SEQ ID NO:3:

( i ) SEQUENCE CHARACTERISTICS:
        ( A ) LENGTH: 57 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:3:

TATTACTGTC AGCAGTATNN KNNKNNKNNK ACTTTCGGCG GAGGGACCAA GGTGGAG 57

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: YES ( x i ) SEQUENCE DESCRIPTION: SEQ ID NO:4:

AATACGACTC ACTATAGGGC G 21

( 2 ) INFORMATION FOR SEQ ID NO:5:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:5:

TATTACTGTC AGCAGTATNN KNNKNNKNNK ACTTTCGGCG GAGGGACC 48

( 2 ) INFORMATION FOR SEQ ID NO:6:

( i ) SEQUENCE CHARACTERISTICS:
        ( A ) LENGTH: 60 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:6:

TATTACTGTC AGCAGTATNN KNNKNNKNNK NNKACTTTCG GCGGAGGGAC CAAGGTGGAG 60

( 2 ) INFORMATION FOR SEQ ID NO:7:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:7:

```
TATTACTGTC AGCAGTATNN KNNKNNKNNK NNKACTTTCG GCGGAGGGAC C         51
```

( 2 ) INFORMATION FOR SEQ ID NO:8:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:8:

```
GATTTTGCAG TGTATTACTG TCAGCAGTAT NNKNNKNNKN NKNNKNNKAC TTTCGGCGGA    60

GGGACCAAGG TGGAG                                                    75
```

( 2 ) INFORMATION FOR SEQ ID NO:9:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:9:

```
TATTACTGTC AGCAGTATNN KNNKNNKNNK NNKNNKACTT TCGGCGGAGG GACC        54
```

( 2 ) INFORMATION FOR SEQ ID NO:10:

( i ) SEQUENCE CHARACTERISTICS:
        ( A ) LENGTH: 75 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:10:

```
GATTTTGCAG TGTATTACTG TNNKNNKNNK NNKNNKNNKN NKNNKNNKNN KTTCGGCGGA    60

GGGACCAAGG TGGAG                                                    75
```

( 2 ) INFORMATION FOR SEQ ID NO:11:

( i ) SEQUENCE CHARACTERISTICS:
        ( A ) LENGTH: 70 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: YES ( x i ) SEQUENCE DESCRIPTION: SEQ ID NO:11:

```
GTTCCACCTT GGTCCCTTGG CCGAAMNNMN NMNNMNNMNN MNNMNNMNNA CAGTAGTACA      60

CTGCAAAATC                                                             70
```

( 2 ) INFORMATION FOR SEQ ID NO:12:

( i ) SEQUENCE CHARACTERISTICS:
        ( A ) LENGTH: 76 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: YES ( x i ) SEQUENCE DESCRIPTION: SEQ ID NO:12:

```
GTTCCACCTT GGTCCCTTGG CCGAAMNNMN NMNNMNNMNN MNNMNNMNNM NNMNNACAGT      60

AGTACACTGC AAAATC                                                     76
```

( 2 ) INFORMATION FOR SEQ ID NO:13:

( i ) SEQUENCE CHARACTERISTICS:
        ( A ) LENGTH: 94 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: YES ( x i ) SEQUENCE DESCRIPTION: SEQ ID NO:13:

```
GTTCCACCTT GGTCCCTTGG CCGAAMNNMN NMNNMNNMNN MNNMNNMNNM NNMNNMNNMN      60

NMNNMNNMNN MNNACAGTAG TACACTGCAA AATC                                 94
```

( 2 ) INFORMATION FOR SEQ ID NO:14:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:14:

TTCGGCCAAG GGACCAAGGT GGAAC 25

(2) INFORMATION FOR SEQ ID NO:15:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:15:

GCAATTAACC CTCACTAAAG GG 22

(2) INFORMATION FOR SEQ ID NO:16:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:16:

TCTCGCACAG TAATACACGG CCGT 24

(2) INFORMATION FOR SEQ ID NO:17:

(i) SEQUENCE CHARACTERISTICS:
        (A) LENGTH: 57 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:17:

GCCGTGTATT ACTGTGCGAG ANNKNNKNNK GACNNKTGGG GCCAAGGGAC CACGGTC 57

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (xi) SEQUENCE DESCRIPTION: SEQ ID NO:18:

TTGATATTCA CAAACGAATG G 21

(2) INFORMATION FOR SEQ ID NO:19:

(i) SEQUENCE CHARACTERISTICS:
    (A) LENGTH: 72 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:19:

```
GCCGTGTATT ACTGTGCGAG AGGTNNKNNK NNKNNKNNKN NKNNKGACNN KTGGGGCCAA    60
GGGACCACGG TC                                                       72
```

(2) INFORMATION FOR SEQ ID NO:20:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:20:

```
GCCGTGTATT ACTGTGCGAG AGGTNNKNNK NNKNNKNNKN NKNNKNNKNN KNNKNNKNNK    60
NNKGACNNKT GGGGCCAAGG GACCACGGTC                                    90
```

(2) INFORMATION FOR SEQ ID NO:21:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:21:

```
GTGTATTATT GTGCGAGANN SNNSNNSNNS NNSTGGGGCC AAGGGACCAC G             51
```

(2) INFORMATION FOR SEQ ID NO:22:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (iv) ANTI-SENSE: NO (xi) SEQUENCE DESCRIPTION: SEQ ID NO:22:

```
GTGTATTATT GTGCGAGANN SNNSNNSNNS NNSNNSNNSN NSNNSNNSTG GGGCCAAGGG    60
ACCACG                                                              66
```

( 2 ) INFORMATION FOR SEQ ID NO:23:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: YES ( i v ) ANTI-SENSE: NO ( x i ) SEQUENCE DESCRIPTION: SEQ ID NO:23:

GTGTATTATT GTGCGAGANN SNNSNNSNNS NNSNNSNNSN NSNNSNNSNN SNNSNNSNNS        60

NNSNNSTGGG GCCAAGGGAC CACG                                              84

( 2 ) INFORMATION FOR SEQ ID NO:24:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:24:

Tyr  Tyr  Cys  Ala  Arg  Gly  Xaa  Xaa  Xaa  Xaa  Xaa  Xaa  Xaa  Xaa  Xaa  Xaa
    1                   5                        10                            15

Xaa  Xaa  Xaa  Asp  Xaa  Trp  Gly  Gln  Gly
                   20                  25

( 2 ) INFORMATION FOR SEQ ID NO:25:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: YES ( x i ) SEQUENCE DESCRIPTION: SEQ ID NO:25:

Tyr  Tyr  Cys  Ala  Arg  Gly  Xaa  Xaa  Xaa  Xaa  Xaa  Xaa  Xaa  Asp  Xaa  Trp
    1                   5                        10                            15

Gly  Gln  Gly ( 2 ) INFORMATION FOR SEQ ID NO:26:

( i ) SEQUENCE CHARACTERISTICS:
        ( A ) LENGTH: 11 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:26:

Gln  Gln  Tyr  Gly  Gly  Ser  Pro  Trp  Phe  Gly  Gln
    1                   5                        10

( 2 ) INFORMATION FOR SEQ ID NO:27:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( i i i ) HYPOTHETICAL: YES ( x i ) SEQUENCE DESCRIPTION: SEQ ID NO:27:

```
Gln Gln Tyr Xaa Xaa Xaa Xaa Xaa Thr Phe Gly Gly
1               5                   10
```

( 2 ) INFORMATION FOR SEQ ID NO:28:

( i ) SEQUENCE CHARACTERISTICS:
    ( A ) LENGTH: 13 amino acids
    ( B ) TYPE: amino acid
    ( D ) TOPOLOGY: linear ( i i ) MOLECULE TYPE: peptide ( i i i ) HYPOTHETICAL: YES ( x i ) SEQUENCE DESCRIPTION: SEQ ID NO:28:

```
Gln Gln Tyr Xaa Xaa Xaa Xaa Xaa Xaa Thr Phe Gly Gly
1               5                       10
```

( 2 ) INFORMATION FOR SEQ ID NO:29:

( i ) SEQUENCE CHARACTERISTICS:
    ( A ) LENGTH: 19 amino acids
    ( B ) TYPE: amino acid
    ( D ) TOPOLOGY: linear ( i i ) MOLECULE TYPE: peptide ( i i i ) HYPOTHETICAL: NO ( x i ) SEQUENCE DESCRIPTION: SEQ ID NO:29:

```
Tyr Tyr Cys Ala Arg Gly Leu Met Arg Ile Leu Ile Thr Asp Val Trp
1               5                   10                  15
Gly Gln Gly
```

( 2 ) INFORMATION FOR SEQ ID NO:30:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: peptide ( i i i ) HYPOTHETICAL: NO ( x i ) SEQUENCE DESCRIPTION: SEQ ID NO:30:

```
Tyr Tyr Cys Ala Arg Gly Val Ala Leu Ser Val Val Trp Val Pro Met
1               5                   10                  15
Gly Ser Ser Asp Phe Trp Gly Gln Gly
            20                  25
```

( 2 ) INFORMATION FOR SEQ ID NO:31:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: peptide ( i i i ) HYPOTHETICAL: NO ( x i ) SEQUENCE DESCRIPTION: SEQ ID NO:31:

Tyr Tyr Cys Ala Arg Gly Ser Arg Ser Gln Val Met Leu Arg Gly Ser
1               5                       10                      15

Ile Val Trp Asp Phe Trp Gly Gln Gly
                20              25

( 2 ) INFORMATION FOR SEQ ID NO:32:

( i ) SEQUENCE CHARACTERISTICS:
    ( A ) LENGTH: 25 amino acids
    ( B ) TYPE: amino acid
    ( D ) TOPOLOGY: linear ( i i ) MOLECULE TYPE: peptide ( i i i ) HYPOTHETICAL: NO ( x i ) SEQUENCE DESCRIPTION: SEQ ID NO:32:

Tyr Tyr Cys Ala Arg Gly Val Tyr Val Pro Val Gly Thr Gly Pro Gln
1               5                       10                      15

Leu Ile His Asp Ala Trp Gly Gln Gly
                20              25

( 2 ) INFORMATION FOR SEQ ID NO:33:

( i ) SEQUENCE CHARACTERISTICS:
    ( A ) LENGTH: 19 amino acids
    ( B ) TYPE: amino acid
    ( D ) TOPOLOGY: linear ( i i ) MOLECULE TYPE: peptide ( i i i ) HYPOTHETICAL: NO ( x i ) SEQUENCE DESCRIPTION: SEQ ID NO:33:

Tyr Tyr Cys Ala Arg Gly Gly Arg Asp Glu Phe Gly Cys Asp Tyr Trp
1               5                       10                      15

Gly Gln Gly ( 2 ) INFORMATION FOR SEQ ID NO:34:

( i ) SEQUENCE CHARACTERISTICS:
    ( A ) LENGTH: 19 amino acids
    ( B ) TYPE: amino acid
    ( D ) TOPOLOGY: linear ( i i ) MOLECULE TYPE: peptide ( i i i ) HYPOTHETICAL: NO ( x i ) SEQUENCE DESCRIPTION: SEQ ID NO:34:

Tyr Tyr Cys Ala Arg Gly Val Gly Val Arg Arg Gln Gly Asp Pro Trp
1               5                       10                      15

Gly Gln Gly ( 2 ) INFORMATION FOR SEQ ID NO:35:

( i ) SEQUENCE CHARACTERISTICS:
    ( A ) LENGTH: 19 amino acids
    ( B ) TYPE: amino acid
    ( D ) TOPOLOGY: linear ( i i ) MOLECULE TYPE: peptide ( i i i ) HYPOTHETICAL: NO ( x i ) SEQUENCE DESCRIPTION: SEQ ID NO:35:

Tyr Tyr Cys Ala Arg Gly Arg Arg Ile Thr Ala Arg Leu Asp Gly Trp
1               5                   10                  15

Gly Gln Gly ( 2 ) INFORMATION FOR SEQ ID NO:36:

( i ) SEQUENCE CHARACTERISTICS:
      ( A ) LENGTH: 19 amino acids
      ( B ) TYPE: amino acid
      ( D ) TOPOLOGY: linear ( i i ) MOLECULE TYPE: peptide ( i i i ) HYPOTHETICAL: NO ( x i ) SEQUENCE DESCRIPTION: SEQ ID NO:36:

Tyr Tyr Cys Ala Arg Gly Ile Tyr Gln Cys Thr Lys Ala Asp Pro Trp
1               5                   10                  15

Gly Gln Gly ( 2 ) INFORMATION FOR SEQ ID NO:37:

( i ) SEQUENCE CHARACTERISTICS:
      ( A ) LENGTH: 19 amino acids
      ( B ) TYPE: amino acid
      ( D ) TOPOLOGY: linear ( i i ) MOLECULE TYPE: peptide ( i i i ) HYPOTHETICAL: NO ( x i ) SEQUENCE DESCRIPTION: SEQ ID NO:37:

Tyr Tyr Cys Ala Arg Gly Met Val Leu Lys Ser Gly Lys Asp Phe Trp
1               5                   10                  15

Gly Gln Gly ( 2 ) INFORMATION FOR SEQ ID NO:38:

( i ) SEQUENCE CHARACTERISTICS:
      ( A ) LENGTH: 13 amino acids
      ( B ) TYPE: amino acid
      ( D ) TOPOLOGY: linear ( i i ) MOLECULE TYPE: peptide ( i i i ) HYPOTHETICAL: NO ( x i ) SEQUENCE DESCRIPTION: SEQ ID NO:38:

Gln Gln Tyr Lys Arg Gly Leu Leu Ser Thr Phe Gly Gly
1               5                   10

( 2 ) INFORMATION FOR SEQ ID NO:39:

( i ) SEQUENCE CHARACTERISTICS:
      ( A ) LENGTH: 13 amino acids
      ( B ) TYPE: amino acid
      ( D ) TOPOLOGY: linear ( i i ) MOLECULE TYPE: peptide ( i i i ) HYPOTHETICAL: NO ( x i ) SEQUENCE DESCRIPTION: SEQ ID NO:39:

Gln Gln Tyr Arg Met Gly Gly Ala Gly Thr Phe Gly Gly
1               5                   10

( 2 ) INFORMATION FOR SEQ ID NO:40:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:40:

```
Gln Gln Tyr Gln Arg Met Ser Trp Leu Thr Pro Gly Gly
1               5                   10
```

( 2 ) INFORMATION FOR SEQ ID NO:41:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:41:

```
Gln Gln Tyr Arg Ala Ala Lys Trp Asn Thr Pro Gly Gly
1               5                   10
```

( 2 ) INFORMATION FOR SEQ ID NO:42:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:42:

```
Tyr Tyr Cys Ala Arg Gly Arg Asp Ser Phe Ser Gly Leu Val Gly Ala
1               5                   10                  15
Gln Leu Gln Asp Asp Trp Gly Gln Gly
                20              25
```

( 2 ) INFORMATION FOR SEQ ID NO:43:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:43:

```
Tyr Tyr Cys Ala Arg Gly Ser Gly Leu Leu Thr Phe Trp Ala Ser Met
1               5                   10                  15
Leu Pro Asp Asp Arg Trp Gly Gln Gly
                20              25
```

( 2 ) INFORMATION FOR SEQ ID NO:44:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:44:

```
Tyr  Tyr  Cys  Ala  Arg  Gly  Gly  Ser  Gln  Met  Trp  Cys  Gln  Asp  Lys  Trp
1              5                        10                       15
Gly  Gln  Gly
```

( 2 ) INFORMATION FOR SEQ ID NO:45:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:45:

```
Tyr  Tyr  Cys  Ala  Arg  Gly  Leu  Tyr  Ser  Thr  Tyr  Trp  Phe  Trp  Phe  Thr
1              5                        10                       15
Gln  Ser  Gly  Asp  Gly  Trp  Gly  Gln  Gly
              20                  25
```

( 2 ) INFORMATION FOR SEQ ID NO:46:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:46:

```
Tyr  Tyr  Cys  Ala  Arg  Gly  Val  Asn  Val  Thr  Phe  Gly  Phe  Ser  Arg  Arg
1              5                        10                       15
Ser  Gln  Leu  Asp  Trp  Trp  Gly  Gln  Gly
              20                  25
```

( 2 ) INFORMATION FOR SEQ ID NO:47:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:47:

```
Tyr  Tyr  Cys  Ala  Arg  Gly  Val  Gly  Met  Asn  Phe  Val  Arg  Trp  Gly  Trp
1              5                        10                       15
Asn  Gly  Arg  Asp  Val  Trp  Gly  Gln  Gly
              20                  25
```

( 2 ) INFORMATION FOR SEQ ID NO:48:

( i ) SEQUENCE CHARACTERISTICS:
        ( A ) LENGTH: 19 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:48:

Tyr Tyr Cys Ala Arg Gly Ser Pro Phe Thr Arg Pro Cys Asp Lys Trp
1               5                   10                  15

Gly Gln Gly ( 2 ) INFORMATION FOR SEQ ID NO:49:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:49:

Tyr Tyr Cys Ala Arg Cys His Leu Asp Asp Trp Gly Gln Gly
1               5                   10

( 2 ) INFORMATION FOR SEQ ID NO:50:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:50:

Gln Gln Tyr Thr Thr Thr Met Glu Val Thr Phe Gly Gly
1               5                   10

( 2 ) INFORMATION FOR SEQ ID NO:51:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( i i i ) HYPOTHETICAL: NO ( x i ) SEQUENCE DESCRIPTION: SEQ ID NO:51:

Gln Gln Tyr Gly Gln Ala Ser Ala Thr Phe Gly Gly
1               5                   10

1

CHEMICAL EVENT SELECTION BY SUICIDE SUBSTRATE CONJUGATES

STATEMENT OF GOVERNMENT RIGHTS

Development of the invention disclosed herein was supported by grant number GM-43858 from the National Institutes of Health. The United States government may have certain rights in this invention.

FIELD OF INVENTION

The invention relates to methodologies for panning combinatorial libraries, including synthetic and semisynthetic combinatorial libraries displayed on phagemids. More particularly, the invention relates to the use of suicide substrates for identifying library elements having covalent catalytic activity.

BACKGROUND OF THE INVENTION

Catalytic antibodies are antibodies having catalytic activity. Catalytic antibodies may be generated via immunogenesis by immunizing an immune responsive animal with haptens designed as enzyme substrate analogs.

The efficiency of immunogenesis of catalytic antibodies depends in part upon the design of the enzyme substrate analog. Successful generation of catalytic antibodies depends upon an ability to anticipate the mechanism of a chemical reaction. Antibody catalysis employs the energy with which the substrate binds the antibody to lower activation barriers along the reaction coordinate (Lerner, R. A. et al., *Science* 1991, 252, p. 659–667). Such catalysis depends upon a correct assumption of mechanistic details, i.e., the extent to which the hapten embodies critical features of the rate-determining transition state, and the manner in which the immune system responds to the antigen. Enzymes generate large rate enhancements through the subtle interplay of many favorable binding interactions refined through the process of evolution. Therefore, one way antibody catalysis could be made even more powerful is by similarly harnessing the diversity of the immune response to control the nature and position of amino acid residues in the active site.

Two conventional strategies are employed for designing haptens employable as enzyme substrate analogs, viz.:
1. A strategy employing haptenic analogs of the substrate transition state; and
2. A strategy employing a hapten within a bait and switch strategy.

Conventionally, the designed hapten is employed both to generate the catalytic antibody by administration to an immune responsive animal and to screen the antibody producing hybridomas derived from splenocytes taken from such immune responsive animal.

When haptenic transition state analogs are employed in the screening process, the resultant catalytic antibody is necessarily limited to those antibody which also have binding activity with respect to the haptenic transition state analog. Catalytic antibodies having low avidity or no avidity for the haptenic transition state analog are lost during this screening process. There is reason to believe that such loss may be significant.

If bait and switch haptens are employed, it is difficult to control the location of the charge on the resultant antibody.

An alternative method for obtaining catalytic antibodies and catalytically active proteins employs semisynthetic combinatorial antibody libraries. In this instance the library is generated in vitro and not in vivo. A preferred semisynthetic combinatorial library employs phage displayed antibodies or proteins, i.e., phagemids. This methodology allows selection for desired functionalities within antibody combining sites because large numbers of different proteins are displayed on a phage format thus linking recognition and replication. Phagemid displayed semisynthetic combinatorial libraries are disclosed by Burton, D. R. (*Acc. Chem. Res.* 1993, 26, p. 405–411), Barbas III, C. F. et al. (*Proc. Natl. Acad. Sci. U.S.A.* 1992, 89, p. 4457–4461) and Lerner, R. A. et al. (*Science* 1992, 258, p. 1313–1314). In this way, a single antibody which carries out a chemical reaction can be identified and replicated so long as the chemical event distinguishes the phage-bearing antibody from the rest of the population.

Panning procedures employed for screening antibodies produced by immunogenesis can also be employed for screening semisynthetic antibody libraries displayed on phagemids. Accordingly, binding assays employing substrate transition state analogs and screening protocols employing the bait and switch methodology may be employed for panning antibody libraries displayed on phagemids. However, the limitations of these panning procedures are carried over to the phagemid technology, i.e., many catalytically active antibodies within the phagemid library fail to be identified during the panning process due to low binding affinity with respect to a haptenic substrate analog or due to a failure of the bait and switch methodology.

A major distinction between an immunogenically generated library and a semisynthetic phagemid library is that the semisynthetic phagemid library does not require the use of a hapten. What is needed is a panning methodology employable with semisynthetic phagemid libraries which exploits this difference and which identifies catalytic antibody or catalytic proteins lost by conventional panning protocols.

DEFINITIONS

The terms suicide substrate, mechanism-based inhibitor and affinity label are used interchangeably throughout the text. A suicide substrate is a relatively unreactive compound, having a structural similarity to the substrate or product for a particular enzyme, that via its normal catalytic mechanism of action, converts the inactivator molecule into a species which without prior release from the active site, binds covalently to that enzyme, thereby inactivating it; universal chymotrypsin-like serine protease domains; Silverman, R. B. (1988) *Mechanism-Based Enzyme Inactivation: Chemistry and Enzymology*, Vol. 1 and Vol. 2 (CRC Press, Inc., Boca Raton, Fla.). The terms panning or affinity selection are used interchangeably throughout the text.

SUMMARY

The invention is directed to methods for producing catalytically active molecules having covalent catalytic activity. In covalent catalysis, the substrate is transiently modified by the formation of a covalent bond with the catalyst to give a reactive intermediate. Nucleophilic catalysis is an example of covalent catalysis. Suicide substrates or mechanism-based enzyme inactivators are relatively unreactive compounds which have structural similarity to substrates of enzymes having covalent catalysis activity and which are activated by such enzymes, via the normal catalytic mechanism of action. Such activation converts the suicide substrate to a species which, without prior release from the active site, binds covalently to such enzyme. This is distinct from earlier panning procedures which rely upon noncovalent binding between antibody and ligand as the primary screen for catalytic activity.

The method of the invention can be employed for panning any molecular library. However, it is particularly well suited for panning synthetic and semisynthetic protein, antibody, and antibody fragment libraries displayed on phagemids which encode their displayed protein, antibody, or antibody fragment. Use of panning procedures employing suicide substrates allow for the selection of catalytic mechanism, viz., if a covalent linkage is formed between the protein, antibody, or antibody fragment and the support-bound suicide substrate, then it is presumed that the selected-for chemistry has occurred.

In its broadest mode, the invention is directed to a method for producing polymeric catalysts having covalent catalytic activity for transforming substrate into product and having a reactivity for forming a covalent conjugate between the catalyst and the suicide substrate. The method employs four broad steps. In the first step, a library of polymeric molecules is contacted with the suicide substrate under conditions for forming the covalent catalyst/suicide substrate conjugate. In the preferred mode of the invention, the library of polymeric molecules is comprised of synthetic or semisynthetic proteins, antibodies, or antibody fragments. Also in the preferred mode, the covalent catalyst/suicide substrate conjugate is immobilized on a solid phase. The covalent catalyst/suicide substrate conjugate is then isolated by separation from such library, e.g., by means of a stringent wash. In an alternative mode of the invention, if numerous covalent catalyst/suicide substrate conjugates are isolated, the collection of conjugates may be employed for making an enriched library. This enriched library may then be screened again with the suicide substrate. This process may be repeated as often as desired. After obtaining a workable number of covalent catalyst/suicide substrate conjugates, the covalent catalytic activity of the corresponding polymeric catalysts may be assayed with respect to their ability to catalyze the desired transformation of substrate into product. In the preferred mode, the polymeric catalysts are catalytically active proteins, antibodies, or antibody fragments displayed on phagemids. The polymeric catalysts are identified and generated by isolation and expansion of nucleotide sequences encoded within such phagemids. Polymeric catalysts identified by the catalytic assay as having the desired catalytic activity may then be produced as desired.

In another preferred mode, the library employed in the above process is a combinatorial library of synthetic or semisynthetic proteins enriched with respect to nucleophilic amino acid substitutions. Nucleophilic amino acids are required within the active cite of covalent catalytic proteins. Preferred nucleophilic amino acids include Asp, Cys, Glu, His, Lys, Ser, Thr, and Tyr.

An alternative aspect of the invention is directed to a chemical complex employed in the above described panning protocol. This chemical complex includes a solid phase, a suicide substrate covalently linked to the solid phase, a catalytically active protein covalently linked to the suicide substrate for forming a covalent protein/suicide substrate conjugate, and a chemically encoded molecular tag linked to the catalytically active protein for identifying the catalytically active protein. The catalytically active protein, when not covalently linked to the suicide substrate, has a covalent catalytic activity. In an alternative aspect of the invention, the catalytically active protein within the chemical complex is displayed on a phagemid having a nucleotide sequence encoding the synthetic or semisynthetic protein displayed thereon while the phagemid displayed protein library is immobilized on a solid phase.

Another aspect of the invention is directed to phagemid displayed synthetic or semisynthetic protein libraries enriched with respect to nucleophilic substitutions selected from the group consisting of Asp, Cys, Glu, His, Lys, Ser, Thr, and Tyr.

A particular mode of the invention is directed to the selection of catalytic antibodies having esterolytic activity. The chemical event selection procedure for this mode of the invention employs a suicide substrate for panning for catalytic antibody having an activated cysteine thiol as the catalytic nucleophile. Two out of ten combinatorial phage contained an unpaired cysteine in the antibody heavy chain.

The invention also encompasses several other modes imparting broad applicability to the invention. Catalysts exhibiting a variety of different mechanisms can be obtained, e.g., catalytic antibodies having β-lactamase activity and glycosidase activity can be panned using known suicide substrates. Additionally catalytically active antibodies having aldolase activity for catalyzing carbon-carbon bond formation can be panned using known suicide substrates. Further suicide substrates are known for probing reactions involving protonation-deprotonation, addition-elimination, acylation, phosphorylation, isomerization, decarboxylation, oxidation, and polymerization. Furthermore, the method of the invention may be employed for panning RNA-based catalytic molecules.

BRIEF DESCRIPTION OF THE DRAWINGS

FIG. 1 illustrates structures and numerical assignments of compounds 1, 16, and 17.

FIG. 2 is a table illustrating the heavy and light chain CDR3 amino acid residue sequences of selected clones screened with compounds 1, 16, and 17 as shown in FIG. 1.

FIG. 3 illustrates a scheme showing the conjugation of compound 1 onto BSA to form compound 2.

FIG. 4 illustrates the immobilized BSA/suicide substrate conjugate to form compound 3.

FIG. 5 illustrates compounds employed in example 7.

FIG. 7. (A) illustrates the time course for complete disulfide interchange of Fab 32-7 with Ellman's reagent. The reaction was followed by measuring the release of 3-carboxy-4-nitro-thiophenol with a stopped-flow spectrophotometer. The conditions were 100 mM MOPS, 0.5 mM EDTA, pH 7.4, 10% total cosolvent (8% DMF, 2% dioxane) in the presence of approximate final concentrations of 2 μM antibody and 200 μM Ellman's reagent. The absorbance change corresponds to 1 μM and proceeds with k=0.020 s$^{-1}$.

FIG. 7 (B) illustrates a typical progress curve for the liberation of thiopyridone during the reaction of Fab 32-7 with ester 105. The conditions were similar to those in (A) using 12 μM antibody and 200 μM 105. The data was fitted by an expression of the form $[P]=At-B(1-e^{-kt})$ to evaluate k according to the method disclosed by Gutfreund, H. et al. (*Biochem. J.* 1956, 63, p. 656–661). The dotted line extrapolates to the y-intercept "burst" formation of 7 μM thiopyridone.

FIG. 11 illustrates immobilized suicide substrates employed for the selection of β-lactamase activity.

FIG. 13 illustrates immobilized suicide substrates employed for the selection of RNase activity.

DETAILED DESCRIPTION

Figure 6:
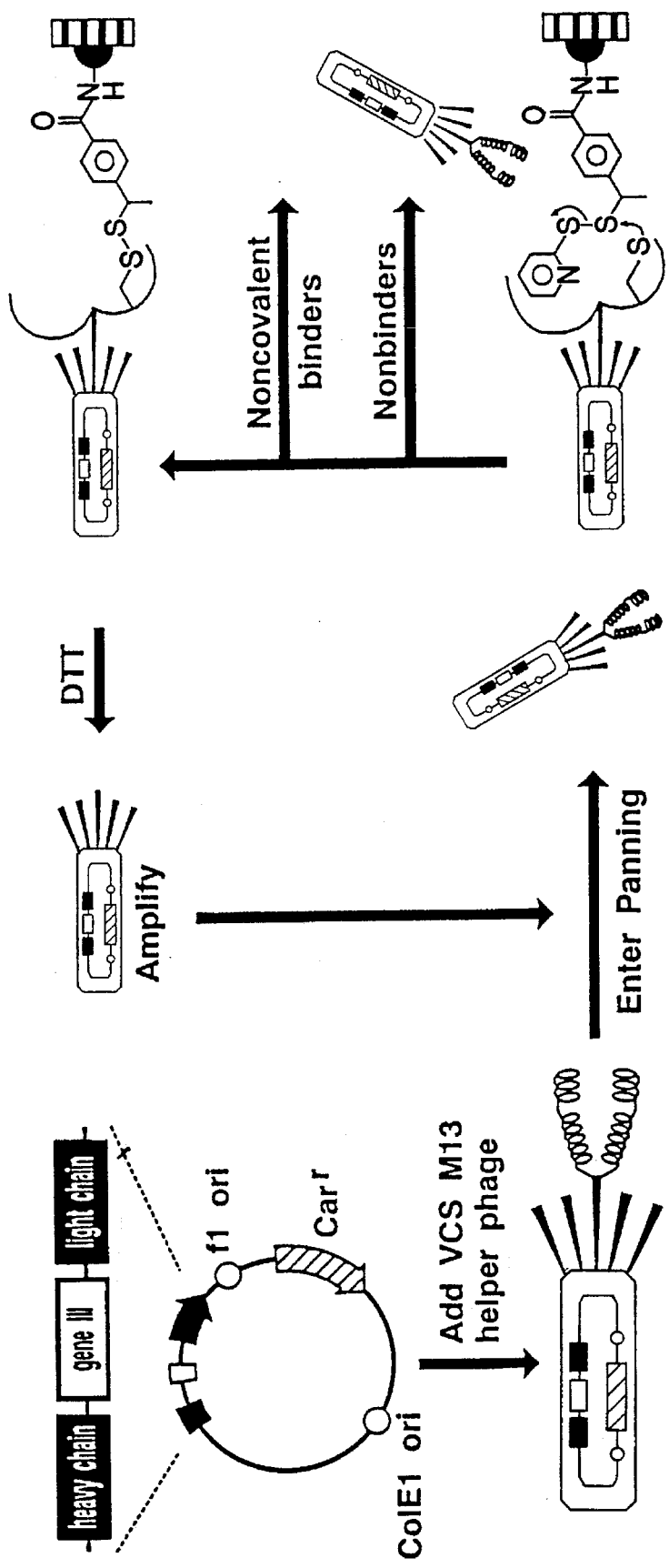
FIG. 6 illustrates a scheme showing the phage-display of Fab fragments to select for antibody combining sites containing an unpaired cysteine.

Semisynthetic combinatorial antibody library methodology in the phage-display format was used to select for a cysteine residue in complementarity determining regions. Libraries were panned with an α-phenethyl pyridyl disulfide which undergoes disulfide interchange. Out of ten randomly picked clones, two contained an unpaired cysteine, one of which was studied. The antibody catalyzed the hydrolysis of the corresponding thioester where the electrophilic carbonyl occupies the three-dimensional space which was defined by the reactive sulfur atom during selection. The reaction operates by covalent catalysis. While the steady-state rate enhancement relative to the activated thiol ester substrate is modest, hydrolysis of the acylated cysteine intermediate is remarkably efficient with a catalytic advantage of about four orders of magnitude. The results suggest that iterative mechanism-based selection procedures can recapitulate the enzymatic mechanisms refined through evolution.

SELECTION PROCEDURE FOR CYSTEINE RESIDUES

All microtiter plates used in the panning procedure were prepared as follows: The hapten-BSA conjugate (compound 1 is available from Pierce) was diluted to 0.1 μg/ml and 25 μl added to each well. The plates were incubated at 37° C. overnight. The dried plates were fixed by adding 50 μl of methanol to each well. After 5 min, the methanol was discarded and the plate dried at room temperature. After blocking with PBS (phosphate-buffered saline; 10 mM sodium phosphate, 150 mM NaCl, pH 7.4)/1% BSA at 37° C. for 30 min, the plates were ready for panning. In the first round of panning, each library was added into six different wells and incubated at 37° C. for 2 hours. The phage solution was discarded, 100 μl of washing buffer TBS (tris-buffered saline; 50 mM tris base, 150 mM NaCl, pH 7.5)/ 0.5% Tween, 1% BSA was added into each well and incubated at 25° C. for 5 min. These wells were washed with 100 μl of water, 100 μl of acid solution (0.1M HCl, pH 2.2, adjusted with glycine) and then water again. The bound phage were eluted with 2×50 μl of 20 mM DTT. The elutions from each library were combined together and used to infect 10 ml of *E. coli* cells. After 15 min at 25° C., 1 μl of infected cell culture was diluted to $10^3$, $10^6$, and $10^8$ with superbroth and then 1 μl of each dilution was plated on a LB (Luria-Bertani) plate/carbenicillin to titer the output. Carbenicillin (20 μg/ml) was added to the cell culture and shaken at 37° C. for 1 hour. The concentration of antibiotic was increased to 50 μg/ml and shaken at 37° C. for another one hour. The cell culture was diluted into 100 ml superbroth which contained 50 μg/ml carbenicillin, 10 μg/ml tetracycline, and $10^{12}$ pfu of VCS M13 helper phage. After shaking 2 hours at 37° C., kanamycin was added (70 μg/ml) and shaken at 37° C. overnight. The cells were removed by centrifugation and PEG (4%) and NaCl (3%) were added to the supernatant. After 30 min on ice, the phage particles were centrifuged. (9000 rpm, 30 min, 4° C.) The phage were resuspended with TBS/1% BSA and clarified by centrifugation. (14,000 rpm, 10 min, 4° C.) The phage solution was ready for further panning. For the next 4 rounds of panning, the washing procedures were modified as follows: second round (2 ×washing buffer, 1×acid solution); third round (5×washing buffer, 1×acid solution for 5 min); fourth round (10×washing buffer/3% BSA, 2×acid solution for 5 min); fifth round (10×washing buffer/3% BSA, 2×acid solution for 5 min). For each round, the bound phage were eluted with 2×20 mM DTT for 5 min. The eluted phage were titered and amplified as described above. After the fifth round of panning, the phagemid DNA was purified, digested with SpeI and NheI and purified on argarose gel to remove the DNA of gene III. The 4.7 kb fragment was electroeluted, religated and transformed into *E. coli*. The colonies were picked up and grown until the $OD_{600}$=0.8, 1 mM isopropyl β-D-thiogalactopyranoside (IPTG) was added and the culture incubated at 30° C. overnight. The cells were lysed with freeze and thaw cycles between −70° C. and 37° C. in PBS. The supernatant was tested on ELISA plates coated with the hapten. The positive colonies were grown again and the phagemid DNA purified and sequenced.

SEQUENCE ANALYSIS OF ISOLATED CLONES

Both clones were derived from the k10/F library disclosed by Barbas III, C. F. et al. (*Proc. Natl. Acad. Sci. U.S.A.* 1993, 90, p. 6385–6389 and (1993) *Gene*, in press) in which the codons for 8 residues of the heavy chain CDR3 and 6 of the light chain CDR3 had been randomized (bold=randomized position) [32-7: HCDR3/ GGRDEFGCDY (SEQ ID NO33), LCDR3/QQYKRGLLST (SEQ ID NO38); 32-11: HCDR3/ GIYQCTKADP (SEQ ID NO36), LCDR3/ QQYQRMSWLT (SEQ ID NO40)]. Based on probability alone, where the synthesis protocol produces 32 codons (one encoding cysteine) and using an average of 8 for the number of randomized residues, the unselected, naive library should contain 20% of the ~$10^8$ clones with an unpaired cysteine; ($1/32$×($31/32$)$^7$)×8=0.20. Experimentally, sequencing of a small sample population gave a value of 23%. After selection, also approximately 20% of the clones contained cysteine. Other non-cysteine containing phage-Fab which survived the panning process were apparently very tight binding and only released when DTT destroyed the Fab structure. The lack of sequence homology demonstrates the vast diversity available to generate a common binding site. Amino acids are denoted by single-letter codes (Ala, A; Arg, R; Asn, N; Asp, D; Cys, C; Glu, E; Gln, Q; Gly, G; His, H; Ile, I; Leu, L; Lys, K; Met, M; Phe, F; Pro, P; Ser, S; Thr, T; Trp, W; Tyr, Y; and Val, V).

ANTIBODY EXPRESSION AND PURIFICATION

The phagemid DNA was transformed into *E. coli* and grown in 100 ml superbroth with 1% glucose overnight. The cells were spun down, washed with fresh superbroth several times and then resuspended into 10×1 liter batches of superbroth with 50 µg/ml carbenicillin, 20 mM $MgCl_2$. The culture grew at 37° C. until $OD_{600}= 0.8$, then IPTG was added to a final concentration of 2 mM. The induction temperature was dropped to 25° C. overnight. The cells were collected, resuspended into tris-EDTA pH 8.0 and lysed by 1 mg/ml lysozyme and then French press (18,000 psi). An FPLC affinity column was prepared from GammaBind G Sepharose (Pharmacia) and goat anti-human F(ab)'$_2$ IgG (Pierce) as in [E. Harlow, D. Lane, *Antibodies: A Laboratory Manual*. Cold Spring Harbor Laboratory: New York, 1988.]. Two different pH solutions were used for affinity chromatography, A: 0.05M citric acid, 0.5 M NaCl, pH 2.1; B: 0.1M sodium phosphate, 0.5M NaCl, pH 9.2. The column was equilibrated with ten column volumes of 87.2% B (final pH=7.4), then washed with three volumes of 10.8% B (final pH=2.3) and finally equilibrated with 87.2% B. The sample was loaded directly onto the column followed by several column volumes of washing solution until the 280 nm reading returned to baseline, then the pH was dropped by changing the solution to 10.8% B. The eluted fractions were collected, neutralized, concentrated and dialyzed with 100 mM MOPS, 0.5 mM EDTA, pH 7.4. The Fab was further purified on an ion-exchange column (Pharmacia Hi-Trap™ SP) using a gradient salt buffer. The purity of the Fab was confirmed by SDS-PAGE with or without reducing agent and on ELISA. The pure Fab was concentrated and stored in 100 mM MOPS, 0.5 mM EDTA, pH 7.4 at 4° C. The final concentration of Fab was estimated from $OD_{280}$ by using $\epsilon=1.24$ which was estimated from the amino acid sequence $(5700 \times N_{Trp}+1300 \times N_{Tyr})$/molecular weight of Fab).

RADIOLABELING EXPERIMENTS

The radiolabeled compound was prepared from 1 and an ethanolic solution of unlabeled and [$^{14}$C]-methylamine hydrochloride (American Radiolabeled chemicals; sp. act. 55 mCi/mmol). The product was purified by preparative thin layer chromatography ($R_f=0.35$, 75/25 ethyl acetate/hexane) to give 104 in nearly quantitative yield (sp. act. 2.88 mCi/mmol). When labeling Fab, reactions were carried out at room temperature and dialyses at 4° C. (100 mM MOPS, 0.5 mM EDTA, pH 7.4). It was necessary to also count the dialysis membrane because of the small scale involved and the propensity of the protein to adhere to the tubing.

STOPPED-FLOW KINETICS

The reactions were done using a Hi-Tech stopped-flow spectrophotometer; a 0.2 ml cell; 1 cm path length; 0.2 ml stop volume; 412 nm; filter time 33 ms. Syringe 1 was charged with 4 µM 32-7 Fab in the variable pH buffer system (MOPS and Bicine for pH range 7–9) with 10% DMF-dioxane cosolvent. Syringe 2 was charged with 400 µM Ellman's reagent in the same solvent. Using conventional spectrophotometry, only the final 10% of the reaction course of 103 or Ellman's reagent could be recorded.

STEADY-STATE ANTIBODY KINETICS

The reactions were performed in 100 mM MOPS, 0.5 mM EDTA, pH 7.4 or 100 mM Bicine, 0.5 mM EDTA, pH 8.5, 8% DMF (dimethyl formamide)—2% dioxane in the presence of substrate and with or without antibody at 25.0° C. in 0.2 ml (1 cm) cuvettes or in ELISA microtiter plates. The rates were monitored by observing the increase in absorbance at 343 nm (Shimadzu spectrophotometer) or at 340 nm (Molecular Devices ELISA plate reader) due to the formation of thiopyridone. The extinction coefficient of thiopyridone was calibrated on both instruments ($\epsilon=7.50\times 10^{-3}$ $\mu M^{-1} cm^{-1}$ for spectrophotometer, $\epsilon=5.36\times 10^{-3}$ $\mu M^{-1} cm^{-1}$ for plate reader; pH values 7–9). A typical procedure using the spectrophotometer was as follows. The cuvettes were filled with 180 µl of buffer and then the appropriate amounts were removed and replaced with Fab 32-7 stock solution. DMF (16 µl) was added to the cuvette and the solutions were mixed. The absorbance was auto-zeroed and the reaction initiated by the addition of 4 µl of 10 mM substrate in dioxane with mixing. The total time from substrate addition to the start of reaction was ~30 seconds. The ELISA reader reactions were performed in a total of 100 µl. A 90 µl portion of buffer was added into the wells and then an amount of buffer was removed and replaced with Fab 32-7 stock solution. The absorbance at 340 nm was read after adding and mixing 8 µl of DMF. The kinetic mode was initiated after adding 2 µl of substrate. The data was recorded every 30 seconds.

RESULTS AND DISCUSSION

The racemic reagent 1 was coupled to bovine serum albumin (BSA) and used as a probe for cysteine groups in antibody binding sites through the process of disulfide interchange, illustrated in FIG. 1 according to a method disclosed by Brocklehurst, K. (*Methods Enzymol.* 1982, 87, p. 427–469) and by Gilbert, H. F. (*Adv. Enzymol.* 1990, 63, p. 69–172). The bioconjugate 2 was immobilized on microtiter plates and used to pan six separate semisynthetic libraries each containing ~10$^5$ copies each of ~10$^8$ distinct transformants (5,6). These phage displayed Fab fragments containing randomized complementarity determining region 3 (CDR3) sequences in either a heavy chain, a light chain or both. After binding to 2, the phage-Fab were sorted using a series of three separate elutions. The last elution employed dithiothreitol (DTT) to release phage anticipated to be covalently attached through a disulfide bond (FIG. 2). Out of ten clones picked at random, two were shown by sequence analysis of phagemid DNA to have the codon for an unpaired cysteine in the heavy chain CDR3.

One clone, 32-7, was chosen for further investigation. The Fab was over-expressed in *E. coli* and isolated using affinity chromatography followed by ion-exchange chromatography affording a protein fraction which was judged to be greater than 98% pure Fab on inspection of native and denaturing gel analyses. As hoped, Fab 32-7 reacted with compound 103 liberating thiopyridone which could be followed spectrophotometrically according to the method of Grassetti, D. R. et al. (*Arch. Biochem. Biophys.* 1967 119, p. 41–49). Based on the estimated total protein concentration and the molar equivalents of thiopyridone produced, the Fab 32-7 consisted of 50±10% functional Fab. The remainder is likely to be improperly folded Fab structures. The existence of a covalent antibody complex was further substantiated using [$^{14}$C]-104. Radioactive protein was isolated after exhaustive dialysis and contained an amount of label corresponding to the quantity of functional Fab determined spectrophotometrically. As for most enzymes which possess an active cysteine, Fab 32-7 was also prone to disulfide interchange with Ellman's reagent, i.e., 3-carboxy-4-nitrophenyl disulfide (*Arch. Biochem. Biophys.* 1959, 82, 70–77). Under pseudo-first-order conditions at pH 7.4, stopped-flow spectroscopy indicated a half-life for the antibody of 35 seconds (FIG. 3A). Interestingly, this is nearly 30 times slower than the exchange reaction involving free cysteine ($t_{1/2}$= 1.3 s). Kinetic titration using Ellman's reagent provided a $pK_a$ =8.25 for the active site sulfhydryl. This value is reasonable for a cysteine which behaves as an "isolated" thiol rather than as part of an interactive system as disclosed by Ascenzi, P. et al. (*Biochem. Biophys. Acta* 1987, 912, p. 203–210) and by Lewis, S. D. et al. (*Biochemistry* 1976, 15, p. 5009–5017). Remarkably, Fab 32-7 remained stable for months (100 mM MOPS, 0.5 mM EDTA, pH 7.4; 4° C.) with no apparent loss in activity and required no exogenous thiol for activation. The resistance to oxidation, taken together with the kinetic data, suggests the cysteine may be sequestered. Inactive papain, for example, consists of protein with incorrect disulfide bonds or cysteines as sulfinic acids, e.g., Lowe, G. *Tetrahedron* 1976, 32, p. 291–302). Even though the Fab molecule contains five cystine linkages, inherent structural motifs or thermodynamic considerations likely preclude intramolecular disulfide shuffling. A buried cysteine would also make protein-s-s-protein formation difficult.

At this point, the active site is known to contain a nucleophilic thiol poised to react with an electrophile at a position in three-dimensional space defined by the reactive sulfur atom of 103. Hence, the congruent thioester 105, where a carbonyl group supplants this atom, was tested and found to be a substrate for the antibody. In retrospect, the choice of a disulfide for panning is in many ways ideal, not only because of its chemoselectivity for cysteine groups, but also because the reactive sulfur atom has tetrahedral geometry with two lone pairs of electrons. This may help select for combining sites which promote, or at least allow, formation of the tetrahedral intermediate and attract critical hydrogen bonds which may participate during the catalytic event. When the racemic ester 105 was added to varying concentrations of the antibody, burst kinetics indicative of the formation of a covalent intermediate were observed according to the method of Hartley, B. S. et al. (*Biochem. J.* 1954, 56, p. 288–297). An analysis of progress curves (product inhibition was not significant) showed the amplitude of the burst to be proportional to 50±10% of the total antibody concentration comparable with the results using disulfide reagents and suggesting full accumulation of the acyl-antibody (FIG. 7B). The reaction could be completely inhibited with 103 or the thiol labeling reagent methyl methanethiolsulfonate (MMTS) according to the method of Smith, D. J. et al. (*Biochemistry* 1975, 14, p. 766–770). The antibody also utilized 106 (R or S methyl group) as substrates with a rate similar to 105 without demonstrating appreciable stereospecificity. Apparently, binding interactions in the region of the methyl group are not significant. The first-order rate constant for approach to the steady-state was k=0.044 min$^{-1}$. This is ~10$^4$ times slower than reactions of papain with amino acid p-nitrophenyl esters, but similar to guinea pig liver transglutaminase, an enzyme invoking cysteine rather than an imidazolium-thiolate pair, see Folk, J. E. et al. *J. Biol. Chem.* 1967, 242, p. 4329–4333). A less than ideal orientation of the carbonyl carbon relative to the sulfur nucleophile may be responsible for the sluggish acylation of Fab 32-7. The Fab underwent multiple turnovers and the dependence of the initial velocity on substrate concentration followed simple saturating kinetics ($k_{cat}$= 0.030 min$^{-1}$, $K_m$=100 µM; 100 mM MOPS, 0.5 mM EDTA, pH 7.4, 25° C.). This afforded a 30-fold steady-state rate enhancement over the background hydrolysis of 5. The fact that the catalyst turns over at all is encouraging, since an unactivated thiol ester is an extremely stable species under the assay conditions according to Bruice, T. C. et al. (*Bioorganic Mechanisms*, 1966 W.A. Benjamin, Inc., New York, vol. 1, chapter 3) and Morse, B. K. et al. (*J. Am. Chem. Soc.* 1952, 74, p. 416–419). The first order rate constant for spontaneous hydrolysis of thiol esters at physiological pH is ~10$^{-7}$ min$^{-1}$, whereas the value for the activated ester 105 was found to be 1.0×10$^{-3}$ min$^{-1}$ under assay conditions. Interestingly, the antibody slowly catalyzed hydrolysis of the corresponding p-nitrophenyl ester of 105. However, this reaction may take place on the surface of the protein and with non-cysteine residues since it could not be inhibited with MMTS. A priori, it would not have been surprising for the antibody to undergo a stoichiometric reaction with 105 and become inactivated, as disclosed by Pollack, S. J. et al. (*Science* 1988, 242, p. 1038–1040). Evidently, the microenvironment of the active site provides a means, perhaps attributable to the stereoelectronic features of the sulfur atom targeted during selection, to accelerate the hydrolysis of the intermediate. In this regard, it can be estimated that the antibody affords a catalytic advantage of ~10$^4$ relative to the decomposition of an acylated cysteine in solution. Improved catalysis would require more efficient transition-state stabilization for acylation and deacylation or activation of water molecules for the deacylation step. While details remain to be elucidated, the results are consistent with the minimal three-step mechanism of substrate binding, acyl-intermediate formation and breakdown fundamental to cysteine and serine proteases as reported by Fersht, A. (*Enzyme Structure and Mechanism*, 1985 2nd Ed. (W.H. Freeman and Company, New York).

Figure 8:
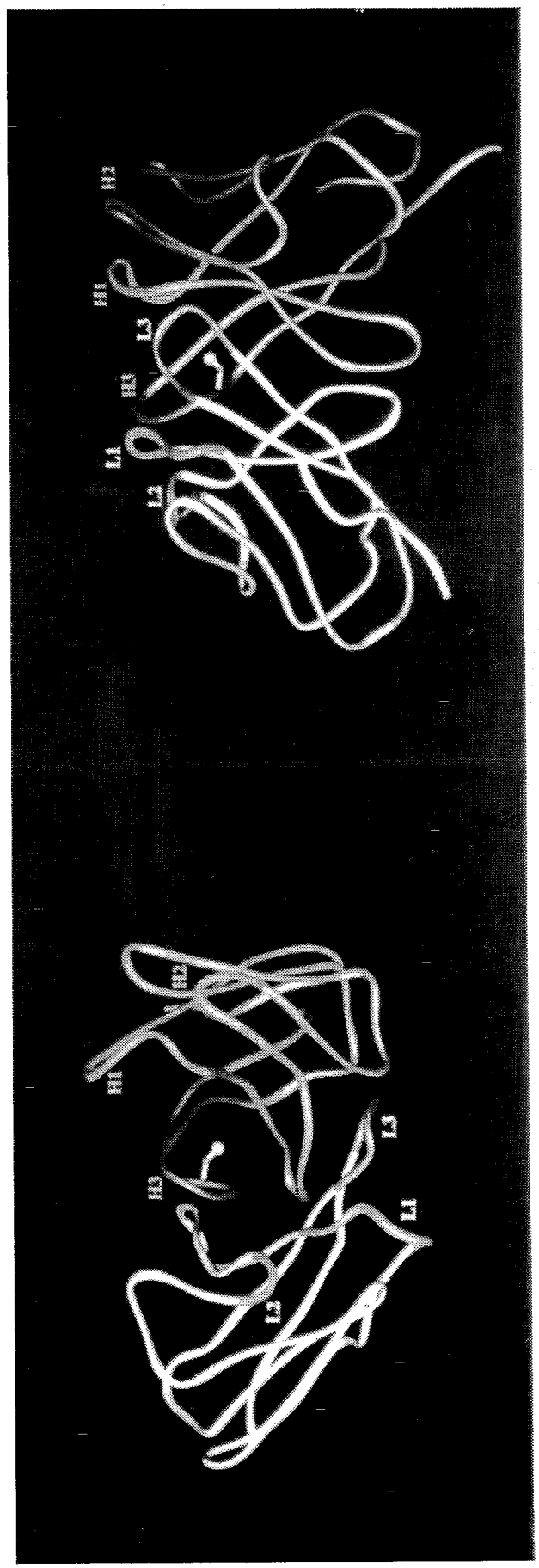
FIG. 8 illustrates a molecular model of the antigen combining region of antibody 32-7. The predicted structure was created by homology modeling according to the method of Chothia, C. et al. (*Nature* 1989, 342, p. 877–883) using the coordinates of the human antibody Fab 3D6 for the $V_L$ (yellow) and $V_H$ (cyan) framework regions, as disclosed by He, X. M. et al. (*Proc. Natl. Acad. Sci. U.S.A.* 1992, 89, p. 7154–7158). The hypervariable loops L1, H2 and H3 were modeled based on the analogous loops from the murine catalytic antibody 1F7, disclosed by Haynes, M. R. et al. (*Science*, 1993 in press), L2 based on the Fab McPC603, disclosed by Satow, Y. et al. (*J. Mol. Biol.* 1986, 190, p. 593–604), H1 from Fab 3D6, and L3 from a conformational loop search. In the predicted structure, the sulfur atom of $Cys^{100B}$ is located approximately 12 Å below the upper rim of a deep groove formed by the hypervariable loops. Although the H3 loop is notoriously difficult to predict, the position and orientation of $Cys^{100B}$ can be compared to the structurally equivalent residue in eight other Fab fragment crystal structures containing 10 H3 residues which reveals an average deviation of only 1.7 Å (0.48–3.4 Å) for the β-C atom.

The approximate position of the cysteine residue can be ascertained using model building by comparison to Fab's of homologous sequence and known structure (FIG. 8). Not surprisingly, the group resides in a deep cleft itself sheltered from the external environment, but accessible to certain molecules. Most important, the model represents a specific binding site featuring a precise arrangement of residues which can orchestrate catalysis. In the present case, one is constrained by the requirement for the concerted interaction between a nonoxidized sulfhydryl, sufficient binding energy to overcome the entropic barrier in orienting the nucleophile and electrophile, and a mechanism for hydrolysis of the acyl-intermediate. The probability of randomly accessing such complexity from the naive pool can be expected to be exceedingly low. Yet, the pressure applied through selection has generated a subpopulation consisting of 1 in 10 members which have the desired catalytic activity. Interestingly, a monoclonal antibody elicited by immunization with a transition-state analog was previously shown to operate through an acyl-intermediate already demonstrating that the interplay between transition-state stabilization and covalent catalysis is within the repertoire of the antibody combining site, as disclosed by Wirsching, P. et al. (*Science* 1991, 252, p. 680–685).

The procedure used here adds to the armamentarium of antibody catalysis in that it allows one to directly select for a chemical event which can be included in the mechanistic plan for the reaction to be catalyzed. Mechanism-based inhibitors have been used in enzymology to inhibit enzymes where a mechanism is known or to give evidence for a mechanism proposed by Silverman, R. B. (*Mechanism-Based Enzyme Inactivation: Chemistry and Enzymology* 1988, Vol. 1 and Vol. 2 (CRC Press, Inc., Boca Raton, Fla.). In one sense, the compound we used to select our antibodies can be considered a mechanism-based inhibitor, but here the process has been reversed, and instead of probing a catalytic mechanism it has been used to select for a molecule exhibiting a mechanism from an otherwise random system. In principle, any mechanism-based inhibitor can be used to select for at least part of a chemical mechanism. The mechanism can be refined and evolved by iterative procedures of selection using transition-state analogs or other inhibitors to add various nucleophiles, general acids, or bases to improve catalysis. At each iteration, the union between chemistry and combinatorial selection serves as a powerful tool for defining the three-dimensional space of the active site. The two chain nature of the antibody molecule should be a further advantage because each chain can bring different functionalities into the active site. The order of the selective steps employed in such an iterative procedure is probably important and it would seem best to begin with a transition-state analog in order to give the selection process at the outset the maximum benefit of chemical insight.

Finally, a significant feature of the present experiment deserves emphasis in that it may shed light on the evolution of catalytic mechanisms. Although there was no direct selection for catalysis initially, the active site when selected for a simple chemical transformation had a specificity which allowed catalysis with appropriate substrates. This may be a general principle where one chemical event may be accompanied by additional chemistry of sufficient utility to afford the catalyst a selectable advantage.

EXAMPLES

The following examples relating to this invention are illustrative and should not, of course, be construed as specifically limiting the invention. Moreover, such variations of the invention, now known or later developed, which would be within the purview of one skilled in the art are to be considered to fall within the scope of the present invention hereinafter claimed.

1. Production of Phagemid-Displayed Fab Heavy and Light Chain Heterodimers that Covalently Bind to Synthetic Suicide Substrate Conjugates In practicing this invention to obtain expression of Fab antibodies having anti-suicide substrate conjugate binding sites, the Fabs of which are expressed on a phage surface, the heavy (Fd consisting of $V_H$ and $C_H1$) and light (kappa) chains ($V_L$, $C_L$) of antibodies are first targeted to the periplasm of *E. coli* for the assembly of heterodimeric Fab molecules. In this system, the first cistron encodes a periplasmic secretion signal (pelB leader) operatively linked to the fusion protein, Fd-cpIII. The second cistron encodes a second pelB leader operatively linked to a kappa light chain. The presence of the pelB leader facilitates the coordinated but separate secretion of both the fusion protein containing the native as well as semisynthetic binding site and light chain from the bacterial cytoplasm into the periplasmic space.

In this process, each chain is delivered to the periplasmic space by the pelB leader sequence, which is subsequently cleaved. The heavy chain is anchored in the membrane by the cpIII membrane anchor domain while the light chain is secreted into the periplasm. Fab molecules are formed from the binding of the heavy chain with the soluble light chains.

In addition, the expression vectors used in this invention allow for the production of soluble Fab heterodimers as described in Example 4C.

A. Preparation of a Dicistronic Expression Vector, pComb3, Capable of Expressing a Phagemid Fab Display Protein The pComb3 phagemid expression vector of this invention is used in expressing the anti-suicide substrate conjugate antibodies. The antibody Fd chain comprising variable ($V_H$) and constant ($C_H1$) domains of the heavy chain are fused with the C-terminal domain of bacteriophage gene III (3) coat protein. Gene III of filamentous phage encodes a 406-residue minor phage coat protein, cpIII (cp3), which is expressed prior to extrusion in the phage assembly process on a bacterial membrane and accumulates on the inner membrane facing into the periplasm of *E. coli*.

The phagemid vector, designated pComb3, allows for both surface display and soluble forms of Fabs. The vector originally had been designed for the cloning of combinatorial Fab libraries; Barbas et al., *Methods, A Companion to Methods in Enzymology*, 2:119–124 (1991), the disclosure of which is hereby incorporated by reference.

The Xho I and Spe I sites are provided for cloning complete PCR-amplified heavy chain (Fd) sequences. An Aat II restriction site is also present that allows for the insertion of Xho I/Aat II digests of the PCR products. The Sac I and Xba I sites are provided for cloning PCR amplified antibody light chains of this invention. The cloning sites are compatible with previously reported mouse and human PCR primers; Huse et al., *Science*, 246:1275–1281 (1989) and, Persson et al., *Proc. Natl. Acad. Sci., U.S.A.*, 88:2432–2436 (1991). The nucleotide sequence of the pelB, a leader sequence for directing the expressed protein to the periplasmic space, is as reported by Huse et al., supra.

The vector contains a ribosome binding site; Shine et al., *Nature*, 254:34 (1975). The sequence of the phagemid vector, pBluescript, which includes ColE1 and F1 origins and a beta-lactamase gene, is described; Short et al., *Nuc. Acids Res.*, 16:7583–7600 (1988), and has the GenBank Accession Number 52330 for the complete sequence. Additional restriction sites, Sal I, Acc I, Hinc II, Cla I, Hind III, Eco RV, Pst I and Sma I, located between the Xho I and Spe I sites of the empty vector are derived from a 51 base pair stuffer fragment of pBluescript; Short et al., supra. A nucleotide sequence that encodes a flexible 5 amino acid residue tether sequence which lacks an ordered secondary structure is juxtaposed between the Fab and cp3 nucleotide domains so that interaction in the expressed fusion protein is minimized.

Thus, the resultant combinatorial vector, pComb3, consists of a DNA molecule having two cassettes to express one fusion protein, Fd/cp3, and one soluble protein, the light chain. The vector also contains nucleotide residue sequences for the following operatively linked elements listed in a 5' to 3' direction: a first cassette consisting of LacZ promoter/ operator sequences; a Not I restriction site; a ribosome binding site; a pelB leader; a spacer region; a cloning region bordered by 5' Xho and 3' Spe I restriction sites; the tether sequence; the sequences encoding bacteriophage cp3 followed by a stop codon; a Nhe I restriction site located between the two cassettes; a second lacZ promoter/operator sequence followed by an expression control ribosome binding site; a pelB leader; a spacer region; a cloning region bordered by 5' Sac I and a 3' Xba I restriction sites followed by expression control stop sequences and a second Not I restriction site.

In the above expression vector, the Fd/cp3 fusion and light chain proteins are under the control of separate lac promoter/ operator sequences and directed to the periplasmic space by pelB leader sequences for functional assembly on the membrane. Inclusion of the phage F1 intergenic region in the vector allows for the packaging of single-stranded phagemid with the aid of helper phage. The use of helper phage superinfection allows for the expression of two forms of cp3. Consequently, normal phage morphogenesis is perturbed by competition between the Fd/cp3 fusion and the native cp3 of the helper phage for incorporation into the virion. The resulting packaged phagemid carries native cp3, which is necessary for infection, and the encoded Fab fusion protein, which is displayed for selection. Fusion with the C-terminal domain is necessitated by the phagemid approach because fusion with the infective N-terminal domain will render the host cell resistant to infection.

The pComb3 expression vector described above forms the basic construct of the Fab display phagemid expression vectors described below, and used in this invention for the production of human anti-suicide substrate conjugate Fab antibodies. The surface display phagemid expression vector, pC3AP313, was deposited with ATCC on Feb. 2, 1993 for use in this invention. The deposited vector has been assigned the ATCC Accession Number 75408. The pC3AP313 expression vector contains the bacteriophage gene III and heavy and light chain variable domain sequences for encoding human Fab antibodies against tetanus toxoid. The reading frame of the nucleotide sequences for translation into amino acid residue sequences begins at nucleotide position 1 for both the light and heavy chain variable domains of pC3AP313. The tetanus toxoid-specific sequences are from phage lambda vector combinatorial libraries of antibody heavy and light chains derived from the peripheral blood lymphocytes of an individual immunized with tetanus toxoid; Persson et al., *Proc. Natl. Acad. Sci., U.S.A.*, 88:2432–2436 (1991), the disclosure of which is hereby incorporated by reference. Clone 3 is selected from the library screening and the heavy and light chain sequences are respectively isolated by restriction digestion with Xho I/Spe I and Sac I/Xba I and ligated into a similarly digested pComb3 vector. The ligation procedure for creating expression vector libraries and the subsequent expression of the anti-suicide substrate conjugate Fab antibodies is performed as described in Example 2.

2. Selection of Anti-Suicide Substrate-Conjugate Antibodies from Semisynthetic Light and Heavy Chain Libraries A. Preparation of Randomized Sites within the Light Chain CDR3 of a Phagemid Fab Display Protein Produced by a Dicistronic Expression Vector 1) PCR with Coding Degenerate Oligonucleotide Primers Semisynthetic human Fab libraries in which both the CDR3 heavy and light chain domains are randomized are constructed, displayed on the surface of filamentous phage and selected by suicide substrate type inactivation by irreversible covalent bond formation with suicide substrate conjugates. The phagemid expression vector, pC3AP313, containing heavy and light chain sequences for encoding a human antibody that immunoreacts with tetanus toxin, is used as a template for PCR.

Light chain libraries having CDR3 randomized in predetermined amino acid residue positions are prepared using the overlap PCR amplification protocols described herein. In the libraries, oligonucleotide primer pools are designed to result in the formation of CDR3 in lengths of 8, 9 and 10 amino acids to correspond to the naturally occurring loop lengths in humans. Diversity is limited to Kabat positions 92–96, as the remaining four positions are highly conserved in nature.

To amplify the 5' end of the light chain from framework 1 to the end of framework 3 of pC3AP313, the following primer pairs are used. The 5' coding (sense) oligonucleotide primer, KEF, having the nucleotide sequence 5'GAAT-TCTAAACTAGCTAGTCG3' (SEQ ID NO 1), hybridizes to the noncoding strand of the light chain corresponding to the region 5' of and including the beginning of framework 1. The 3' noncoding (antisense) oligonucleotide primer, KV12B, having the nucleotide sequence 5'ATACTGCTGA-CAGTAATACAC3' (SEQ ID NO 2), hybridizes to the coding strand of the light chain corresponding to the 3' end of the framework 3 region. The oligonucleotide primers are from Operon Technologies, Alameda, Calif. The terms coding or sense, used in the context of oligonucleotide primers, identifies a primer that is the same sequence as the DNA strand that encodes a heavy or light chain and that hybridizes to the noncoding strand. Similarly, the term noncoding or antisense identifies a primer that is complementary to the coding strand and thus hybridizes to it.

For overlap PCR, each set of PCR reactions are performed in a 100 microliter (ul) reaction containing 1 microgram of each of oligonucleotide primer listed above in a particular pairing, 8 ul 2.5 mM dNTP's (dATP, dCTP, dGTP, dTTP), 1 ul Taq polymerase, 10 ng of template pC3AP313, and 10 ul of 10×PCR buffer purchased from (Promega Biotech, Madison, Wisc.). Thirty-five rounds of PCR amplification in a Perkin-Elmer Cetus 9600 GeneAmp PCR System thermocycler are then performed. The amplification cycle consists of denaturing at 94 degrees C. (94C) for 1 minute, annealing at 47C for 1 minute, followed by extension at 72C for 2 minutes. To obtain sufficient quantities of amplification product, 15 identical PCR reactions are performed.

The resultant PCR amplification products are gel purified on a 1.5% agarose gel using standard electroelution techniques; "Molecular Cloning: A Laboratory Manual", Sambrook et al., eds., Cold Spring Harbor, N.Y. (1989). Briefly, after gel electrophoresis, the region of the gel containing the DNA fragments of predetermined size is excised, electroeluted into a dialysis membrane, ethanol precipitated and resuspended in buffer containing 10 millimolar (mM) Tris-HCl [Tris(hydroxymethyl)aminomethane-hydrochloride] at pH 7.5 and 1 mM EDTA (ethylenediaminetetraacetic acid) to a final concentration of 50 nanograms/milliliter (ng/ml).

The purified amplification products are then used in an overlap extension PCR reaction with the products of the second PCR reaction, both as described below, to recombine the two products into reconstructed variable domain light chains containing the mutagenized third domain of the complementarity determining region (CDR3).

The second PCR reaction results in the amplification of the light chain from the 3' end of framework region 3 extending to the end of light chain constant region. To amplify this region for encoding a 4 random amino acid residue sequence in the CDR3 having a total length of 8 amino acids, the following primer pairs are used. The 5' coding oligonucleotide primer pool, designated KV4R, has the nucleotide sequence represented by the formula, 5'TAT-TACTGTCAGCAGTATNNKNNKNNKNN-KACTTTCGGCGGAGG GACCAAGGTGGAG3' (SEQ ID NO 3), where N can be A, C, G, or T and K is either G or T. The 3' noncoding primer, T7B, hybridizes to the coding strand at the 3' end of the light chain constant domain and has the sequence 5'AATACGACTCACTATAGGGCG3' (SEQ ID NO 4). The 5' end of the primer pool is complementary to the 3' end of framework 3 represented by the complementary nucleotide sequence of the oligonucleotide primer KV12B and the 3' end of the primer pool is complementary to the 5' end of framework 4. The region between the two specified ends of the primer pool is represented by a 12-mer NNK degeneracy. The second PCR reaction is performed on the pC3AP313 vector in a 100 ul reaction as described above containing 1 ug of each of oligonucleotide primers. The resultant PCR products encode a diverse population of 4 mutagenized amino acid residues in a light chain CDR3 having a total of 8 amino acid residues. In the resultant CDR3, the 4 mutagenized amino acid residue positions are bordered on the amino terminal side by 3 amino acid residues that are left unchanged, Gln-Gln-Tyr, and on the carboxy terminal side by one amino acid residue, Thr. The products are then gel purified as described above.

An alternative oligonucleotide pool for preparing 4 randomized amino acid residues in a CDR3 having 8 amino acid residues is designated k8 having the formula 5'TAT-TACTGTCAGCAGTATNNKNNKNNKNN-KACTTTCGGCGGAGGGACC3' (SEQ ID NO 5). The k8 primer lacks 9 nucleotides from the 3' end of KV4R.

One hundred nanograms of gel purified products from the first and second PCR reactions are then admixed with 1 ug each of KEF and T7B oligonucleotide primers as a primer pair in a final PCR reaction to form a complete light chain fragment by overlap extension. The PCR reaction admixture also contains 10 ul of 10×PCR buffer, 1 ul Taq polymerase and 8 ul 2.5 mM dNTP's as described above.

To obtain sufficient quantities of amplification product, 15 identical overlap PCR amplifications are performed. The resulting light chain fragments beginning at framework 1 and extending to the end of constant region of the light chain thus contains a randomly mutagenized CDR3 region for encoding 4 new amino acid residues. The light chain fragment amplification products from the 15 reactions are first pooled and then gel purified as described above prior to their incorporation into the pC3AP313 surface display phagemid expression vector to form a library as described in Example 3A. The light chain library having a CDR3 of 8 amino acids resulting from amplifications with either KV4R or k8 is designated K8.

To create a randomized light chain CDR3 for encoding a CDR3 having a total of 9 amino acids in which 5 amino acid residues are randomized, the KV5R primer is used with the 3' primer, T7B, previously described. The KV5R has the formula 5'TATTACTGTCAGCAGTATNNKNNK-NNKNNKACTTTCGGCGGAGGGACCAAGGTGGA G3' (SEQ ID NO 6), where N is A, C, G or T and K is G or T.

An alternative oligonucleotide pool for preparing 5 randomized amino acid residues in a CDR3 having 9 amino acid residues is designated k9 having the formula 5'TAT-TACTGTCAGCAGTATNNKNNKNNK-KNNKACTTTCGGCGGAGGGACC3' (SEQ ID NO 7), where N is A, C, G or T and K is G or T. The k9 primer lacks 9 nucleotides from the 3' end of KV5R.

The resultant PCR products from amplifications with either KV5R or k9 encode a diverse population of 5 mutagenized amino acid residues in a light chain CDR3 having a total of 9 amino acid residues. In the resultant CDR3, the 5 mutagenized amino acid residue positions are bordered on the amino terminal side by 3 amino acid residues that are left unchanged, Gln-Gln-Tyr, and on the carboxy terminal side by one amino acid residue, Thr. The light chain library having a CDR3 of 9 amino acids resulting from this amplification is designated K9.

To create a randomized light chain CDR3 for encoding a CDR3 having a total of 10 amino acids in which 6 amino acid residues are randomized, the KV6R primer is used with the 3' primer, T7B, previously described. The KV6R primer has the formula 5'GATTTTGCAGTGTATTACTGTCAG-CAGTATNNKNNKNNKNNKNNKNN-KACTTTCGGCGG AGGGACCAAGGTGGAG3' (SEQ ID NO 8),where N is A, C, G or T and K is G or T.

An alternative oligonucleotide pool for preparing 6 randomized amino acid residues in a CDR3 having 10 amino acid residues is designated k10 and has the formula 5'TAT-TACTGTCAGCAGTATNNKNNKNN-KACTTTCGGCGGAGGGACC3', where N is A, C, G or T and K is G or T (SEQ ID NO 9). The k10 primer is shortened on both the 5' and 3' ends of the KV6R primer by 12 and 9 nucleotides, respectively.

The resultant PCR products from amplifications with either KV6R or k10 encode a diverse population of 6 mutagenized amino acid residues in a light chain CDR3 having a total of 10 amino acid residues. The light chain library having a CDR3 of 10 amino acids resulting from this amplification is designated K10. In the resultant CDR3, the 6 mutagenized amino acid residue positions are bordered on the amino terminal side by 3 amino acid residues that were left unchanged, Gln-Gln-Tyr, and on the carboxy terminal side by one amino acid residue, Thr.

To create a randomized light chain CDR3 for encoding a CDR3 having a total of 10 amino acids in which all 10 amino acid residues are randomized, the KV10R primer is used with the 3' primer, T7B, previously described. The KV10R primer has the formula 5'GATTTTGCAGTGTATTACTGT-NNKNNKNNKNNKNNKNNKNNKNN-KNNKTTCGGCGG AGGGACCAAGGTGGAG3' (SEQ ID NO 10), where N is A, C, G or T and K is G or T.

The resultant PCR products encode a diverse population of 10 mutagenized amino acid residues in a light chain CDR3 having a total of 10 amino acid residues. The light chain library having a CDR3 of 10 amino acids resulting from this amplification is designated K10'.

The light chain CDR3 amino acid residue degenerate or randomized formula encoded by the K9 and K10 libraries is listed in Table 1 in Example 3C.

2) PCR with Noncoding Degenerate Oligonucleotide Primers

Additional semisynthetic human Fab libraries in which both the heavy and light chain CDR3 are randomized are constructed, displayed on the surface of filamentous phage and selected by suicide substrate type inactivation by irreversible covalent bond formation with the suicide substrate conjugates. Another way of introducing randomized nucleotides into a template DNA sequence for encoding amino acid residue substitutions or additions is to use noncoding degenerate primers instead of using coding degenerate oligonucleotide primers as described above in Example 2A1). The coding (sense) degeneracy has the formula 5'-NNK-3', where N can be either A, C, G or T and K is either G or T. For use in this invention, the noncoding (antisense) oligonucleotide primers used in overlap PCR procedures have the degeneracy formula 5'-MNN-3' written in the conventional 5' to 3' direction, where M is equal to either A or C. Written in 3' to 5' direction, the noncoding oligonucleotide had the formula 3'-NNM-5' which is that complementary sequence to the coding formula 5'-NNK-3'. Thus, the noncoding oligonucleotide primers used in this invention provided for incorporating the same coding sequence degeneracies as the coding oligonucleotide primers. In other words, the same semisynthetic library having a particular CDR randomized arrangement can be obtained by using overlap PCR with predetermined coding or noncoding primers. The use of a noncoding primer also requires the use of different overlap primers as described herein.

The resultant PCR products are also prepared from the phagemid expression vector, pC3AP313, containing heavy and light chain sequences for encoding a human antibody that immunoreacts with tetanus toxin.

Light chain libraries having CDR3 randomized in predetermined amino acid residue positions are prepared using the overlap PCR amplification protocols described herein. In the libraries, oligonucleotide primer pools are designed to result in the formation of CDR3 in lengths of 8, 10 and 16 amino acids in length. For all three libraries, the CDR3 is completely randomized using the noncoding degeneracy 5'-MNN-3' that is complementary to the coding degeneracy 5'-NNK-3' as used in primers described in Example 2A1).

To amplify the 5' end of the light chain from framework 1 to the end of CDR3 of pC3AP313 and to incorporate degenerate nucleotide sequences into the amplified DNA, the following primer pairs are used. The 5' coding (sense) oligonucleotide primer, KEF, having the nucleotide sequence 5'GAATTCTAAACTAGCTAGTCG3' (SEQ ID NO 1), hybridized to the noncoding strand of the light chain corresponding to the region 5' of and including the beginning of framework 1. Three separate noncoding (antisense) oligonucleotide primer pools are designed to prepare light chain CDR3 libraries having 8, 10 or 16 randomized amino acid residues. The degenerate oligonucleotides overlap with the 3' end of framework region 3 through the CDR3 into the 5' end of framework region 4.

The primer pool designated p313K38OVb for incorporating 8 randomized amino acid residues has the noncoding nucleotide sequence written in the 5' to 3' direction, 5'GTTCCACCTTTGGTCCCTTGGCCGAAMN-NMNNMNNMNNMNNMNNMNNMNNACAGTAGTAC ACTGCAAAATC3', where M is either A or C, and N can be A, C, G or T (SEQ ID NO 11). The light chain library formed from this amplification is designated CDR3-LCNC8. The primer pool, designated p313K310OVb, for incorporating 10 randomized amino acid residues has the noncoding nucleotide sequence written in the 5' to 3' direction, 5'GTTCCACCTTGGTCCCTTGGCCGAAMN-NMNNMNNMNNMNNMNNMNNMNNMNNMN-NACAG TAGTACACTGCAAAATC3', where M is either A or C, and N can be A, C, G or T (SEQ ID NO 12). The light chain library formed from this amplification is designated CDR3-LCNC10. The primer pool designated p313K316OVb for incorporating 16 randomized amino acid residues has the noncoding nucleotide sequence written in the 5' to 3' direction, 5'GTTCCACCTTGGTCCCTTGGC-CGAAMNNMNNMNNMNNMNNMNNMNNMN-NMNNMNNMNNM NNMNNMNNMNNMNNACAG-TAGTACACTGCAAAATC3', where M is either A or C, and N can be A, C, G or T (SEQ ID NO 13). The light chain library formed from this amplification is designated CDR3-LCNC16.

Three separate first PCR amplifications are then performed with the KEF primer paired with each of the three noncoding degenerate primers listed above. The amplifications are performed as described in Example 2A1).

The second PCR amplification results in the amplification of the light chain from the 5' end of framework region 4 extending to the end of light chain constant region. The 5' coding oligonucleotide, designated p313KF40F, has the nucleotide sequence 5'TTCGGCCAAGGGACCAAGGTG-GAAC3' (SEQ ID NO 4). This primer begins at the 5' end of framework region 4 providing an overlapping region with the corresponding region in the degenerate oligonucleotide primers. The 3' noncoding primer, T7B, hybridizes to the coding strand at the 3' end of the light chain constant domain having the sequence 5'AATACGACTCACTATAGGGCG3' (SEQ ID NO 4). The second PCR reaction is performed as described above.

For overlap PCR, 100 ng of the amplification products from the first and second reactions are pooled following purification and a third round of PCR is performed using the primer pair, KEF and T7B, as described above to form a complete light chain fragment by overlap extension. The light chain fragment amplification products from 15 parallel reactions are first pooled and then gel purified as described above prior to their incorporation into the pC3AP313 surface display phagemid expression vector to form a library as described in Example 3A. The resultant semisynthetic light chain libraries encode a CDR3 of 8, 10 or 16 randomized amino acids.

B. Preparation of Randomized Sites within the Heavy Chain CDR3 of a Phagemid Fab Display Protein Produced by a Dicistronic Expression Vector Heavy chain libraries having randomized CDR3 in lengths of 5, 10 and 16 amino acids are also prepared using the pC3AP313 surface display expression vector as the PCR template. The resultant libraries prepared as described below are then crossed with the K8, K9 and K10 light chain libraries prepared in Example 2A1). The heavy chain CDR3 (HCDR3) having 10 amino acid residues is approximately the average length utilized in human antibodies. CDR3 having 5 and 16 amino acid residues are chosen to be representative of short and long CDRs respectively based on a previous report on the genetic diversity in this region. Complete randomization using an NNK or NNS degeneracy yields libraries designated 5, 10 and 16.

Alternatively, the penultimate position of the HCDR3 is fixed as aspartic acid, and yields libraries designated G, F and E, respectively, 5, 10 and 16 amino acid residue CDR3s. The first position of the F and E libraries is also fixed as a glycine residue encoded by the triplet codon GGT. The penultimate aspartic acid, Kabat position 101, is conserved in 75% of human antibodies; Kabat et al., "Sequences of Proteins of Immunological Interest, 5th ed., (NIH, Washington, DC), the disclosure of which is hereby incorporated by reference. The Kabat 101 position is thought to be structurally significant in stabilizing the immunoglobulin loop structure; Chothia et al., *J. Mol. Biol.*, 196:901–917 (1987).

The following amplifications are performed for preparing heavy chain G, F and E libraries. The first PCR reaction results in the amplification of the region of the heavy chain fragment in the pC3AP313 phagemid beginning at framework region 1 and extending to the end of framework region 3 which is located 5' to CDR3. The degenerate primer pools designed for use with the pC3AP313 template result in the retention of a conserved aspartic acid residue in the next to last position in the CDR3 for all 3 lengths of CDR3s prepared. The retention of the aspartic acid residue in this position is preferred for use in this invention as the expressed proteins containing this residue exhibit high affinity binding characteristics.

To amplify the 5' end of the heavy chain from framework 1 to the end of framework 3, the following primer pairs are used. The 5' coding oligonucleotide primer, FTX3, having the nucleotide sequence 5'GCAATTAACCCTCAC-TAAAGGG3' (SEQ ID NO 15), hybridizes to the noncoding strand of the heavy chain corresponding to the region 5' of and including the beginning of framework 1. The 3' noncoding oligonucleotide primer, BFR3U, having the nucleotide sequence 5'TCTCGCACAGTAATACACGGCCGT3' (SEQ ID NO 16), hybridizes to the coding strand of the heavy chain corresponding to the 3' end of the framework 3 region. The oligonucleotide primers are from Operon Technologies.

The PCR reaction is performed as described in Example 2A1). The resultant PCR amplification products are then gel purified, and are used in an overlap extension PCR reaction with the products of the second PCR reaction, both as described below, to recombine the two products into reconstructed heavy chains containing mutagenized CDR3s.

The second PCR reaction results in the amplification of the heavy chain from the 3' end of framework region 3 extending to the end of $C_H1$ region. To amplify this region for encoding a 5 random amino acid residue sequence having an aspartic acid in the fourth position in the CDR3, the following primer pairs are used. The 5' coding oligonucleotide primer pool, designated HCDRD5, has the nucleotide sequence represented by the formula, 5'GCCGTGTATTACTGTGCGAGANNKNNKNNKGACNNKTGGGGCCAAGGGACCACGGTC3' (SEQ ID NO 17), where N can be A, C, G, or T and K is either G or T. The 5' end of the primer pool is complementary to the 3' end of framework 3 represented by the complementary nucleotide sequence of the oligonucleotide primer BFR3U and the 3' end of the primer pool is complementary to the 5' end of framework 4. The region between the two specified ends of the primer pool is represented by a 12-mer degeneracy of 4 NNK triplets plus a sequence encoding a conserved aspartic acid residue one position from the end of the CDR3. The 3' noncoding oligonucleotide primer, R3B, having the nucleotide sequence 5'TTGATATTCACAAACGAATGG3' (SEQ ID NO 18), hybridizes to the coding strand of the heavy chain corresponding to the 3' end of $C_H1$.

The sequence 5'-NNK-3' represents the coding strand sequence having the complementary sequence 3'-NNM-5' in the primer as read from the 3' to 5' direction. Thus, in the primer as listed below the noncoding strand sequence is 5'-MNN-3' as read in the 5' to 3' direction. The coding triplet sequence 5'-NNK-3' is designed to prevent the production of deleterious stop codons. The only stop codon that can result from the expression of NNK may be an amber mutation that is suppressed when the phagemid is expressed in an amber-suppressing host cell, preferably *E. coli* supE strain.

The second PCR reaction is then performed on pC3AP313 in an 100 ul reaction as described above containing 1 ug of each of oligonucleotide primers HCDRD5 and R3B. The resultant PCR products encode a diverse population of mutagenized CDR3s of 5 amino acid residues in length with a conserved aspartic acid residue in the fourth amino acid residue position in the CDR3. The products are then gel purified.

One hundred nanograms of gel purified products from the first and second PCR reactions are then admixed with 1 ug each of FTX3 and R3B oligonucleotide primers as a primer pair in a final PCR reaction to form a complete heavy chain fragment by overlap extension. The PCR reaction admixture also contains 10 ul 10×PCR buffer, 1 ul Taq polymerase and 8 ul 2.5 mM dNTP's as described above. The PCR reactions are performed as described above.

To obtain sufficient quantities of amplification product, 15 identical PCR reactions are performed. The resulting heavy chain fragments begin at framework 1 and extended to the end of CH1 and have a randomly mutagenized CDR3 for encoding 5 amino acid residues with a conserved aspartic acid residue. The heavy chain fragment amplification products from the 15 reactions are first pooled and then gel purified prior to their incorporation into a digested pC3AP313 surface display phagemid expression vector to form a library as described in Example 3B. The resulting CDR3-randomized heavy chain phagemid library is designated library G.

In addition to randomizing the CDR3 in pC3AP313 for expressing 5 amino acid residues, PCR amplifications are performed for expressing a CDR3 containing 10 amino acid residues. Two separate PCR amplifications are performed as described above with the only exception being that, in the second reaction, the 5' coding degenerate primer, designated HCDRD10, is used to encode 10 amino acid residues comprising the heavy chain CDR3. The degenerate 5' coding primer used here is designed to retain the first amino acid position of a glycine residue in the pC3AP313 template and incorporate a conserved aspartic acid residue in the ninth amino acid position. The HCDRD10 primer has the formula: 5'GCCGTGTATTACTGTGCGAGAGGTNN-KNNKNNKNNKNNKNNKNNKGACNNKTGGGGCCAAGGGACCACGGTC3' (SEQ ID NO 19), where N is A, C, G or T and K is G or T. The amino acid sequences comprising the CDR3 encoded by the use of the HCDRD10 primer have an aspartic acid residue conserved in the ninth position of the CDR3. The resultant products are pooled and purified as described above prior to insertion into a digested pC3AP313 surface display phagemid expression vector to form a library as described in Example 3B. The resulting CDR3-randomized heavy chain phagemid library is designated library F.

PCR amplifications using the template pC3AP313 are also performed for expressing a randomized CDR3 containing 16 amino acid residues. The degenerate 5' coding primer used for this amplification is designed to retain the first amino acid position of a glycine residue in the pC3AP313 template and incorporate a conserved aspartic acid residue in the fifteenth amino acid position. Two separate PCR amplifications are performed as described above for the CDR3 having 5 amino acids with the only exception being that, in the second reaction, the 5' coding degenerate primer, designated HCDRD16, used to encode 16 random amino acid residues has the formula: 5'GCCGTGTATTACTGTGCGAGAGGTNNKNNKNNKNNKNNKNN-KNNKNNKNNKNNKNN KNNKGACNNKTGGGGC-CAAGGGACCACGGTC3' (SEQ ID NO 20), where N is A, C, G or T and K is G or T. The amino acid sequences comprising the CDR3 encoded by the use of the HCDRD16 primer have an aspartic acid conserved in position 15. The resultant products are pooled and purified as described above prior to insertion into a digested pC3AP313 surface display phagemid expression vector to form a library as described in Example 3B. The resulting phagemid library is designated library E.

As described above, the resultant randomized heavy chain CDR3s of various lengths having a conserved aspartic acid residue in the penultimate position amplified from pC3AP313 are purified, digested and ligated back into pC3AP313 for preparation of separate expression libraries as described in Example 3B.

The heavy chain CDR3 amino acid residue degenerate or randomized formula encoded by the E and F libraries is listed in Table 1 in Example 3C.

In similar overlap PCR amplifications, heavy chain libraries having completely randomized CDR3s in lengths of 5, 10 or 16 are prepared. The degenerate oligonucleotide pool for preparing the CDR3-HC5 library has the nucleotide formula 5'GTGTATTATTGTGC-GAGANNSNNSNNSNNSNNSTGGGGC-CAAGGGACCACG3', where N can be either A, C, G or T and S is either G or C (SEQ ID NO 21). The resultant library is designated CDR3-HC5. The degenerate oligonucleotide pool for preparing the CDR3-HC10 library has the nucleotide formula 5'GTGTATTATTGTGC-GAGANNSNNSNNSNNSNNSNNSNNSNNSNNSNNST GGGGCCAAGG GACCACG3', where N can be either A, C, G or T and S is either G or C (SEQ ID NO 22). The resultant library is designated CDR3-HC10. The degenerate oligonucleotide pool for preparing the CDR3-HC16 library, designated 7ECDR3, has the nucleotide formula 5'GTG-TATTATTGTGC-GAGANNSNNSNNSNNSNNSNNSNNSNNSNNSNN SNNSNNSNNSNN SNNSNNSTGGGGCCAAGGGAC-CACG3', where N can be either A, C, G or T and S is either G or C (SEQ ID NO 23). The resultant library is designated CDR3-HC16. As described above, the resultant completely randomized heavy chain CDR3s of various lengths amplified from pC3AP313 are then purified, digested and ligated back into a digested pC3AP313 expression vector for preparation of an expression library as described in Example 3B.

3. Preparation of Heavy and Light Chain Expression Vector Libraries having Randomized CDR3

A. Light Chain Libraries

The light chains having randomized CDR3 from the overlap PCR amplifications using both coding and noncoding degenerate oligonucleotide primers produced in Example 2A are then separately introduced into the pC3AP313 pComb3-based monovalent Fab phage display vector prepared as described in Example 1. The PCR products resulting from each of the amplifications prepared in Example 2A are separately inserted into a phagemid expression vector to prepare phagemid libraries. As described below, the resultant gel purified light chain PCR CDR3-randomized products prepared in Example 2A are digested with restriction enzymes and separately ligated into the pC3AP313 phagemid expression vector that is similarly digested.

For preparation of phagemid libraries for expressing the light chain PCR products prepared in Example 2A, the PCR products are separately digested with Sac I and Aat II and separately ligated with a similarly digested pC3AP313 phagemid expression vector prepared as described in Example 1. Digestion of the pC3AP313 vector with Sac I and Aat II removes the nucleotide sequence region beginning at the 5' end of the native light chain variable domain to the beginning of framework 4. The ligation thus results in operatively linking the light chain framework 1 through randomized CDR3 PCR products with the native framework 4 domain present in the pC3AP313 vector. The expression of the resultant light chain libraries is under the control of a LacZ promoter and pelB leader sequence.

Phagemid libraries for expressing each of the Fabs having randomized light chain CDR3 of this invention are prepared in the following procedure. To form circularized vectors containing the PCR product insert, 640 ng of the digested PCR products are mixed with 2 ug of the linearized pC3AP313 phagemid vector and ligation is allowed to proceed 12 hours at room temperature using 10 units of BRL ligase (Gaithersburg, Md.) in BRL ligase buffer in a reaction volume of 150 ul. Five separate ligation reactions are performed to increase the size of the phage library having randomized CDR3. Following the ligation reactions, the circularized DNA is precipitated at −20C for 2 hours by the admixture of 2 ul of 20 mg/ml glycogen, 15 ul of 3M sodium acetate at pH 5.2 and 300 ul of ethanol. DNA is then pelleted by microcentrifugation at 4C for 15 minutes. The DNA pellet is washed with cold 70% ethanol and dried under vacuum. The pellet is resuspended in 10 ul of water and transformed by electroporation into 300 ul of E. coli XL1-Blue cells to form a phage library. The total yield from the PCR amplification and transformation procedure described herein is approximately $10^8$ independent transformants.

The light chain libraries having randomized CDR3 of 4, 5, 6 and 10 amino acid residues (respectively in a CDR3 of 8, 9, 10 and 10 amino acid residues) resulting from the PCR products obtained with the coding degenerate primer pool are respectively designated K8, K9, K10 and K10'. The degenerate formulas of the CDR3 amino acid residue sequences encoded by the light chain libraries K9 and K10, shown crossed with the heavy chain libraries E and F, are listed in Table 1 in Example 3C below. The light chain libraries having CDR3 of 8, 10 and 16 amino acid residues resulting from the PCR products obtained with the noncoding degenerate primer pool are respectively designated CDR3-LCNC8, CDR3-LCNC10 and CDR3-LCNC16.

B. Heavy Chain Libraries

The heavy chains having randomized CDR3 produced in Example 2B from overlap PCR amplifications are then separately introduced into the monovalent Fab phage display vector pComb3 prepared as described in Example 1. The PCR products resulting from each of the amplifications prepared in Example 2B are separately inserted into a phagemid expression vector to prepare phagemid libraries. As described below, the resultant gel purified light chain PCR fragments prepared in Example 2B are digested with the restriction enzymes and separately ligated into the pC3AP313 phagemid expression vector that is similarly digested.

For preparation of phagemid libraries for expressing the heavy chain PCR products prepared in Example 2B, the PCR products are digested with Xho I and Spe I and separately ligated with a similarly digested pC3AP313 phagemid expression vector prepared as described in Example 1. Digestion of the pC3AP313 vector with Xho I and Spe I removes the native nucleotide sequence region beginning at the 5' end of the heavy chain variable domain to the beginning of the heavy chain constant domain, $C_H1$. The ligation thus results in operatively linking the framework 1 through randomized CDR3 PCR products with the native $C_H1$ domain present in the pC3AP313 vector. The expression of the resultant heavy chain libraries is under the control of a LacZ promoter and pelB leader sequence.

Phagemid libraries for expressing each of the Fabs having randomized heavy chain CDR3 of this invention are prepared as described above for the light chain. The total yield from the PCR amplification and transformation procedure described herein is approximately $10^8$ independent transformants.

The heavy chain libraries with CDR3 of 5, 10 or 16 amino acid residues in length resulting from the PCR products obtained retaining an aspartic acid in the penultimate position are respectively designated G, F and E. The degenerate formulas of the heavy chain CDR3 amino acid residue sequences encoded by the randomized heavy chain libraries E and F are listed in Table 1 in Example 3C below. The nonrandomized or native light chain CDR3 from the expression of both E and F heavy chain randomized libraries is also shown. This light chain CDR3 amino acid residue sequence was encoded from the original pC3AP313 template clone as described herein. The heavy chain libraries with completely randomized CDR3 of 5, 10 or 16 amino acid residues in length are respectively designated CDR3-HC5, CDR3-HC10 and CDR3-HC16.

C. Crossed Heavy and Light Chain Libraries

In order to obtain expressed human Fab antibodies having both randomized heavy and light chain fragments, crossed phagemid libraries are constructed. The libraries provided for the expression of recombinant human Fab antibodies having heavy and light chains in which the CDR3 in both are selectively randomized for selection of Fab antibodies that form covalent bonds with suicide substrate conjugates. Libraries in which both CDR3s were randomized are prepared by digestion of the light chain libraries prepared in Example 3A with Xho I and Spe I to remove the pC3AP313 natural heavy chain and replace it with Xho I and Spe I digests of the synthetic heavy chain libraries prepared in Example 3B. Nine crossed libraries are prepared by combination of K8, K9 and K10 light chain libraries with the G, F and E heavy chain libraries.

Crossed libraries are designated by listing the light chain library first separated from the heavy chain library by a slash, e.g., K8/F. All resultant crossed libraries consist of at least $10^8$ independent transformants. The crossed library designated K10/E consists of Fab fragments where 20 positions are randomized. In order for the crossed libraries to be "complete", i.e., where all possible members (combinations of heavy and light chain library members) are represented, more than $10^{30}$ transformants would be necessary. To verify the targeted mutagenesis of the light and heavy chain CDR3, randomly selected clones from each uncrossed library are sequenced prior to crossing.

The amino acid residue sequence of heavy and light chain CDR3 having the defined degeneracies resulting from the expression of crossed libraries K9/E, K9/F, K10/E and K10/F are shown in Table 1. The amino acid residue sequences of randomized heavy and nonrandomized light chain CDR3 encoded by the heavy-chain-randomized E and F libraries are also shown. The amino acid residue sequences are shown in single-letter code where X represents any amino acid residue.

After transformation, to isolate phage expressing Fabs reactive with synthetic suicide substrate conjugates, panning on target suicide substrate conjugates is performed as described in Example 4B below.

Phage are first prepared on which the semisynthetic Fab antibodies are expressed for selecting on suicide substrate conjugates. Three ml of SOC medium (SOC is prepared by admixture of 20 grams (g) bacto-tryptone, 5 g yeast extract and 0.5 g NaCl in 1 liter of water, adjusting the pH to 7.5 and admixing 20 ml of glucose just before use to induce the expression of the heavy chain domain anchored to the phage coat protein 3 (Fd-cpIII) and soluble light chain heterodimer) are admixed to selected phage libraries and the culture is shaken at 220 rpm for 1 hour at 37C. Then 10 ml of SB (SB is prepared by admixing 30 g tryprone, 20 g yeast extract, and 10 g Mops buffer per liter with pH adjusted to 7) containing 20 ug/ml carbenicillin and 10 ug/ml tetracycline are admixed and the admixture is shaken at 300 rpm for an additional hour. This resultant admixture is admixed to 100 ml SB containing 50 ug/ml carbenicillin and 10 ug/ml tetracycline and shaken for 1 hour, after which helper phage VCSM13 ($10^{12}$ pfu) are admixed and the admixture is shaken for an additional 2 hours. After this time, 70 ug/ml kanamycin is admixed and maintained at 30C overnight. The lower temperature results in better heterodimer incorporation on the surface of the phage. The supernatant is cleared by centrifugation (4000 rpm for 15 minutes in a JA10 rotor at 4C). Phage are precipitated by admixture of 4% (w/v) polyethylene glycol 8000 and 3% (w/v) NaCl and maintained on ice for 30 minutes, followed by centrifugation (9000 rpm for 20 minutes in a JA10 rotor at 4C). Phage pellets are resuspended in 2 ml of PBS and microcentrifuged for three minutes to pellet debris, transferred to fresh tubes and stored at −20C for subsequent screening as described below.

TABLE I

| Library | Heavy Chain CDR3 | Light Chain CDR3 |
| --- | --- | --- |
| E | YYCARGXXXXXXXXXXXXXXXDXWGQG | QQYGGSPWFGQ |
| F | YYCARGXXXXXXXDXWGQG | QQYGGSPWFGQ |
| K9/E | YYCARGXXXXXXXXXXXXXXXDXWGQG | QQYXXXXXXTFGG |
| K9/F | YYCARGXXXXXXXDXWGQG | QQYXXXXXXTFGG |
| K10/E | YYCARGXXXXXXXXXXXXXXXDXWGQG | QQYXXXXXXTFGG |
| K10/F | YYCARGXXXXXXXDXWGQG | 'QQYXXXXXXTFGG |

The heavy chain CDR3 amino acid residue sequences listed above corresponding to libraries E and F have been respectively assigned SEQ ID NOs 24 and 25. Both of these sequences are shown three times, once in the uncrossed library and the other two times crossed with the light chain of either K9 or K10. The light chain CDR3 amino acid residue sequence shown twice above encoded by both libraries E and F has been assigned SEQ ID NO 26. The light chain CDR3 amino acid residue sequences listed above corresponding to libraries K9 and K10 have been respectively assigned SEQ ID NOs 27 and 28. These sequences are each shown twice crossed with both E and F heavy chain libraries.

The other light chain libraries, K10', CDR3-LCNC8, CDR3-LCNC10 and CDR3-LCND16 are similarly crossed with all of the heavy chain libraries prepared in Example 3B to form additional crossed libraries having varying lengths of CDR3 having varying randomized amino acid residues.

4. Selection of Anti-Suicide Substrate-Conjugate Fab Antibodies Expressed on Phage A. Preparation of Phage Expressing Semisynthetic Fab Heterodimers For determining the titering colony forming units (cfu), phage (packaged phagemid) are diluted in SB and 1 ul is used to infect 50 ul of fresh ($A_{OD600}=1$) E. coli XL1-Blue cells grown in SB containing 10 ug/ml tetracycline. Phage and cells are maintained at room temperature for 15 minutes and then directly plated on LB/carbenicillin plates.

B. Selection of the Phagemid-Displayed Semisynthetic Fab Heterodimers

1). Multiple Cycles of Panning/Affinity Selection of the Phage Library having Phagemid Fab-Displayed Synthetic Binding Site Proteins The phage libraries produced in Example 3A, 3B and 3C are selected as described herein on microtiter plates coated with the affinity label suicide substrate conjugate target molecules. Three synthetic affinity label suicide substrate conjugates are chosen for screening for improved high activity thiol-esterase like catalytic antibodies having either a randomized heavy or light chain domain or both. The affinity label suicide substrate type conjugating compounds, shown in FIG. 1 and labeled as 1 (SPDP), 16 (Sulfo-LC-SPDP) and, 17 (SMPT), respectively, are coupled separately to BSA using standard procedures; Tijssen P., (1985) "Laboratory Techniques in Biochemistry and Molecular Biology: Practice and Theory of Enzyme Immunoassays", Elsevier, N.Y. The reagents SPDP-BSA, LC-SPDP-BSA and, SMPT-BSA are used to coat microtiter wells.

The chemical event selection procedure significantly modifies that originally described for selection based on noncovalent complex formation; Parmley et al., *Gene*, 73:305–318 (1988). This procedure is described in detail below for one preparation, (See Compound 2, FIG. 2 and Example 7), and is followed for each of the phage-display screening procedures of all libraries prepared for use in this invention.

A. General Method for Preparation of Microtiter Plate/ Affinity Purification Matrix The mechanism-based suicide substrate conjugate is immobilized on plastic. Wells of a microtiter plate (Costar 3690) are separately coated overnight at 4C with the purified target suicide substrate conjugates prepared above. The wells are washed twice with water and blocked by completely filling the well with 3% (w/v) bovine serum albumin (BSA) in PBS and incubating the plate at 37C for 1 hour. Blocking solution is removed by shaking, 50 ul of each of the phage libraries prepared above (typically $10^{11}$ cfu) are added to each well, and the plate is incubated for 2 hours at 37C.

2). A General Procedure of Affinity Selection

Phage are removed and each well is then washed with TBS/Tween (50 mM Tris-HCl at pH 7.5, 150 mM NaCl, 0.5% Tween 20) for five minutes at room temperature. The plate is washed with distilled water, and noncovalently adherent phage are eluted by the addition of 50 ul of elution buffer (0.1M HCl, adjusted to pH 2.2 with solid glycine) to each well and incubation at room temperature for five minutes. Covalently bound phage are eluted in two separate 50 µl washes with 20 mM DTT at 25C. The resulting DTT-eluates from each of the six libraries are combined.

Eluted phage are used to infect 2 ml of fresh ($OD_{600}=1$) *E. coli* XL1-Blue cells for 15 minutes at room temperature, after which 10 ml of SB containing 20 ug/ml carbenicillin and 10 ug/ml tetracycline is admixed. Aliquots of (20, 10, and 1/10 ul are removed for plating to determine the number of phage (packaged phagemids) that are eluted from the plate. The culture is shaken for 1 hour at 37C, after which it is added to 100 ml of SB containing 50 ug/ml carbenicillin and 10 ug/ml tetracycline and shaken for 1 hour. Helper phage VCSM13 ($10^{12}$ pfu) are then added and the culture is shaken for an additional 2 hours. After this time, 70 ug/ml kanamycin is added and the culture is incubated at 37C overnight. Phage preparation and further panning/affinity selections are repeated as described above.

Following each round of affinity selection, the percentage yield of phage are determined, where % yield=(number of phage eluted/number of phage applied)×100.

The final phage output ratio is determined by infecting 2 ml of logarithmic phase XL1-Blue cells as described above and plating aliquots on selective plates. Following the washing and acid elution from the first round of panning, the phage-displayed Fab libraries are then combined in subsequent rounds of affinity selection to identify clones from the collection of libraries. By sequencing the selected binders, the source library of the clones is known.

From this procedure, clones are selected from each of the Fab libraries for their ability to form covalent bonds with the target suicide substrates. The affinity screened phage surface libraries are then converted into ones expressing soluble semisynthetic Fab antibodies for further characterization as described in Example 4C.

C. Preparation of Soluble Fab Proteins

In order to further characterize the specificity of the semisynthetic Fab antibodies expressed on the surface of phage as described above, soluble heterodimers are prepared and analyzed in ELISA assays on synthetic suicide substrate conjugate target-coated plates and by competitive ELISA with increasing concentrations of soluble competitor protein as described below.

To prepare soluble Fabs consisting of heavy and light chains (i.e., heterodimers), phagemid DNA from positive clones selected in Example 4B above is isolated and digested with Spe I and Nhe I. Digestion with these enzymes produces compatible cohesive ends. The 4.7 kb DNA fragment lacking the gIII portion is gel-purified (0.6% agarose) and self-ligated. Transformation of *E. coli* XL1-Blue affords the isolation of recombinants lacking the gIII fragment. Clones are examined for removal of the gIII fragment by Xho I/Xba I digestion, which should yield a 1.6 kb fragment. Clones are grown in 100 ml SB containing 50 ug/ml carbenicillin and 20 mM $MgCl_2$ at 37C until an $OD_{600}$ of 0.2 is achieved. IPTG (final concentration is 1 mM) is added and the culture grown overnight at 30C (growth at 37C provides only a light reduction in heterodimer yield). Cells are pelleted by centrifugation at 4000 rpm for 15 minutes in a JA10 rotor at 4C. Cells are resuspended in 4 ml PBS containing 34 ug/ml phenylmethylsulfonyl fluoride (PMSF) and lysed by sonication on ice (2–4 minutes at 50% duty). Debris is pelleted by centrifugation at 14,000 rpm in a JA20 rotor at 4C for 15 minutes. The supernatant is used directly for ELISA analysis and is stored at −20C. For the study of a large number of clones, 10-ml cultures provides a sufficient amount of the semisynthetic Fab antibodies for analysis. In this case, sonications are performed in 2 ml of buffer.

The soluble heterodimers prepared above are assayed by ELISA where applicable as described in Example 5.

5. Characterization of Soluble Semisynthetic Fab Heterodimers

A. ELISA

ELISA assays are performed to confirm the binding specificity and chemical reactivity of the affinity selected phage semisynthetic Fab antibodies prepared above toward synthetic suicide substrate conjugates. For ELISA, 1 ug/well of the synthetic suicide substrate conjugates prepared in Example 4B are separately admixed to individual wells of a microtiter plate and maintained at 4C overnight to allow the suicide substrate conjugate solution to adhere to the walls of the well. After the maintenance period, the wells are washed once with PBS and thereafter maintained with a solution of 3% BSA to block nonspecific sites on the wells. The plates are maintained at 37C for 1 hour after which time the plates are inverted and shaken to remove the BSA solution. Soluble Fab heterodimers expressing the semisynthetic Fab heterodimers prepared in Example 4C are then admixed separately to each well and maintained at 37C for 1 hour to form immunoreaction products. Following the maintenance period, the wells are washed 10 times with PBS to remove unbound soluble antibody and then incubated with a secondary goat anti-human FAB conjugated to alkaline phosphatase diluted in PBS containing 1% BSA. The wells are incubated at 37C for 1 hour after which the wells are washed 10 times with PBS followed by development with p-nitrophenyl phosphate.

B. Sequence Determination of Affinity Selected Proteins

Nucleic acid sequencing is performed on double-stranded DNA using Sequenase 1.0 (USB, Cleveland, Ohio) encoding the specific soluble synthetic suicide substrate conjugate-binding Fab heterodimers of this invention characterized above.

The sequences of the CDR3 regions from the antibodies selected using conjugates of 1, 16 and 17 are shown in FIG. 2. Also see Table II in Example 7 for the heavy and light chain CDR3 amino acid residue sequences of Compound 2-selected and characterized Fabs. On the left hand side of both tables, the selected antibodies (referred to as the clone) and on the right hand side of the figure are listed the anti-suicide substrate conjugate conjugates (numbers 1, 19 and, 20) on which the antibodies are screened. The middle columns, from left to right, show the amino acid residue sequence of the heavy (HCDR3) and light chain CDR3 (LCDR3) from the designated clone. The SEQ ID NOs are listed adjacent to each of the heavy and light chain sequences. The first column in each table shows the designation of the crossed light and heavy chain library from which the clone is derived and selected. In all cases, the light chain is listed first followed by the heavy chain library or none if applicable.

6. Deposit of Materials

The following plasmid was deposited on or before Feb. 2, 1993, with the American Type Culture Collection, 1301 Parklawn Drive, Rockville, Md., U.S.A. (ATCC):

| Material | ATCC Accession No. |
|---|---|
| Plasmid pC3AP313 | ATCC 75408 |

This deposit is made under the provisions of the Budapest Treaty on the International Recognition of the Deposit of Microorganisms for the Purpose of Patent Procedure and the Regulations thereunder (Budapest Treaty). This assures maintenance of a viable plasmid deposit for 30 years from the date of deposit. The deposit will be made available by ATCC under the terms of the Budapest Treaty which assures permanent and unrestricted availability of the progeny of the viable plasmids to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the plasmid deposit should die or be lost or destroyed when cultivated under suitable conditions, it will be promptly replaced on notification with a viable specimen of the same plasmid. Availability of the deposited plasmid is not to be construed as a license to practice the invention in contravention of the rights granted under the authority of any government in accordance with its patent laws.

The present invention is not to be limited in scope by the plasmid deposited, since the deposited embodiment is intended as a single illustration of one aspect of the invention and any plasmid vectors that are functionally equivalent are within the scope of this invention. The deposit of material does not constitute an admission that the written description herein contained is inadequate to enable the practice of any aspect of the invention, including the best mode thereof, nor is it to be construed as limiting the scope of the claims to the specific illustration that it represents.

7. Selection of the Phagemid-Displayed Semisynthetic Fab Heterodimers Containing Cysteine Residues in the Antibody Active Site A. Detailed Procedures for Practicing Chemical Event Selection Step A Generating Semisynthetic Phage-Display Libraries: Mutagenizing Combinatorial Antibody Libraries Polypeptides encoding light and heavy chain portions of the Fab are randomized by in vitro mutagenesis as described in Example 2A and 2B. The semisynthetic combinatorial phage libraries (E, F, κ9/E, κ9/F, κ10/E and, κ10/F; Barbas III, C. F., Rosenblum, J. S. & Lerner, R. A. (1993) *Proc. Natl. Acad. Sci. U.S.A.* 90, 6385–6389, Barbas III, C. F, Amberg, W., Simoncsits, A., Jones, T. M. & Lerner, R. A. (1993) *Gene*, 137, 57–62.) are produced as described in Example 3A, 3B and 3C, and then are used in the affinity purification methods described below.

The number of variants, containing an unpaired cysteine residue in the mutagenized CDR3 region, in the population of semisynthetic phage-encoded antibodies is estimated. Based on probability alone, the nucleotide chemical synthesis protocol produces 32 possible codons (one codon encoding cysteine). Using an average of 8 for the number of randomized residues, the "naive" semisynthetic library thus produced by in vitro mutagenesis should have 20%, of the approximately $10^8$ clones, contain an unpaired cysteine, i.e., $(1/32) \times (31/32)^7 \times 8 = 0.20$. In practice, DNA sequencing a sample population of the unselected semisynthetic clones, produced by in vitro mutagenesis, gives a value of 23% which contain an unpaired cysteine residue in the above described mutagenized CDR3 regions.

Step B Multiple Cycles of Affinity Selection of the Phage Library having Phagemid Fab-Displayed Synthetic Binding Site Proteins The phage libraries produced in Example 3A, 3B and 3C are selected as described herein on microtiter plates-coated with the suicide substrate conjugate target molecules.

1. Preparation of Microtiter Plate/Suicide Substrate-Type Affinity Selection Matrix, Composition 3

The affinity label suicide substrate conjugate is immobilized on plastic. Compound 1 (available from Pierce) FIGS. 3 and 4, is reacted with BSA under standard conditions; Tijssen P., (1985) "Laboratory Techniques in Biochemistry and Molecular Biology: Practice and Theory of Enzyme Immunoassays", Elsevier, N.Y. The affinity label suicide substrate BSA conjugate, compound 2, is diluted to 0.1 mg/ml, and 25 µl is admixed with the microtiter wells of a microtiter plate (Costar 3690) overnight at 4C. Dried affinity purification matrix is fixed upon adding 50 µl of methanol to microtiter wells previously reacted with compound 2. After 5 minutes, the methanol is discarded and the affinity purification matrix dried at room temperature. The wells are washed twice with water. Preventing nonspecific adsorption of phage or phage-displayed proteins to the affinity purification matrix is accomplished by coating the wells with bovine serum albumin (BSA). Wells are completely filled with a 1% BSA/PBS solution (phosphate-buffered saline; 10 mM sodium phosphate, 150 mM NaCl, pH 7.4) at 37C for 30 minutes. Blocking solution is removed and the wells are used for multiple cycles of affinity selection as described below.

i. PHAGE ENRICHMENT CYCLE NUMBER 1

A. Suicide Substrate-Type, Chemical Event Affinity Purification Cycle 1: Step A, Covalent Bond Formation The affinity label suicide substrate conjugate, 3, prepared above in Example 7B is used to screen phage libraries for the chemical event of disulfide exchange. In the first round of affinity selection or "panning", the six previously described (Example 3A, 3B and 3C) semisynthetic libraries E, F, κ9/E, κ9/F, κ10/E and, κ10/F are screened. Binding the semisynthetic library of antibody-displayed phage to the affinity support is accomplished by admixing a 50 ul solution of each purified phage library, prepared above (typically $10^{11}$ cfu), with separate wells. The phage is reacted with the immobilized affinity label suicide substrate conjugate at 37C for 2 hours.

B. Step B. Washing

Removing nonspecific and noncovalently bound phage is accomplished by washing each microtiter well, at 25C for 5 minutes, sequentially with:

1] 100 µl of washing buffer TBS/0.5% Tween, 1% BSA (Tris-buffered saline; 50 mM Tris base, 150 mM NaCl, pH 7.5);
2] 100 µl of water;
3] 100 µl of acid solution (0.1M HCl, pH 2.2, adjusted with glycine);
4] 100 µl of water.

C. Step C. Phase Elution

Covalently bound phage are eluted in two separate 50 µl washes with 20 mM DTT at 25C. The resulting DTT-eluates from each of the six libraries are combined and used to infect 10 ml of E. coli XL1-Blue cells $OD_{600}$=1.0.

Determining Phase Titer

The 10 ml culture is incubated for 15 minutes at 25C. Then, in order to determine the titer of the resulting output-phage, 1 µl of the phage-infected E. coli culture is serially diluted $10^3$, $10^6$, and $10^8$ fold with superbroth and, 1 µl of each diluate is plated on LB (Luria-Bertani)/carbenicillin (20 µg/ml). The titer from the first round is $1.7 \times 10^6$ colony forming units (cfu).

D. Step D. Phage Amplification

Carbenicillin (20 µg/ml) is added to the E. coli XL1-Blue culture, and the culture is agitated at 37C for 1 hour. The concentration of antibiotic carbenicillin then is increased to 50 µg/ml and the culture agitated at 37C for an additional hour. Then the phage-infected E. coli culture is diluted into 100 ml superbroth containing 50 µg/ml carbenicillin, 10 µg/ml tetracycline, and $10^{12}$ plaque forming units (pfu) of VCS M13 helper phage. After further agitating the culture for 2 hours at 37C, kanamycin is added to a final concentration of 70 µg/ml. The culture is then agitated at 37C for 12 hours.

E. Step E, Phage Isolation

Centrifuging at low speed concentrates the remaining E. coli XL1-Blue cells from the resulting culture. The phage-containing supernate is decanted. Phage are isolated by adding to final concentration polyethylene glycol 8000 (4%) and NaCl (3%), to the resulting supernate, then incubating the resulting admixture for 30 minutes on ice precipitating the phage particles, and then concentrating the phage by centrifugation, and then discarding the supernate. Remaining phage are resuspended in TBS/1% BSA and clarified by centrifuging. The resulting clarified phage solution is used in enrichment cycle number 2 of suicide substrate-type, chemical event affinity selection.

Phage Enrichment

Additional affinity selection cycles are employed, as described below, to enrich the phage population of specific phage capable of carrying out the desired disulfide exchange chemical event. Steps A through E are repeated four additional times, described below as cycles 2 through 5. For example, a 50 µl solution of the resultant amplified phage solution obtained in Step E of cycle (X) is used to begin Step A of cycle (X+1). In all subsequent enrichment cycles, as in cycle number 1, covalently bound phage are eluted with two separate 50 µl washes with 20 mM DTT each for 5 minutes at 25C. The eluted phage are titered, amplified, and purified as described in Example 7i.

ii. PHAGE ENRICHMENT CYCLE NUMBER 2

A. Suicide Substrate-Type, Chemical Event Affinity Purification Cycle 2: Step A, Covalent Bond Formation In the second round of affinity purification the combined phage obtained from cycle 1, Step E. are screened. Binding the now enriched semisynthetic library of antibody-displayed phage to the affinity support is accomplished by admixing a 50 ul solution of each purified phage library, prepared above, Example 7iE, (typically $10^{11}$ cfu), with separate wells. The phage is reacted with the immobilized suicide substrate conjugate at 37C for 2 hours.

B. Step B. Washing

Removing nonspecific and noncovalently bound phage is accomplished by washing each microtiter well, at 25C for 5 minutes, sequentially with:

1] 100 µl of washing buffer TBS/0.5% Tween, 1% BSA (Tris-buffered saline; 50 mM Tris base, 150 mM NaCl, pH 7.5); In the second cycle of affinity purification, the washing procedure is altered follows so that the first washing step is repeated two times, five minutes each.
2] 100 µl of water;
3] 100 µl of acid solution (0.1M HCl, pH 2.2, adjusted with glycine);
4] 100 µl of water.

C. Step C. Phage Elution

Covalently bound phage are eluted in two separate 50 µl washes with 20 mM DTT at 25C. The resulting DTT-eluates from each of the six libraries are combined and used to infect 10 ml of E. coli XL1-Blue cells $OD_{600}$=1.0.

Determining Phage Titer

The 10 ml culture is incubated for 15 minutes at 25C. Then, in order to determine the titer of the resulting output-phage, 1 µl of the phage-infected E. coli culture is serially diluted $10^3$, $10^6$, and $10^8$ fold with superbroth and, 1 µl of each diluate is plated on LB (Luria-Bertani)/carbenicillin (20 µg/ml). The enrichment is ten fold.

D. Step D. Phage Amplification

Carbenicillin (20 µg/ml) is added to the E. coli XL1-Blue culture, and the culture is agitated at 37C for 1 hour. The concentration of antibiotic carbenicillin then is increased to 50 µg/ml and the culture agitated at 37C for an additional hour. Then the phage-infected E. coli culture is diluted into 100 ml superbroth containing 50 µg/ml carbenicillin, 10 µg/ml tetracycline, and $10^{12}$ plaque forming units (pfu) of VCS M13 helper phage. After further agitating the culture for 2 hours at 37C, kanamycin is added to a final concentration of 70 µg/ml. The culture is then agitated at 37C for 12 hours.

E. Step E. Phage Isolation

Centrifuging at low speed concentrates the remaining E. coli cells from the resulting culture. The phage-containing supernate is decanted. Phage are isolated by adding to final concentration polyethylene glycol 8000 (4%) and NaCl (3%), to the resulting supernate, then incubating the resulting admixture for 30 minutes on ice precipitating the phage particles, and then concentrating the phage by centrifugation, and then discarding the supernate. Remaining phage are resuspended in TBS/1% BSA and clarified by centrifuging. The resulting clarified phage solution is used in enrichment cycle number 3 of suicide substrate-type, chemical event affinity selection.

iii. PHAGE ENRICHMENT CYCLE NUMBER 3

A. Suicide Substrate-Type, Chemical Event Affinity Purification Cycle 3: Step A, Covalent Bond Formation In the third round of affinity purification the combined phage obtained from cycle 2, Step E. are screened. Binding the now enriched semisynthetic library of antibody-displayed phage to the affinity support is accomplished by admixing a 50 ul solution of each purified phage library, prepared above, Example 7iiE, (typically $10^{11}$ cfu), with separate wells. The phage is reacted with the immobilized suicide substrate conjugate at 37C for 2 hours.

B. Step B. Washing

Removing nonspecific and noncovalently bound phage is accomplished by washing each microtiter well, at 25C for 5 minutes, sequentially with:

1] 100 μl of washing buffer TBS/0.5% Tween, 1% BSA (Tris-buffered saline; 50 mM Tris base, 150 mM NaCl, pH 7.5); In the third cycle of affinity purification, the washing procedure is altered follows so that the first washing step is repeated five times, five minutes each.
2] 100 μl of water;
3] 100 μl of acid solution (0.1M HCl, pH 2.2, adjusted with glycine);
4] 100 μl of water.

C. Step C. Phage Elution

Covalently bound phage are eluted in two separate 50 μl washes with 20 mM DTT at 25C. The resulting DTT-eluates from each of the six libraries are combined and used to infect 10 ml of E. coli XL1-Blue cells $OD_{600}=1.0$.

Determining Phage Titer

The 10 ml culture is incubated for 15 minutes at 25C. Then, in order to determine the titer of the resulting output-phage, 1 μl of the phage-infected E. coli culture is serially diluted $10^3$, $10^6$, and $10^8$ fold with superbroth and, 1 μl of each diluate is plated on LB (Luria-Bertani)/carbenicillin (20 μg/ml). The enrichment is 3 fold.

D. Step D. Phage Amplification

Carbenicillin (20 μg/ml) is added to the E. coli XL1-Blue culture, and the culture is agitated at 37C for 1 hour. The concentration of antibiotic carbenicillin then is increased to 50 μg/ml and the culture agitated at 37C for an additional hour. Then the phage-infected E. coli culture is diluted into 100 ml superbroth containing 50 μg/ml carbenicillin, 10 μg/ml tetracycline, and $10^{12}$ plaque forming units (pfu) of VCS M13 helper phage. After further agitating the culture for 2 hours at 37C, kanamycin is added to a final concentration of 70 μg/ml. The culture is then agitated at 37C for 12 hours.

E. Step E. Phage Isolation

Centrifuging at low speed concentrates the remaining E. coli cells from the resulting culture. The phage-containing supernate is decanted. Phage are isolated by adding to final concentration polyethylene glycol 8000 (4%) and NaCl (3%), to the resulting supernate, then incubating the resulting admixture for 30 minutes on ice precipitating the phage particles, and then concentrating the phage by centrifugation, and then discarding the supernate. Remaining phage are resuspended in TBS/1% BSA and clarified by centrifuging. The resulting clarified phage solution is used in enrichment cycle number 4 of suicide substrate-type, chemical event affinity selection.

iv. PHAGE ENRICHMENT CYCLE NUMBER 4

A. Suicide Substrate-Type, Chemical Event Affinity Purification Cycle 4: Step A, Covalent Bond Formation In the fourth round of affinity purification the combined phage obtained from cycle 3, Step E. are screened. Binding the now enriched semisynthetic library of antibody-displayed phage to the affinity support is accomplished by admixing a 50 ul solution of each purified phage library, prepared above, Example 7iiiE, (typically $10^{11}$ cfu), with separate wells. The phage is reacted with the immobilized suicide substrate conjugate at 37C for 2 hours.

B. Step B. Wiring

Removing nonspecific and noncovalently bound phage is accomplished by washing each microtiter well, at 25C for 5 minutes, sequentially with:

1] 100 μl of washing buffer TBS/0.5% Tween, 1% BSA (Tris-buffered saline; 50 mM Tris base, 150 mM NaCl, pH 7.5); In the fourth cycle of affinity purification, the washing procedure is altered follows so that the first washing step is repeated ten times, five minutes each.
2] 100 μl of water;
3] 100 μl of acid solution (0.1M HCl, pH 2.2, adjusted with glycine); In the fourth cycle of affinity purification the washing procedure is altered follows so that the third washing step is repeated two times, five minutes each.
4] 100 μl of water.

C. Step C, Phage Elution

Covalently bound phage are eluted in two separate 50 μl washes with 20 mM DTT at 25C. The resulting DTT-eluates from each of the six libraries are combined and used to infect 10 ml of E. coli XL1-Blue cells $OD_{600}=1.0$.

Determining Phage Titer

The 10 ml culture is incubated for 15 minutes at 25C. Then, in order to determine the titer of the resulting output-phage, 1 μl of the phage-infected E. coli culture is serially diluted $10^3$, $10^6$, and $10^8$ fold with superbroth and, 1 μl of each diluate is plated on LB (Luria-Bertani)/carbenicillin (20 μg/ml). The enrichment is 0.14 fold.

D. Step D. Phage Amplification

Carbenicillin (20 μg/ml) is added to the E. coli XL1-Blue culture, and the culture is agitated at 37C for 1 hour. The concentration of antibiotic carbenicillin then is increased to 50 μg/ml and the culture agitated at 37C for an additional hour. Then the phage-infected E. coli culture is diluted into 100 ml superbroth containing 50 μg/ml carbenicillin, 10 μg/ml tetracycline, and $10^{12}$ plaque forming units (pfu) of VCS M13 helper phage. After further agitating the culture for 2 hours at 37C, kanamycin is added to a final concentration of 70 μg/ml. The culture is then agitated at 37C for 12 hours.

E. Step E. Phage Isolation

Centrifuging at low speed concentrates the remaining E. coli cells from the resulting culture. The phage-containing supernate is decanted. Phage are isolated by adding to final concentration polyethylene glycol 8000 (4%) and NaCl (3%), to the resulting supernate, then incubating the resulting admixture for 30 minutes on ice precipitating the phage particles, and then concentrating the phage by centrifugation, and then discarding the supernate. Remaining phage are resuspended in TBS/1% BSA and clarified by centrifuging. The resulting clarified phage solution is used in enrichment cycle number 5 of suicide substrate-type, chemical event affinity selection.

v. PHAGE ENRICHMENT CYCLE NUMBER 5

A. Suicide Substrate-Type, Chemical Event Affinity Purification Cycle 5: Step A, Covalent Bond Formation In the fifth round of affinity purification the combined phage obtained from cycle 4, Step E. are screened. Binding the now enriched semisynthetic library of antibody-displayed phage to the affinity support is accomplished by admixing a 50 ul solution of each purified phage library, prepared above, Example 7ivE, (typically $10^{11}$ cfu), with separate wells. The phage is reacted with the immobilized suicide substrate conjugate at 37C for 2 hours.

B. Step B. Washing

Removing nonspecific and noncovalently bound phage is accomplished by washing each microtiter well, at 25C for 5 minutes, sequentially with:

1] 100 μl of washing buffer TBS/0.5% Tween, 1% BSA (Tris-buffered saline; 50 mM Tris base, 150 mM NaCl, pH 7.5); In the fifth cycle of affinity purification, the washing procedure is altered follows so that the first washing step is repeated ten times, five minutes each.

2] 100 μl of water;
3] 100 μl of acid solution (0.1M HCl, pH 2.2, adjusted with glycine); In the fifth cycle of affinity purification, the washing procedure is altered follows so that the first washing step is repeated two times, five minutes each.
4] 100 μl of water.

C. Step C. Phage Elution

Covalently bound phage are eluted in two separate 50 μl washes with 20 mM DTT at 25C. The resulting DTT-eluates from each of the six libraries are combined and used to infect 10 ml of E. coli XL1-Blue cells $OD_{600}=1.0$.

Determining Phage Titer

The 10 ml culture is incubated for 15 minutes at 25C. Then, in order to determine the titer of the resulting output-phage, 1 μl of the phage-infected E. coli culture is serially diluted $10^3$, $10^6$, and $10^8$ fold with superbroth and, 1 μl of each diluate is plated on LB (Luria-Bertani)/carbenicillin (20 μg/ml). The enrichment is 4.7 fold.

D. Step D. Phage Amplification

Carbenicillin (20 μg/ml) is added to the E. coli XL1-Blue culture, and the culture is agitated at 37C for 1 hour. The concentration of antibiotic carbenicillin then is increased to 50 μg/ml and the culture agitated at 37C for an additional hour. Then the phage-infected E. coli culture is diluted into 100 ml superbroth containing 50 μg/ml carbenicillin, 10 μg/ml tetracycline, and $10^{12}$ plaque forming units (pfu) of VCS M13 helper phage. After further agitating the culture for 2 hours at 37C, kanamycin is added to a final concentration of 70 μg/ml. The culture is then agitated at 37C for 12 hours.

E. Step E. Phage Isolation

Centrifuging at low speed concentrates the remaining E. coli cells from the resulting culture. The phage-containing supernate is decanted. Phage are isolated by adding to final concentration polyethylene glycol 8000 (4%) and NaCl (3%), to the resulting supernate, then incubating the resulting admixture for 30 minutes on ice precipitating the phage particles, and then concentrating the phage by centrifugation, and then discarding the supernate. Remaining phage are resuspended in TBS/1% BSA and clarified by centrifuging. The resulting clarified phage solution is used infect E. coli for then producing phage DNA for then sub-cloning the Fab, as described below.

Step C. Screening Fabs for Catalytic Activity i. Sub-Cloning Phagemid Encoded Fab After the fifth round of enrichment, the resultant phagemid DNA is purified by standard procedures; "Molecular Cloning: A Laboratory Manual", Sambrook et al., eds., Cold Spring Harbor, N.Y. (1989). Nucleic acid sequencing is performed on double-stranded DNA using Sequenase 1.0 (USB, Cleveland, Ohio) encoding the selected affinity label, suicide substrate binding Fab heterodimers of this invention. The active site sequences of the antibodies selected with compound 2 are shown in Table II.

ii. Expression of Soluble Fab

Single E. coli strain XL1 Blue colonies harboring the affinity-selected Fab sequences are grown at 37C in LB containing carbenicillin antibiotic to $OD_{600}=0.8$, at which point isopropyl b-D-thiogalactopyranoside (IPTG) to a final concentration of 1 mM is added, and then the resultant E. coli culture is incubated at 30C for 12 hours. The resultant E. coli cells are concentrated by centrifuging, and then are lysed by three freeze and thaw cycles: maintaining the cells alternately at −70C and then 37C in 12 ml of phosphate buffered saline. Centrifuging the resultant lysed cell debris, and decanting the lysate yields supernatant containing soluble E. coli-produced proteins. The resulting supernatant then is tested in an ELISA assay, Example 5A, on microtiter plates, prepared as described above, precoated with the affinity label, suicide substrate-type conjugate, compound 2. DNA sequencing is performed on purified phagemid DNA from colonies which express antibodies capable of binding compound 3 in an ELISA assay.

iii. Sequence Analysis of Isolated Clones

Two clones are derived from the k10/F library in which the codons for 8 residues of the heavy chain CDR3 and 6 of the light chain CDR3 are randomized (bold= randomized position) [Table II, clone 32-7: HCDR3/ GGRDEFGCDY, SEQ ID NO 33 from positions 6 to 15, LCDR3/ QQYKRGLLST, SEQ ID NO 38 from positions 1 to 10; clone 32-11: HCDR3/GIYQCTKADP, SEQ ID NO 36 from positions 6 to 15 LCDR3/QQYQRMSWLT, SEQ ID NO 40 from positions 1 to 10]. Based on probability alone, the unselected library has 23% of the $\sim10^8$ clones containing an unpaired cysteine.

TABLE II

| Fab | HC CDR3 | SEQ ID NO | LC CDR3 | SEQ ID NO |
|---|---|---|---|---|
| 32-1 | YYCARGLMRILITDV . . . WGQG | 29 | QQYGGSPWFGQ | 26 |
| 32-2 | YYCARGVALSVVWVPMGSSDFWGQG | 30 | QQYGGSPWRGQ | 26 |
| 32-5 | YYCARGSRSQVMLRGSIVWDFWGQG | 31 | QQYGGSPWRGQ | 26 |
| 32-6 | YYCARGVYVPVGTGPQLIHDAWGQG | 32 | QQYGGSPWRGQ | 26 |
| 32-7 | YYCARGGRDEFGCDY . . . WGQG | 33 | QQYKRGLLSTFGG | 38 |
| 32-9 | YYCARGVGVRRQGDP . . . WGQG | 34 | QQYGGSPWRGQ | 26 |
| 32-10 | YYCARGRRITARLDG . . . WGQG | 35 | QQYRMGGAGTFGG | 39 |
| 32-11 | YYCARGIYQCTKADP . . . WGQG | 36 | QQYQRMSWLTPGG | 40 |
| 32-12 | YYCARGMVLKSGKDF . . . WGQG | 37 | QQYRAAKWNTPGG | 41 |

After affinity selection and four cycles of enrichment, also approximately 20% of the clones contain cysteine in the mutagenized CDR3 region. The other non-cysteine containing CDR3 phage-Fab mutants which are isolated, are very tight binding and are only released from the affinity matrix when DTT destroys the Fab structure. The lack of sequence homology in the affinity-selected CDR3 regions demonstrates the vast diversity available to generate a common binding site.

iv. Antibody Expression

Phagemid DNA is transformed into E. coli and grown overnight in 100 ml superbroth with 1% glucose at 37C. E. coli cells are pelleted by centrifugation, washed with fresh superbroth several times, and then resuspended into 10 separate 1 liter batches of superbroth containing 50 mg/ml carbenicillin and 20 mM $MgCl_2$. The culture is grown at 37C to an $OD_{600}=0.8$, at which point IPTG was added to a final concentration of 2 mM. The induction temperature is dropped to 25C, and the culture is incubated at 25C overnight. The cells are collected by centrifugation, resuspended into Tris-EDTA, pH 8.0 and, lysed first with lysozyme (1 mg/ml) and second with a French press (18,000 psi).

v. Antibody Purification

An FPLC affinity column is prepared from GammaBind G Sepharose (Pharmacia) and goat anti-human F(ab)'$_2$ IgG (Pierce) as described; E. Harlow, D. Lane, *Antibodies: A Laboratory Manual.* Cold Spring Harbor Laboratory: N.Y., 1988. Two different pH solutions are used for affinity chromatography, Buffer A: 0.05M citric acid, 0.5M NaCl, pH 2.1; Buffer B: 0.1M sodium phosphate, 0.5M NaCl, pH 9.2. The column is equilibrated with ten column volumes of 87.2% B (final pH=7.4), then washed with three volumes of 10.8% B (final pH=2.3) and finally equilibrated with 87.2% B. *E. coli* lysate is loaded directly onto the affinity column followed by several column volumes of washing solution 87.2% B, until the 280 nm reading returns to baseline, then the pH is dropped by changing the solution to 10.8% B. The 10.8% B eluate containing fractions are collected, neutralized, concentrated and dialyzed with 100 mM MOPS, 0.5 mM EDTA, pH 7.4.

The Fab is then purified on an ion-exchange column (Pharmacia Hi-Trap™ SP) using a 0 to 1M NaCl gradient at 25C gradient; Buffer A: 50 mM MOPS, 0.5 mM EDTA, pH 7.0; Buffer B: 50 mM MOPS, 0.5 mM EDTA, pH 7.0, 1M NaCl. Purified Fabs elute at about 0.1M NaCl. The purity of the Fab is confirmed by SDS-PAGE with and without reducing agent and by ELISA. The pure Fab is concentrated and stored in 100 mM MOPS, 0.5 mM EDTA, pH 7.4 at 4C.

The final concentration of Fab is estimated from the $OD_{280}$ by assuming $e_{280}=1.24$ which is estimated from the amino acid sequence $((5700 \times N_{Trp})+(1300 \times N_{Tyr}))$/molecular weight of Fab).

vi. Radiolabeling Experiments

Radiolabeled compound D (FIG. 5) is prepared from 1 and an ethanolic solution of unlabeled and [$^{14}$C]-methylamine hydrochloride (American Radiolabeled chemicals; sp. act. 55 mCi/mmol). The product is purified by preparative thin layer chromatography ($R_f$=0.35, 75/25 ethyl acetate/hexane) to give D in nearly quantitative yield (sp. act. 2.88 mCi/mmol). For labeling the Fab, all reactions are carried out at room temperature in 100 mM MOPS, 0.5 mM EDTA, pH 7.4. All dialyses are carried out at 4C in 100 mM MOPS, 0.5 mM EDTA, pH 7.4. Due of small scale, as well as the propensity of the Fab to adhere to dialysis tubing, it also is necessary to determine the amount of radioactivity bound to the dialysis membrane.

vii. Stopped-Flow Kinetics

Reactions are done using a Hi-Tech stopped-flow spectrophotometer in a 0.2 ml cell with a 1 cm path length and, a 0.2 ml stop volume, at 412 nm. The filter time 33 mseconds. Syringe 1 is charged with 4 mM 32-7 Fab in a variable pH buffer system (MOPS and Bicine for pH range 7-9) with 10% DMF-dioxane as cosolvent. Syringe 2 is charged with 400 mM Ellman's reagent in the same solvent. Using conventional spectrophotometry, only the final 10% of the reaction course of C (FIG. 5) or Ellman's reagent can be recorded.

viii. Steady-State Antibody Kinetics

Reactions are performed in 100 mM MOPS, 0.5 mM EDTA, pH 7.4 or 100 mM Bicine, 0.5 mM EDTA, pH 8.5, 8% DMF (dimethyl formamide)—2% dioxane in the presence of substrate and with or without antibody at 25.0C in 0.2 ml (1 cm) cuvettes or in ELISA microtiter plates. Reaction rates are monitored by observing the increase in absorbance at 343 nm (using a Shimadzu spectrophotometer) or at 340 nm (using a Molecular Devices ELISA plate reader) due to the formation of thiopyridone. The extinction coefficient of thiopyridone is calibrated on both instruments ($e=7.50\times10^{-3}$ mM$^{-1}$cm$^{-1}$ for spectrophotometer, $e=5.36\times10^{-3}$ mM$^{-1}$cm$^{-1}$ for plate reader; pH values 7–9).

A typical procedure using the spectrophotometer is as follows. Cuvettes are filled with 180 μl of buffer and then the appropriate amounts are removed and replaced with Fab 32-7 stock solution. DMF (16 μl) is added to the cuvette and the solutions were mixed. Absorbance is auto-zeroed and the reaction initiated by the addition of 4 μl of 10 mM substrate in dioxane with mixing. The total time from substrate addition to the start of reaction is ~30 s. ELISA reader reactions are performed in a total of 100 μl. A 90 μl portion of buffer is added into the wells and then an amount of buffer is removed and replaced with Fab 32-7 stock solution. Absorbance at 340 nm is read after adding and mixing 8 μl of DMF. The kinetic mode is initiated after adding 2 μl of substrate. Data is recorded every 30 seconds.

B. Results and Discussion

The racemic reagent 1 (FIGS. 3 and 5) is coupled to bovine serum albumin (BSA) by substitution of the succinimide group and used as a probe for cysteine groups in antibody binding sites through the process of disulfide exchange; Brocklehurst, K. (1982) *Methods Enzymol.* 87, 427–469, Gilbert, H. F. (1990) *Adv. Enzymol.* 63, 69–172, (FIG. 6). The bioconjugate 2 (FIG. 3) is immobilized on microtiter plates and used to pan six separate semisynthetic libraries each containing ~10$^5$ copies each of ~10$^8$ distinct transformants; Barbas III, C. F., Rosenblum, J. S. & Lerner, R. A. (1993) *Proc. Natl. Acad. Sci. U.S.A.* 90, 6385–6389, Barbas III, C. F, Amberg, W., Simoncsits, A., Jones, T. M. & Lerner, R. A. (1993) *Gene,* 137, 57–62. These phage display Fab fragments containing randomized complementarity determining region 3 (CDR3) sequences in either a heavy chain, a light chain or both. After binding to 3, (FIG. 6) the phage-Fab are sorted using a series of three separate elutions. The last elution employs dithiothreitol (DTT) to release phage anticipated to be covalently attached through a disulfide bond (FIG. 6). Out of ten clones picked at random, two are shown by sequence analysis of phagemid DNA to have the codon for an unpaired cysteine in the heavy chain CDR3.

One clone, 32-7, is chosen for further investigation. The Fab was over-expressed in *E. coli* and isolated using affinity chromatography and then ion-exchange chromatography. Fab 32-7 is judged to be greater than 98% pure by inspection of native and denaturing gels. As hoped, Fab 32-7 reacts with compound C (FIG. 5) liberating thiopyridone which can be followed spectrophotometrically; Grassetti, D. R., Murray, J. F., Jr. (1967) *Arch. Biochem. Biophys.* 119, 41–49. Based on the estimated total protein concentration and the molar equivalents of thiopyridone produced, the Fab 32-7 consists of 50±10% functional Fab. The remainder is likely to be improperly folded Fab structures.

The existence of a covalent antibody complex is further substantiated using [$^{14}$C]-D. Radioactive protein is isolated after exhaustive dialysis and contains an amount of label corresponding to the quantity of functional Fab determined spectrophotometrically. As for most enzymes which possess an active cysteine, Fab 32-7 is also prone to disulfide interchange with Ellman's reagent (3-carboxy-4-nitrophenyl disulfide); Ellman, G. L. (1959) *Arch. Biochem. Biophys.* 82, 70–77. Under pseudo-first-order conditions at pH 7.4, stopped-flow spectroscopy indicates a half-life for the antibody of 35 seconds (FIG. 7A). Interestingly, this is nearly 30 times slower than the exchange reaction involving free cysteine ($t_{1/2}$=1.3 s). Kinetic titration using Ellman's reagent provides a p$K_a$=8.25 for the active site sulfhydryl. This value is reasonable for a cysteine which behaves as an "isolated" thiol rather than as part of an interactive system; Ascenzi, P., Aducci, P., Torroni, A., Amiconi, G., Ballio, A., Menegatti, E. & Guarneri, M. (1987) *Biochem. Biophys. Acta* 912, 203–210, Lewis, S. D., Johnson, F. A. & Shafer, J. A. (1976) *Biochemistry* 15, 5009–5017.

Remarkably, Fab 32-7 remains stable for months (100 mM MOPS, 0.5 mM EDTA, pH 7.4 at 4C) with no apparent loss in activity and requires no exogenous thiol for activation. The resistance to oxidation, taken together with the kinetic data, suggests the cysteine is sequestered. Inactive papain, for example, consists of protein with incorrect disulfide bonds or cysteines as sulfinic acids; Lowe, G. (1976) *Tetrahedron* 32, 291–302. Even though the Fab molecule contains five cystine linkages, inherent structural motifs or thermodynamic considerations likely preclude intramolecular disulfide shuffling. A buried cysteine would also make protein-s-s-protein formation difficult.

At this point, the active site is known to contain a nucleophilic thiol poised to react with an electrophile at a position in three-dimensional space defined by the reactive sulfur atom of compound C. Hence, the congruent thioester compound E (FIG. 5) where a carbonyl group supplants this atom, was tested and is a substrate for the antibody. In retrospect, the choice of a disulfide for panning is in many ways ideal, not only because of its chemoselectivity for cysteine groups, but also because the reactive sulfur atom has tetrahedral geometry with two lone pairs of electrons. This may help select for combining sites which promote, or at least allow, formation of the tetrahedral intermediate and attract critical hydrogen bonds which may participate during the catalytic event. When the racemic ester E is added to varying concentrations of the antibody, burst kinetics indicative of the formation of a covalent intermediate are observed; Hartley, B. S. & Kilby, B. A. (1954) *Biochem. J.* 56, 288–297. An analysis of progress curves (product inhibition is not significant) shows the amplitude of the burst to be proportional to 50±10% of the total antibody concentration, comparable with the results using disulfide reagents and suggesting full accumulation of the acyl-antibody (FIG. 7B). The reaction is completely inhibited with 3 or the thiol labeling reagent methyl methanethiolsulfonate (MMTS); Smith, D. J., Maggio, E. T. & Kenyon, G. L. (1975) *Biochemistry* 14, 766–770. The antibody also utilizes compound F (R or S methyl group, FIG. 5) as substrates with a rate similar to E without demonstrating appreciable stereospecificity. Apparently, binding interactions in the region of the methyl group are not significant. The first-order rate constant for approach to the steady-state is k=0.044 min$^{-1}$. This is ~$10^4$ times slower than reactions of papain with amino acid p-nitrophenyl esters, but similar to guinea pig liver transglutaminase, an enzyme invoking cysteine rather than an imidazolium-thiolate pair; Folk, J. E., Cole, P. W., Mullooly, J. P. (1967) *J. Biol. Chem.* 242, 4329–4333.

A less than ideal orientation of the carbonyl carbon relative to the sulfur nucleophile may be responsible for the sluggish acylation of Fab 32-7. The Fab undergoes multiple turnovers and the dependence of the initial velocity on substrate concentration follows simple saturation kinetics ($k_{cat}$=0.030 min$^{-1}$, $K_m$=100 mM; 100 mM MOPS, 0.5 mM EDTA, pH 7.4, 25C). This affords a 30-fold steady-state rate enhancement over the background hydrolysis of compound E. The fact that the catalyst turns over at all is encouraging, since an unactivated thiol ester is an extremely stable species under the assay conditions; Bruice, T. C. & Benkovic, S. J. (1966) Bioorganic Mechanisms, (W.A. Benjamin, Inc., New York), vol. 1, chap. 3, Morse, B. K. & Tarbell, D. S. (1952) *J. Am. Chem. Soc.* 74, 416–419. The first order rate constant for spontaneous hydrolysis of thiol esters at physiological pH is ~$10^{-7}$ min$^{-1}$, whereas the value for the activated ester 5 is 1.0×$10^{-3}$ min$^{-1}$ under our assay conditions. Interestingly, the antibody slowly catalyzes hydrolysis of the corresponding p-nitrophenyl ester of E. However, this reaction may take place on the surface of the protein and with non-cysteine residues since it can not be inhibited with MMTS. A priori, it would not be surprising for the antibody to undergo a stoichiometric reaction with compound E and become inactivated; Pollack, S. J., Nakayama, G. R. & Schultz, P. G. (1988) *Science* 242, 1038–1040. Evidently, the microenvironment of the active site provides a means, perhaps attributable to the stereoelectronic features of the sulfur atom targeted during selection, to accelerate the hydrolysis of the intermediate. In this regard, it can be estimated that the antibody affords a catalytic advantage of ~$10^4$ relative to the decomposition of an acylated cysteine in solution. Improved catalysis would require more efficient transition-state stabilization for acylation and deacylation or activation of water molecules for the deacylation step. While details remain to be elucidated, the results are consistent with the minimal three-step mechanism of substrate binding, acyl-intermediate formation and breakdown fundamental to cysteine and serine proteases; Fersht, A. (1985) *Enzyme Structure and Mechanism*, 2nd Ed. (W.H. Freeman and Company, New York).

The approximate position of the cysteine residue can be ascertained using model building by comparison to Fab's of homologous sequence and known structure (FIG. 8). Not surprisingly, the group resides in a deep cleft itself sheltered from the external environment, but accessible to certain molecules. Most important, the model represents a specific binding site featuring a precise arrangement of residues which can orchestrate catalysis. In the present case, one is constrained by the requirement for the concerted interaction between a nonoxidized sulfhydryl, sufficient binding energy to overcome the entropic barrier in orienting the nucleophile and electrophile, and a mechanism for hydrolysis of the acyl-intermediate. The probability of randomly accessing such complexity from the naive pool can be expected to be exceedingly low. Yet, the pressure applied through selection has generated a subpopulation consisting of 1 in 10 members which have the desired catalytic activity. Interestingly, a monoclonal antibody elicited by immunization with a transition-state analog was previously shown to operate through an acyl-intermediate already demonstrating that the interplay between transition-state stabilization and covalent catalysis is within the repertoire of the antibody combining site; Wirsching, P., Ashley, J. A., Benkovic, S. J., Janda, K. D. & Lerner, R. A. (1991) *Science* 252, 680–685.

The procedure used here adds to the armamentarium of antibody catalysis in that it allows one to directly select for a chemical event which can be included in the mechanistic plan for the reaction to be catalyzed. Mechanism-based inhibitors have been used in enzymology to inhibit enzymes where a mechanism is known or to give evidence for a proposed mechanism; Silverman, R. B. (1988) *Mechanism-Based Enzyme Inactivation: Chemistry and Enzymology*, Vol. 1 and Vol. 2 (CRC Press, Inc., Boca Raton, Fla.). In one sense, the compound we used to select our antibodies can be considered a mechanism-based inhibitor, but here the process has been reversed, and instead of probing a catalytic mechanism it has been used to select for a molecule exhibiting a mechanism from an otherwise random system. In principle, any mechanism-based inhibitor can be used to select for at least part of a chemical mechanism. The mechanism can be refined and evolved by iterative procedures of selection using transition-state analogs or other inhibitors to add various nucleophiles, general acids, or bases to improve catalysis. At each iteration, the union between chemistry and combinatorial selection serves as a powerful tool for defining the three-dimensional space of the active site. The two chain nature of the antibody molecule should be a further advantage because each chain can bring different functionalities into the active site. The order of the selective steps employed in such an iterative procedure is probably important and it would seem best to begin with a transition-state analog in order to give the selection process at the outset the maximum benefit of chemical insight.

Finally, a significant feature of the present experiment deserves emphasis in that it may shed light on the evolution of catalytic mechanisms. Although there was no direct selection for catalysis initially, the active site when selected for a simple chemical transformation had a specificity which allowed catalysis with appropriate substrates. This may be a general principle where one chemical event may be accompanied by additional chemistry of sufficient utility to afford the catalyst a selectable advantage.

Figure 9:
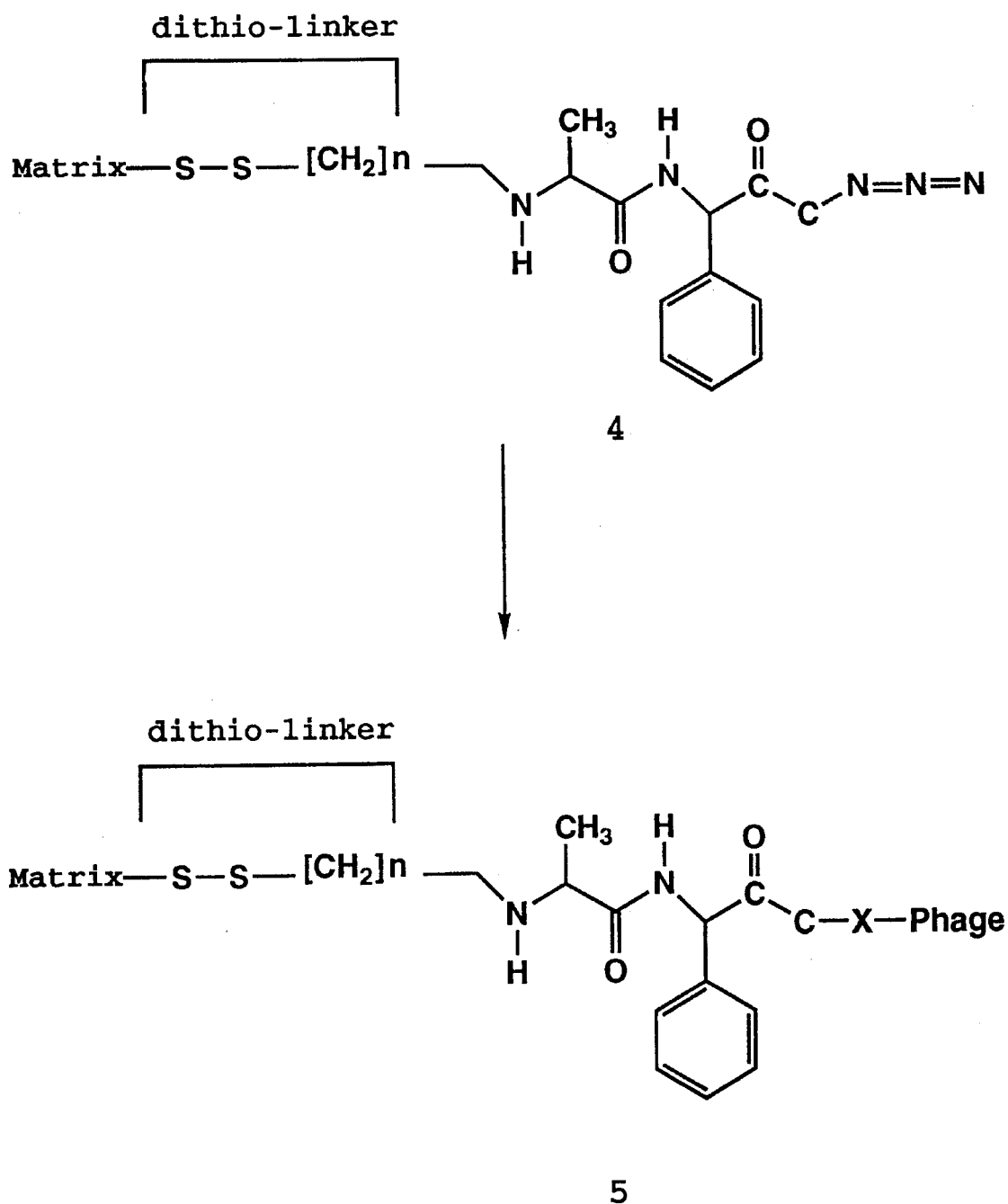
FIG. 9 illustrates immobilized suicide substrates employed for the selection of cysteine or serine nucleophiles.

8. Selection of the Phagemid-Displayed Semisynthetic Fab Heterodimers Containing Cysteine and Serine Residues in the Antibody Active Site: Selection of Antibodies with Novel Serine or Cysteine Proteolytic Catalytic Activity The method for selecting from a semisynthetic phage displayed library a Fab which covalently binds to the immobilized suicide substrate 4 (FIG. 9) is practiced as described in Example 7. The catalytically active molecules selected by their covalent bond formation to compound 4, having nucleophilic residues in their active sites, and having esterolytic and proteolytic activity, are characterized using conventional physical and kinetic procedures analogous to the procedures described in detail in Example 7.

A. Procedures for Practicing Chemical Event Selection

Step A Generating Semisynthetic Phage-Display Libraries: Mutagenezing Combinatorial Antibody Libraries Polypeptides encoding light and heavy chain portions of the Fab are randomized by in vitro mutagenesis as described in Example 2A and 2B. The semisynthetic combinatorial phage libraries (E, F, κ9/E, κ9/F, κ10/E and, κ10/F; Barbas III, C. F., Rosenblum, J. S. & Lerner, R. A. (1993) *Proc. Natl. Acad. Sci. U.S.A.* 90, 6385–6389, Barbas III, C. F, Amberg, W., Simoncsits, A., Jones, T. M. & Lerner, R. A. (1993) *Gene,* 137, 57–62.), or similarly prepared semisynthetic libraries enriched in serine and other nucleophilic residues, are produced as described in Example 3A, 3B and 3C, and then are used in affinity purification.

Step B Multiple Cycles of Affinity Selection of the Phage Library having Phagemid Fab-Displayed Synthetic Binding Site Proteins Enriched in Serine or Cysteine Residues The phage libraries produced as described Example 3A, 3B and 3C are selected as described, in Example 7, on microtiter plates coated with the suicide substrate conjugate target molecule, compound 4.

1. Preparation of Microtiter Plate/Suicide Substrate-Type Affinity Selection Matrix Diazoketones are well known suicide substrates; Silverman, R. B. (1988) *Mechanism-Based Enzyme Inactivation: Chemistry and Enzymology,* Vol. 1 and Vol. 2 (CRC Press, Inc., Boca Raton, Fla.), Walsh, C. (1979) *Enzymatic Reaction Mechanisms,* W.H. Freeman, San Francisco. The affinity label suicide substrate conjugate (containing a conventional dithio-linking group used for DTT elution of the covalent Fab-suicide substrate complex) of the peptide substrate 4 is immobilized on plastic. The BSA conjugate of 4 is prepared under standard conditions; Tijssen P., (1985) "Laboratory Techniques in Biochemistry and Molecular Biology: Practice and Theory of Enzyme Immunoassays", Elsevier, N.Y. The affinity label suicide substrate BSA conjugate, compound 4, is diluted to 0.1 mg/ml, and 25 µl is admixed with the microtiter wells of a microtiter plate (Costar 3690) overnight at 4C. Dried affinity purification matrix is fixed upon adding 50 µl of methanol to microtiter wells previously reacted with compound 4. After 5 minutes, the methanol is discarded and the affinity purification matrix dried at room temperature. The wells are washed twice with water. Preventing nonspecific adsorption of phage or phage-displayed proteins to the affinity purification matrix is accomplished by coating the wells with bovine serum albumin (BSA). Wells are completely filled with a 1% BSA/PBS solution (phosphate-buffered saline; 10 mM sodium phosphate, 150 mM NaCl, pH 7.4) at 37C for 30 minutes. Blocking solution is removed and the wells are used for multiple cycles of affinity selection as described below.

2. PHAGE ENRICHMENT CYCLES NUMBER 1–5

Five cycles of enrichment, each cycle including Steps: A. affinity selecting, B. washing, C. DTT eluting (by cleaving the dithio-linker) of the covalently bound phage-displayed Fab-suicide substrate conjugate, D. amplifying and, E. isolating phage are practiced as described in Example 7.

Figure 10:
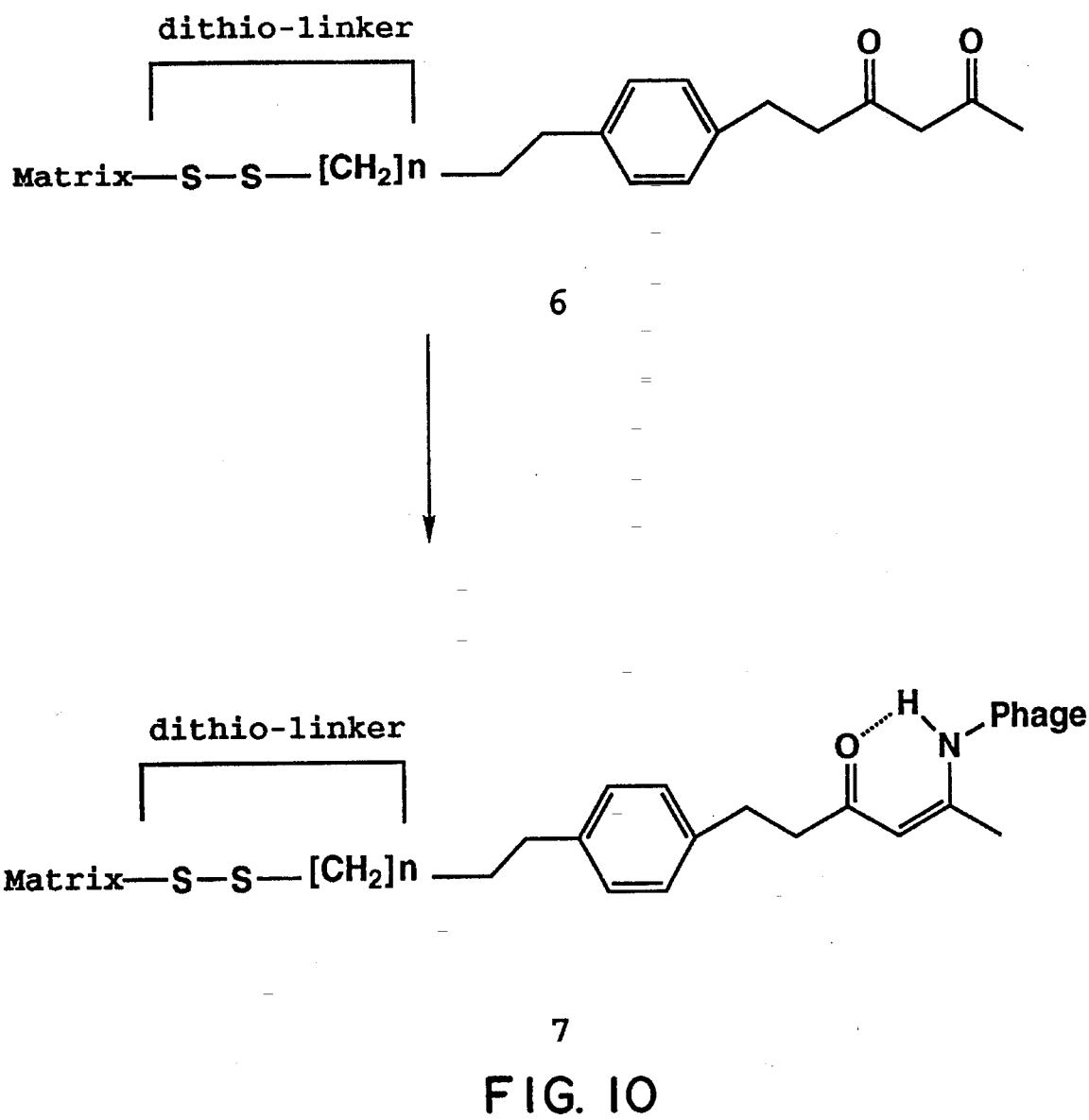
FIG. 10 illustrates immobilized affinity reagent employed for the selection of catalysts of the aldol condensation reaction.

9. Selection of the Phagemid-Display Semisynthetic Fab Heterodimers Containing Lysine Residues in the Antibody Active Site: Selection of Antibodies with Novel Aldolase-Type Catalytic Activity The method for selecting from a semisynthetic phage displayed library a Fab which covalently binds to the immobilized suicide substrate 6 (FIG. 10) is practiced as described in Example 7. The catalytically active molecules selected by their covalent bond formation to compound 6, having nucleophilic residues in their active sites, and having esterolytic and proteolytic activity, are characterized using conventional physical and kinetic procedures analogous to the procedures described in detail in Example 7.

A. Procedures for Practicing Chemical Event Selection

Step A Generating Semisynthetic Phage-Display Libraries: Mutagenezing Combinatorial Antibody Libraries Polypeptides encoding light and heavy chain portions of the Fab are randomized by in vitro mutagenesis as described in Example 2A and 2B. The semisynthetic combinatorial phage libraries (E, F, κ9/E, κ9/F, κ10/E and, κ10/F; Barbas III, C. F., Rosenblum, J. S. & Lerner, R. A. (1993) *Proc. Natl. Acad. Sci. U.S.A.* 90, 6385–6389, Barbas III, C. F, Amberg, W., Simoncsits, A., Jones, T. M. & Lerner, R. A. (1993) *Gene,* 137, 57–62.), or similarly prepared semisynthetic libraries enriched in lysine residues, are produced as described in Example 3A, 3B and 3C, and then are used in affinity purification.

Step B Multiple Cycles of Affinity Selection of the Phage Library having Phagemid Fab-Displayed Synthetic Binding Site Proteins Enriched in Lysine Residues The phage libraries produced as described Example 3A, 3B and 3C are selected as described, in Example 7, on microtiter plates coated with the suicide substrate conjugate target molecule, compound 6.

1. Preparation of Microtiter Plate/Suicide Substrate-Type Affinity Selection Matrix Aldehydes and ketones will readily form imine or Schiff base intermediates with free amines. Beta-Diketones are an affinity label for nucleophilic amines in the Fab active site, i.e., compound 7. The affinity label conjugate (containing a conventional dithio-linking group used for DTT elution of the covalent Fab-suicide substrate complex) of the beta-diketo analog 6 is immobilized on plastic. The BSA conjugate of 6 is prepared under standard conditions; Tijssen P., (1985) "Laboratory Techniques in Biochemistry and Molecular Biology: Practice and Theory of Enzyme Immunoassays", Elsevier, New York. The affinity label suicide substrate BSA conjugate, compound 6, is diluted to 0.1 mg/ml, and 25 µl is admixed with the microtiter wells of a microtiter plate (Costar 3690) overnight at 4C. Dried affinity purification matrix is fixed upon adding 50 µl of methanol to microtiter wells previously reacted with compound 6. After 5 minutes, the methanol is discarded and the affinity purification matrix dried at room temperature. The wells are washed twice with water. Preventing nonspecific adsorption of phage or phage-displayed proteins to the affinity purification matrix is accomplished by coating the wells with bovine serum albumin (BSA). Wells are completely filled with a 1% BSA/PBS solution (phosphate-buffered saline; 10 mM sodium phosphate, 150 mM NaCl, pH 7.4) at 37C for 30 minutes. Blocking solution is removed and the wells are used for multiple cycles of affinity selection as described below.

2. PHAGE ENRICHMENT CYCLES NUMBER 1–5

Five cycles of enrichment, each cycle including Steps: A. affinity selecting, B. washing, C. DTT eluting (by cleaving the dithio-linker) of the covalently bound phage-displayed Fab-suicide substrate conjugate, D. amplifying and, E. isolating phage are practiced as described in Example 7.

10. Selection of the Phagemid-Displayed Semisynthetic Fab Heterodimers Containing Cysteine and Serine Resides in the Antibody Active Site: Selection of Novel β-Lactamase-Type Catalytic Activity The method for selecting from a semisynthetic phage displayed library a Fab which covalently binds to the immobilized suicide substrate beta-lactam analog 8 (FIG. 11) is practiced as described in Example 7. The catalytically active molecules selected by their covalent bond formation to compound 8, having nucleophilic residues in their active sites, and having esterolytic and proteolytic activity, are characterized using conventional physical and kinetic procedures analogous to the procedures described in detail in Example 7.

A. Procedures for Practicing Chemical Event Selection
Step A Generating Semisynthetic Phage-Display Libraries Mutagenezing Combinatorial Antibody Libraries Polypeptides encoding light and heavy chain portions of the Fab are randomized by in vitro mutagenesis as described in Example 2A and 2B. The semisynthetic combinatorial phage libraries (E, F, κ9/E, κ9/F, κ10/E and, κ10/F; Barbas III, C. F., Rosenblum, J. S. & Lerner, R. A. (1993) *Proc. Natl. Acad. Sci. U.S.A.* 90, 6385–6389, Barbas III, C. F, Amberg, W., Simoncsits, A., Jones, T. M. & Lerner, R. A. (1993) *Gene,* 137, 57–62.), or similarly prepared semisynthetic libraries enriched in serine and or cysteine residues, are produced as described in Example 3A, 3B and 3C, and then are used in affinity purification.

Step B Multiple Cycles of Affinity Selection of the Phage Library having Phagemid Fab-Displayed Synthetic Binding Site Proteins Enriched in Serine or Cysteine Residues The phage libraries produced as described Example 3A, 3B and 3C are selected as described, in Example 7, on microtiter plates coated with the suicide substrate conjugate target molecule, compound 8.

1. Preparation of Microtiter Plate/Suicide Substrate-Type Affinity Selection Matrix Beta-lactams are extremely well characterized and readily available suicide substrates for bacterial beta-lactamases; Silverman, R. B. (1988) *Mechanism- Based Enzyme Inactivation: Chemistry and Enzymology,* Vol. 1 and Vol. 2 (CRC Press, Inc., Boca Raton, Fla.), Walsh, C. (1979) *Enzymatic Reaction Mechanisms,* W.H. Freeman, San Francisco. The mechanism of action of beta-lactam antibiotics is to form a slowly hydrolyzing acyl-enzyme intermediate. The acyl intermediate is targeted by compound 8, to yield the acylated phage-displayed Fab, compound 9. The affinity label suicide substrate conjugate (containing a conventional dithio-linking group used for DTT elution of the covalent Fab-suicide substrate complex) of beta-lactam analog 8 is immobilized on plastic. The BSA conjugate of 8 is prepared under standard conditions; Tijssen P., (1985) "Laboratory Techniques in Biochemistry and Molecular Biology: Practice and Theory of Enzyme Immunoassays", Elsevier, N.Y. The affinity label suicide substrate BSA conjugate, compound 8, is diluted to 0.1 mg/ml, and 25 µl is admixed with the microtiter wells of a microtiter plate (Costar 3690) overnight at 4C. Dried affinity purification matrix is fixed upon adding 50 µl of methanol to microtiter wells previously reacted with compound 8. After 5 minutes, the methanol is discarded and the affinity purification matrix dried at room temperature. The wells are washed twice with water. Preventing nonspecific adsorption of phage or phage-displayed proteins to the affinity purification matrix is accomplished by coating the wells with bovine serum albumin (BSA). Wells are completely filled with a 1% BSA/PBS solution (phosphate-buffered saline; 10 mM sodium phosphate, 150 mM NaCl, pH 7.4) at 37C for 30 minutes. Blocking solution is removed and the wells are used for multiple cycles of affinity selection as described below.

2. PHAGE ENRICHMENT CYCLES NUMBER 1–5

Five cycles of enrichment, each cycle including Steps: A. affinity selecting, B. washing, C. DTT eluting (by cleaving the dithio-linker) of the covalently bound phage-displayed Fab-suicide substrate conjugate, D. amplifying and, E. isolating phage are practiced as described in Example 7.

Figure 12:
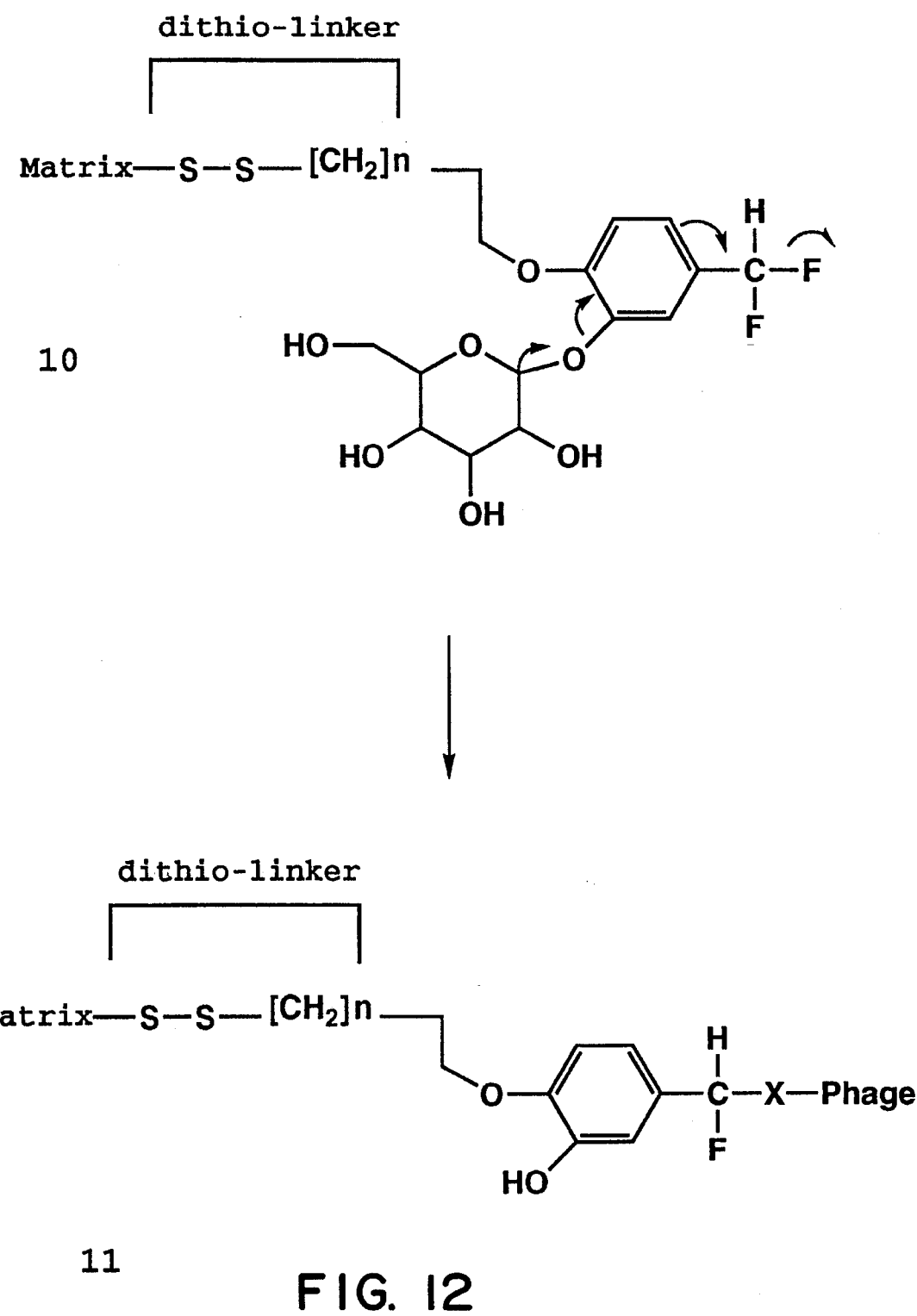
FIG. 12 illustrates immobilized suicide substrates employed for the selection of glycosidase activity.

11. Selection of the Phagemid-Displayed Semisynthetic Fab Heterodimers Containing Glutamate and Aspartate Residues in the Antibody Active Site: Selection of Novel Glycosidase-Type Catalytic Activity The method for selecting from a semisynthetic phage displayed library a Fab which covalently binds to the immobilized suicide substrate analog 10 (FIG. 12) is practiced as described in Example 7. The catalytically active molecules selected by their covalent bond formation to compound 10, having nucleophilic residues in their active sites, and having esterolytic and proteolytic activity, are characterized using conventional physical and kinetic procedures analogous to the procedures described in detail in Example 7.

A. Procedures for Practicing Chemical Event Selection
Step A Generating Semisynthetic Phage-Display Libraries: Mutagenezing Combinatorial Antibody Libraries Polypeptides encoding light and heavy chain portions of the Fab are randomized by in vitro mutagenesis as described in Example 2A and 2B. The semisynthetic combinatorial phage libraries (E, F, κ9/E, κ9/F, κ10/E and, κ10/F; Barbas III, C. F., Rosenblum, J. S. & Lerner, R. A. (1993) *Proc. Natl. Acad. Sci. U.S.A.* 90, 6385–6389, Barbas III, C. F, Amberg, W., Simoncsits, A., Jones, T. M. & Lerner, R. A. (1993) *Gene,* 137, 57–62.), or similarly prepared semisynthetic libraries enriched in glutamic acid and or aspartic acid residues, are produced as described in Example 3A, 3B and 3C, and then are used in affinity purification.

Step B Multiple Cycles of Affinity Selection of the Phage Library having Phagemid Fab-Displayed Synthetic Binding Site Proteins Enriched in Glutamic and Aspartic Acid Residues The phage libraries produced as described Example 3A, 3B and 3C are selected as described, in Example 7, on microtiter plates coated with the suicide substrate conjugate target molecule, compound 10.

1. Preparation of Microtiter Plate/Suicide Substrate-Type Affinity Selection Matrix Difluoromethyl aryl-beta-D-glucosides are known suicide substrates of beta-glucosidase; Halazy, S. et al., (1990) *Bioorganic Chemistry*, 18, 330–344. Displacement of the glucosyl moiety in compound 10, by catalytic action of the phage-displayed Fab, causes generation of a Michael acceptor which irreversibly binds a nucleophile in the Fab active site, 11. The affinity label suicide substrate conjugate (containing a conventional dithio-linking group used for DTT elution of the covalent Fab-suicide substrate complex) of analog 10 is immobilized on plastic. The BSA conjugate of 10 is prepared under standard conditions; Tijssen P., (1985) "Laboratory Techniques in Biochemistry and Molecular Biology: Practice and Theory of Enzyme Immunoassays", Elsevier, N.Y. The affinity label suicide substrate BSA conjugate, compound 10, is diluted to 0.1 mg/ml, and 25 μl is admixed with the microtiter wells of a microtiter plate (Costar 3690) overnight at 4C. Dried affinity purification matrix is fixed upon adding 50 μl of methanol to microtiter wells previously reacted with compound 10. After 5 minutes, the methanol is discarded and the affinity purification matrix dried at room temperature. The wells are washed twice with water. Preventing nonspecific adsorption of phage or phage-displayed proteins to the affinity purification matrix is accomplished by coating the wells with bovine serum albumin (BSA). Wells are completely filled with a 1% BSA/PBS solution (phosphate-buffered saline; 10 mM sodium phosphate, 150 mM NaCl, pH 7.4) at 37C for 30 minutes. Blocking solution is removed and the wells are used for multiple cycles of affinity selection as described below.

2. PHAGE ENRICHMENT CYCLES NUMBER 1–5

Five cycles of enrichment, each cycle including Steps: A. affinity selecting, B. washing, C. DTT eluting (by cleaving the dithio-linker) of the covalently bound phage-displayed Fab-suicide substrate conjugate, D. amplifying and, E. isolating phage are practiced as described in Example 7.

12. Selection of the Phagemid-Displayed Semisynthetic Fab Heterodimers Containing Nucleophilic and General Acid-Base Type Residues in the Antibody Active Site: Selecting Novel Ribonuclease- (RNase)-Type Catalytic Activity The method for selecting from a semisynthetic phage displayed library a Fab which covalently binds to the immobilized suicide substrate analog 12 (FIG. 13) is practiced as described in Example 7. The catalytically active molecules selected by their covalent bond formation to compound 12, having nucleophilic residues in their active sites, and having esterolytic and proteolytic activity, are characterized using conventional physical and kinetic procedures analogous to the procedures described in detail in Example 7.

A. Procedures for Practicing Chemical Event Selection

Step A Generating Semisynthetic Phage-Display Libraries: Mutagenezing Combinatorial Antibody Libraries Polypeptides encoding light and heavy chain portions of the Fab are randomized by in vitro mutagenesis as described in Example 2A and 2B. The semisynthetic combinatorial phage libraries (E, F, κ9/E, κ9/F, κ10/E and, κ10/F; Barbas III, C. F., Rosenblum, J. S. & Lerner, R. A. (1993) *Proc. Natl. Acad. Sci. U.S.A.* 90, 6385–6389, Barbas III, C. F, Amberg, W., Simoncsits, A., Jones, T. M. & Lerner, R. A. (1993) *Gene*, 137, 57–62.), or similarly prepared semisynthetic libraries enriched in glutamic acid and or aspartic acid residues, are produced as described in Example 3A, 3B and 3C, and then are used in affinity purification.

Step B Multiple Cycles of Affinity Selection of the Phage Library having Phagemid Fab-Displayed Synthetic Binding Site Proteins Enriched Nucleophilic and General Acid-Base Type Residues The phage libraries produced as described Example 3A, 3B and 3C are selected as described, in Example 7, on microtiter plates coated with the suicide substrate conjugate target molecule, compound 12.

3. Preparation of Microtiter Plate/Suicide Substrate-Type Affinity Selection Matrix Difluoromethyl aryl-ribosides are suicide substrates for ribonuclease (RNase). The released difluoromethylaryl moiety is an activated Michael acceptor which readily binds irreversibly to active site Fab nucleophiles, 13. The affinity label suicide substrate conjugate (containing a conventional dithio-linking group used for DTT elution of the covalent Fab-suicide substrate complex) of the RNA analog 12 is immobilized on plastic. The BSA conjugate of 12 is prepared under standard conditions; Tijssen P., (1985) "Laboratory Techniques in Biochemistry and Molecular Biology: Practice and Theory of Enzyme Immunoassays", Elsevier, N.Y. The affinity label suicide substrate BSA conjugate, compound 12, is diluted to 0.1 mg/ml, and 25 μl is admixed with the microtiter wells of a microtiter plate (Costar 3690) overnight at 4C. Dried affinity purification matrix is fixed upon adding 50 μl of methanol to microtiter wells previously reacted with compound 12. After 5 minutes, the methanol is discarded and the affinity purification matrix dried at room temperature. The wells are washed twice with water. Preventing nonspecific adsorption of phage or phage-displayed proteins to the affinity purification matrix is accomplished by coating the wells with bovine serum albumin (BSA). Wells are completely filled with a 1% BSA/PBS solution (phosphate-buffered saline; 10 mM sodium phosphate, 150 mM NaCl, pH 7.4) at 37C for 30 minutes. Blocking solution is removed and the wells are used for multiple cycles of affinity selection as described below.

2. PHAGE ENRICHMENT CYCLES NUMBER 1–5

Five cycles of enrichment, each cycle including Steps: A. affinity selecting, B. washing, C. DTT eluting (by cleaving the dithio-linker) of the covalently bound phage-displayed Fab-suicide substrate conjugate, D. amplifying and, E. isolating phage are practiced as described in Example 7.

Figure 14:
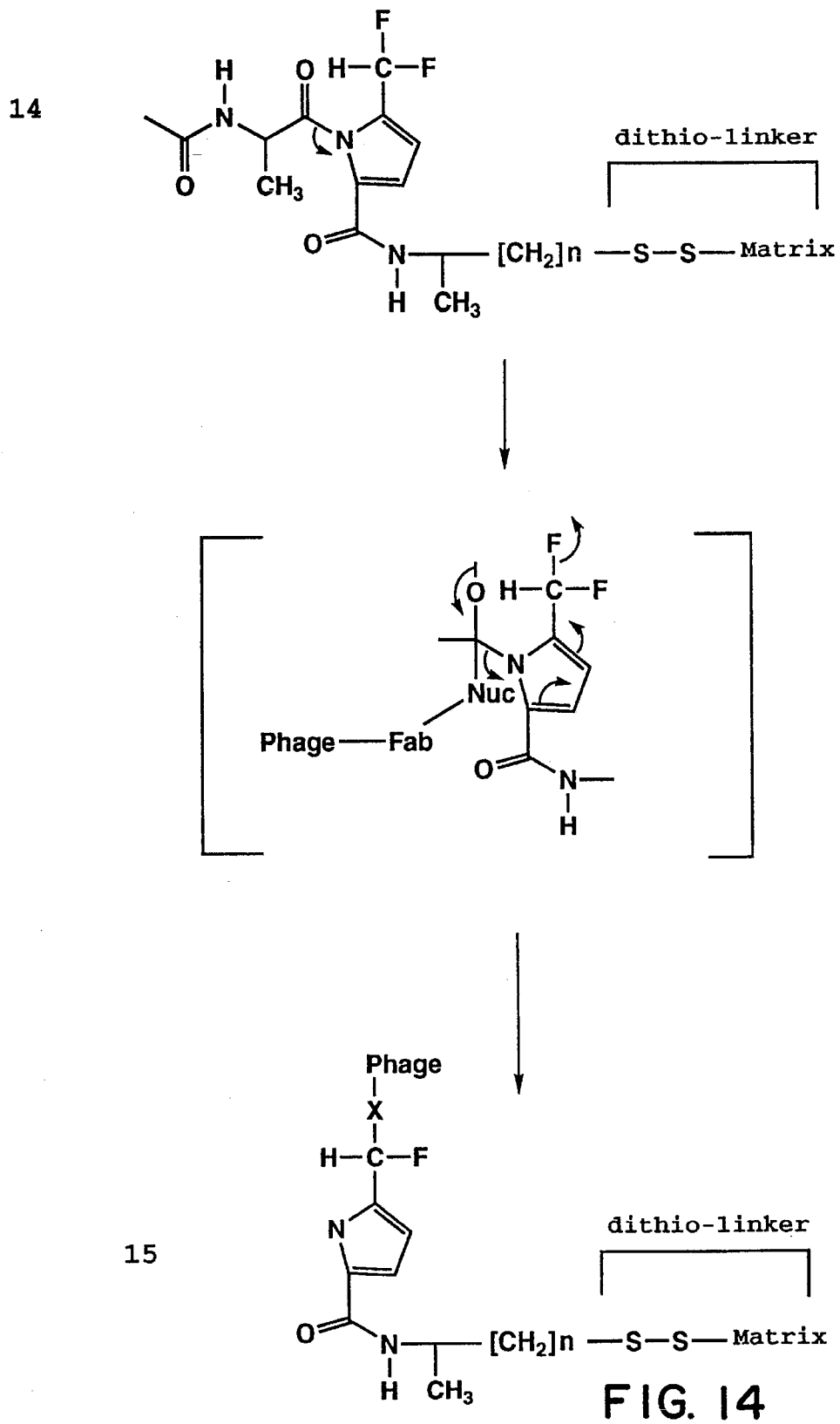
FIG. 14 illustrates immobilized suicide substrates employed for the selection of Proteolytic activity.

13. Selection of the Phagemid-Displayed Semisynthetic Fab Heterodimers Containing Serine or Cysteine Residues in the Antibody Active Site: Selecting Novel Proteolytic Catalytic Activity The method for selecting from a semisynthetic phage displayed library a Fab which covalently binds to the immobilized suicide substrate analog 14 (FIG. 14) is practiced as described in Example 7. The catalytically active molecules selected by their covalent bond formation to compound 14, having nucleophilic residues in their active sites, and having esterolytic and proteolytic activity, are characterized using conventional physical and kinetic procedures analogous to the procedures described in detail in Example 7.

A. Procedures for Practicing Chemical Event Selection

Step A Generating Semisynthetic Phage-Display Libraries: Mutagenezing Combinatorial Antibody Libraries Polypeptides encoding light and heavy chain portions of the Fab are randomized by in vitro mutagenesis as described in Example 2A and 2B. The semisynthetic combinatorial phage libraries (E, F, κ9/E, κ9/F, κ10/E and, κ10/F; Barbas III, C. F., Rosenblum, J. S. & Lerner, R. A. (1993) *Proc. Natl. Acad. Sci. U.S.A.* 90, 6385–6389, Barbas III, C. F, Amberg, W., Simoncsits, A., Jones, T. M. & Lerner, R. A. (1993) *Gene*, 137, 57–62), or similarly prepared semisynthetic libraries enriched in serine or cysteine residues, are produced as described in Example 3A, 3B and 3C, and then are used in affinity purification..

Step B Multiple Cycles of Affinity Selection of the Phage Library having Phagemid Fab-Displayed Synthetic Binding Site Proteins Enriched Serine and Cysteine Residues The phage libraries produced as described Example 3A, 3B and 3C are selected as described, in Example 7, on microtiter plates coated with the suicide substrate conjugate target molecule, compound 14.

1. Preparation of Microtiter Plate/Suicide Substrate-Type Affinity Selection Matrix The affinity label suicide substrate conjugate (containing a conventional dithio-linking group used for DTT elution of the covalent Fab-suicide substrate complex) of the peptide analog 14 is immobilized on plastic. The BSA conjugate of 14 is prepared under standard conditions; Tijssen P., (1985) "Laboratory Techniques in Biochemistry and Molecular Biology: Practice and Theory of Enzyme Immunoassays", Elsevier, N.Y. The affinity label suicide substrate BSA conjugate, compound 14, is diluted to 0.1 mg/ml, and 25 μl is admixed with the microtiter wells of a microtiter plate (Costar 3690) overnight at 4C. Dried affinity purification matrix is fixed upon adding 50 μl of methanol to microtiter wells previously reacted with compound 14. After 5 minutes, the methanol is discarded and the affinity purification matrix dried at room temperature. The wells are washed twice with water. Preventing nonspecific adsorption of phage or phage-displayed proteins to the affinity purification matrix is accomplished by coating the wells with bovine serum albumin (BSA). Wells are completely filled with a 1% BSA/PBS solution (phosphate-buffered saline; 10 mM sodium phosphate, 150 mM NaCl, pH 7.4) at 37C for 30 minutes. Blocking solution is removed and the wells are used for multiple cycles of affinity selection as described below.

2. PHAGE ENRICHMENT CYCLES NUMBER 1–5

Five cycles of enrichment, each cycle including Steps: A. affinity selecting, B. washing, C. DTT eluting (by cleaving the dithio-linker) of the covalently bound phage-displayed Fab-suicide substrate conjugate, D. amplifying and, E. isolating phage are practiced as described in Example 7.

The foregoing written specification is considered to be sufficient to enable one skilled in the art to practice the invention. Indeed, various modifications of the invention in addition to those shown and described herein will become apparent to those skilled in the art from the foregoing description and fall within the scope of the appended claims.

---

What is claimed is:

1. A method for panning a phage display protein library displaying an encoded protein having covalent catalytic activity, the method comprising the following steps:

Step A. contacting the phage display protein library with an immobilized suicide substrate for forming a covalent conjugate between the immobilized suicide substrate and the encoded protein having covalent catalytic activity; then Step B. separating and isolating the covalent conjugate obtained in said Step A with respect to non-covalently bound components and unbound components of the phage display protein library; and then Step C. decoding the encoded protein incorporated within the covalent conjugate isolated in said Step B for identifying the encoded protein having covalent catalytic activity.

2. A method for panning an encoded protein library for an encoded protein having covalent catalytic activity as described in claim 1 wherein the catalytic activity is selected from the group consisting of esterolytic activity, aldol condensation activity, β-lactamase activity, glycosidase activity, RNase activity, and proteolytic activity.

3. A chemical complex comprising:

a solid phase, a suicide substrate covalently linked to said solid phase, a catalytically active protein covalently linked to said suicide substrate for forming a covalent protein/suicide substrate conjugate, said catalytically active protein, when not covalently linked to said suicide substrate, having a covalent catalytic activity wherein, the catalytically active protein is displayed on a phage having a nucleotide sequence encoding the catalytically active protein displayed thereon, whereby said phage is immobilized on the solid phase via said catalytically active protein.

4. A method for catalytically converting a substrate to a product, the method comprising the following steps:

Step A: providing a catalytic protein having a covalent catalytic activity with respect to both the substrate and an immobilized suicide substrate according to the following substeps:

Substep 1: contacting a phage display protein library with the immobilized suicide substrate, said contacting resulting in the formation of a covalent conjugate between the immobilized suicide substrate and the catalytic protein; then Substep 2: separating and isolating the covalent conjugate obtained in said Substep 1 with respect to noncovalently bound components and unbound components of the phage display protein library; then Substep 3: decoding the catalytic protein incorporated within the covalent conjugate isolated in said Substep 2; then Substep 4: producing the catalytic protein identified in said Substep 3; and then Step B: contacting the catalytic protein of said Step A with the substrate under reaction conditions for producing the product.

5. A method for catalytically converting a substrate to a product as described in claim 4 wherein the catalytic activity of the catalytic protein is selected from the group consisting of esterolytic activity, aldol condensation activity, β-lactamase activity, glycosidase activity, RNase activity, and proteolytic activity.

* * * * *

UNITED STATES PATENT AND TRADEMARK OFFICE
Certificate

Patent No. 5,571,681

Patented: November 5, 1996

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Kim D. Janda, San Diego, CA; Carlos Barbas, San Diego, CA; and Richard A. Lerner, La Jolla, CA Signed and Sealed this Eighth Day of January 2002.

ROBERT WAX
*Supervisory Patent Examiner*
Art Unit 1652